US006593497B1

(12) United States Patent
Choi et al.

(10) Patent No.: US 6,593,497 B1
(45) Date of Patent: Jul. 15, 2003

(54) β2-ADRENERGIC RECEPTOR AGONISTS

(75) Inventors: Seok-Ki Choi, Palo Alto, CA (US); Edmund J. Moran, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 09/504,761

(22) Filed: Feb. 14, 2000

Related U.S. Application Data

(63) Continuation of application No. 09/323,939, filed on Jun. 2, 1999, now abandoned.

(51) Int. Cl.[7] .............. C07C 211/00; C07C 213/00; C07D 401/00; C07D 215/16; C07D 209/82; A01N 33/02; A61K 31/135

(52) U.S. Cl. .............. 564/372; 435/7.1; 435/7.2; 436/501; 436/518; 564/347; 544/62; 544/360; 544/363; 544/370; 544/372; 544/373; 544/380; 544/382; 546/156; 549/404; 548/325.5; 548/346.1; 548/440; 548/486; 548/490; 514/649; 514/651; 514/653

(58) Field of Search .............. 435/7.1, 7.2; 436/501, 436/518; 564/372, 347; 544/62, 360, 363, 370, 372, 373, 380, 382; 548/325.5, 346.1, 440, 486, 490; 546/156; 549/404; 514/649, 651, 653

(56) References Cited

U.S. PATENT DOCUMENTS

| | | | |
|---|---|---|---|
| 3,875,233 A | 4/1975 | Bastian et al. | |
| 4,021,485 A | 5/1977 | Schromm et al. | |
| 4,304,721 A | 12/1981 | Fahrenholtz et al. | |
| 4,587,046 A | 5/1986 | Goodman et al. | |
| 5,463,564 A | 10/1995 | Agrafiotis et al. | |

FOREIGN PATENT DOCUMENTS

| | | |
|---|---|---|
| CH | 550768 A | 6/1974 |
| DE | 1158082 B | 1/1963 |
| EP | 00145067 | 6/1985 |
| EP | 0 196 849 A | 10/1986 |
| EP | 0 233 686 A | 8/1987 |
| GB | 1 394 542 | 5/1975 |
| GB | 1 040 724 | 9/1996 |
| JP | 10152460 | 6/1998 |
| JP | 10-152460 | 6/1998 |
| WO | WO 92/05802 | 4/1992 |
| WO | WO 96/19987 | 7/1996 |
| WO | WO 97/35195 | 9/1997 |
| WO | 98/00439 | 1/1998 |
| WO | 98/03632 | 1/1998 |
| WO | WO 98/03632 | 1/1998 |
| WO | 98/11436 | 3/1998 |
| WO | 98/21275 | 9/1998 |
| WO | 99/64035 | 12/1999 |

OTHER PUBLICATIONS

Chemical Abstract 65; 3796–3797 (1966) (published by The American Chemical Society).
Chemical Abstract 63;11435b (1965) (published by The American Chemical Society).
Chemical Abstract 76; 14096s (1972) (published by The American Chemical Society).
Chemical Abstract 66; 379 (1966) (published by The American Chemical Society).
Chemical Abstract 74; 42149 (1971). (published by The American Chemical Society).
Chemical Abstract 74; 87613. (1971). (published by The American Chemical Society).
Chemical Abstract 75; 35405 (1971). (published by The American Chemical Society).
Chemical Abstract 78; 57999 (1973). (published by The American Chemical Society).
Chemical Abstract 79; 126069 (1973). (published by The American Chemical Society).
Chemical Abstract 79; 126063 (1973).(published by The American Chemical Society).
Chemical Abstract 79; 5128 (1973). (published by The American Chemical Society).
Chemical Abstract 79; 104935 (1973). (published by The American Chemical Society).
Chemical Abstract 82; 3968 (1975). (published by The American Chemical Society).
Jacobi, et al. *Arzneim. Forsch* (GE); 30; 8a; 1980; 1348–1362 (Summary in English).
Stormann, et al. *Arzneim. Forsch;* 23; 1973; (Summary in English).
Auterhoff, L. *Lehrbuch der Pharmazeutischen Chemie.* 12th Edition.
Cole, B.M., et al. "Discovery of Chiral Catalysts through Ligand Diversity: Ti–Catalyzed Enantioselective Addition of TMSCN to meso Epoxides." *Angew.. Chem. Int. Ed. Engl.* 35(15): 1668–1671 (1996).
Davis, P.W., et al. "Drug Leads from Combinatorial Phosphodiester Libraries." *J. Med. Chem.* 38: 4363–4366 (1995).
Menger, F.M., et al. "Phosphatase Catalysis Developed via Combinatorial Organic Chemistry." *J. Org. Chem.* 60: 6666–6667 (1995).
Pitha, J., et al. "Macromolecular B–adrenergic antagonists discriminating between receptor and antibody." *Proc. Natl. Acad. Sci. USA*. 77(4): 2219–2223 (1980).

(List continued on next page.)

*Primary Examiner*—Maurie Baker
(74) *Attorney, Agent, or Firm*—Jeffrey A. Hagenah; Roberta P. Saxon; Joyce G. Cohen

(57) ABSTRACT

The present invention is directed to multibinding compounds which are β2 adrenergic receptor agonists and are therefore useful in the treatment and prevention of respiratory diseases such asthma, bronchitis, and the like. They are also useful in the treatment of nervous system injury and premature labor.

8 Claims, 3 Drawing Sheets

OTHER PUBLICATIONS

Kusiak, J.W., et al. "β–adrenergic pharmacores on the same molecule. A set of agonist–antagonist combinations." *Biochem. Pharmacol.* 36(2): 269–275 (1987).

Zeng, et al. "Automated Analytical/Preparative High Performance Liquid Chromatography–Mass Spectrometry System for the Rapid Characterization and Purification of Compound Libraries." *J. Chrom. A.* 794:3–13 (1998).

Alvarez, et al. *J. Med. Chem.* 30,7, 1186–1193 (1987).

Barnes, P.J. "Current Therapies for Asthma." *Chest* 111:17S–26S (1997).

Beck–Sickinger, A.G. "Structure Characterization and Binding sites of G–Protein–coupled Receptors." *DDT*, 1, 502–513 (1996).

Carrithers, M., et al. "Synthesis and characterization of bivalent peptide ligands targeted to G–protein coupled receptors." *Chem. and Biol.* 3:537 (1996).

Dupuis, DS., et al. "Magnitude of 5–HT1b and 5–HT1A receptor activation in guinea–pig rat brain: evidence from sumatriptan [$^{35}$S]GTPγSbinding responses." *Molecular Brain Research* 67: 107–123 (1999).

Hein, L. and Kobilka, B.K. "Adrenergic Receptor Signal Transduction and Regulation." *Neuropharmacol*, 34, 357–366 (1995).

Howe, R., et al. "B–Adrenergic Blocking Agents. VII. 2–(1,4–Benzodioxanyl) and 2–Chromanyl Analogs of Pronethalol [1–Isopropylamino–1–(2–napthyl)ethanol]." *J. Med. Chem.* 13(2): 169–176 (1970).

Jack, D.A. "A Way of Looking at Agonism and Antagonism: Lessons from Salbutamol, Salmeterol and other β–Adrenoceptor Agonists." *Br. J. Clim. Pharmac.* 31, 501–514 (1991).

Jansen, P.A.J. "Nebivolol: A New Form of Cardiovascular Therapy." *Drug Investigation.* 3 (Suppl. 1) 1–2 (1991).

Kierstead, R.W., et al. $\beta_1$–Selective Adrenoceptor Antagonists. 1. Synthesis and β–Adrenergic Blocking Activity of a Series of Binary (Aryloxy)propanolamines. *J. Med. Chem.* 26, 1561–1569 (1983).

Kizuka, H., "B–Adrenoceptor Antagonist Activity of Bivalent Ligands. 1. Diamide Analogues of Practolol." *J. Med. Chem.* 30, 726–729 (1987).

Machin, P.J., et al. "B1–Selective Adrenocepto Antagonists. 2.4–Ether–Linked Phenoxypropanolamines." *J. Med Chem.* 26, 1561–1569 (1983).

Milecki, J. "Carbostyril Derivatives Having potent B–Adrenergic Agonist Properties." *J. Med. Chem.* 30, 9, 1563–1566 (1987).

Pauwels, P.J., et al. "Human β1– and β2– Adrenergic Receptor Binding and Mediated Accumulation of cAMP in Transfected Chinese Hamster Ovary Cells." *Biochemical Pharmacology.* 42(9): 1683–1689 (1991).

Pauwels, P.J., et al. "The Receptor Binding Profile of the New antihypertensive Angents Nebivolol and Its Stereoisomers Compared with Various β–Adrenergic Blockers." *Molecular Pharmacology.* 34: 843–851 (1988).

Pinder, R.M. et al. "Hexoprenaline: A Review of its Pharmacological Properties and Therapeutic Efficacy with Particular Reference to Asthma." *Drugs.* 14: 1–28 (1977).

Pitha, J. et al. "B–Adrenergic Antagonists with Multiple Pharmacophores: Persitent Blockade of Receptors." *J. Med. Chem.* 26, 7–11 (1983).

Portughese, Philip S. "the Role of Concepts in Structure—Activity Relationship Studies of Opioid Ligands." J. Med. Chem. 35(11): 1927–1937 (1992).

Shuker, S.B., et al. "Discovering High–Affinity Ligands for Proteins: SAR by NMR." *Science.* 274, 1531–1534 (1996).

Siegel, M.G., et al. "The Use of High–Thoughput Synthesis and Purification in the Preparation of a Directed Library of Adrenergic Agents." *Mol. Diversity.* 3, 2, 113–116 (1998).

Strosberg, A.D. "Structure, Function, and Regulation of Adrenergic Receptors."*Protein Sci.* 2, 1198–1209 (1993).

Strosberg, A.D. Et Pietri–Rouxel, F. "Function, and Regulation of β3–Adrenoceptor." *TiPS,* 17, 373–381 (1996).

Van de Water, A., et al. "Pharmacoligical and Hemodynamic Profile of Nebivolol, a Chemically Novel, Potent, and Selective β1–Adrenergic Antagonist." *J. of Cardiovascular Pharmacology.* 11: 552–563 (1988).

Van Lommen, G., et al. "Synthesis and Pharmacological Properties of Nebivolol, a new antihypertensive compound." *J. Pharm. Belg.* 446(6): 355–360 (1990).

Verlander, et al. "Biological Activity of Catecholamines Covalently Linked to Synthetic Polymers: Proof of Immobilized Drug Theory." *Proc. Nat'l. Acad. Sci. USA,* 73:4 (1976) 1009–1013.

Weiser, M, et al. "The Pharmacologic Approach to the Treatment of Obesity." *J. Clin. Pharm.* 34, 453–473, No date.

Yokoi, K., et al. "The Development of a Radioimmunoassay for Fortmoterol." *Life Science,* 33, 1665–1672 (1983).

β2-ADRENERGIC RECEPTOR AGONISTS

CROSS-REFERENCE TO RELATED APPLICATIONS

This application claims priority under 35 U.S.C. §120 to U.S. Ser. No. 09/323,939 filed on Jun. 2, 1999 (now abandoned), the entire contents of which are hereby incorporated by reference.

BACKGROUND OF THE INVENTION

1. Field of the Invention

This invention relates to novel multibinding compounds (agents) that are β2 adrenergic receptor agonists and pharmaceutical compositions comprising such compounds. Accordingly, the multibinding compounds and pharmaceutical compositions of this invention are useful in the treatment and prevention of respiratory diseases such as asthma and chronic bronchitis. They are also useful in the treatment of nervous system injury and premature labor.

2. References

The following publications are cited in this application as superscript numbers:

[1] Hardman, J. G., et al. "The Pharmacological Basis of Therapeutics", McGraw-Hill, New York, (1996)

[2] Strosberg, A. D. "Structure, Function, and Regulation of Adrenergic Receptors" *Protein Sci.* 2, 1198–1209 (1993).

[3] Beck-Sickinger, A. G. "Structure Characterization and Binding Sites of G-Protein-coupled Receptors" *DDT*, 1, 502–513, (1996).

[4] Hein, L. & Kobilka, B. K. "Adrenergic Receptor Signal Transduction and Regulation" *Neuropharmacol*, 34, 357–366, (1995).

[5] Strosberg, A. D. & Pietri-Rouxel, F. "Function, and Regulation of β3 Adrenoceptor" *TiPS*, 17, 373–381, (1996).

[6] Barnes, P. J. "Current Therapies for Asthma" *CHEST*, 111:17S–26S, (1997).

[7] Jack, D. A. "A way of Looking at Agonism and Antagonism: Lessons from Salbutamol, Salmeterol and other β-Adrenoceptor Agonists" *Br. J. Clin. Pharmac.* 31, 501–514, (1991).

[8] Kissei Pharmaceutical Co. Ltd. "2-Amino-1-(4-hydroxy-2-methyl-phenyl)propanol derivatives" JP-10152460 (Publication date Jun. 9, 1998).

All of the above publications are herein incorporated by reference in their entirety to the same extent as if each individual publication was specifically and individually indicated to be incorporated by reference in its entirety.

3. State of the Art

A receptor is a biological structure with one or more binding domains that reversibly complexes with one or more ligands, where that complexation has biological consequences. Receptors can exist entirely outside the cell (extracellular receptors), within the cell membrane (but presenting sections of the receptor to the extracellular milieu and cytosol), or entirely within the cell (intracellular receptors). They may also function independently of a cell (e.g., clot formation). Receptors within the cell membrane allow a cell to communicate with the space outside of its boundaries (i.e., signaling) as well as to function in the transport of molecules and ions into and out of the cell.

A ligand is a binding partner for a specific receptor or family of receptors. A ligand may be the endogenous ligand for the receptor or alternatively may be a synthetic ligand for the receptor such as a drug, a drug candidate or a pharmacological tool.

The super family of seven transmembrane proteins (7-TMs), also called G-protein coupled receptors (GPCRs), represents one of the most significant classes of membrane bound receptors that communicate changes that occur outside of the cell's boundaries to its interior, triggering a cellular response when appropriate. The G-proteins, when activated, affect a wide range of downstream effector systems both positively and negatively (e.g., ion channels, protein kinase cascades, transcription, transmigration of adhesion proteins, and the like).

Adrenergic receptors (AR) are members of the G-protein coupled receptors that are composed of a family of three receptor sub-types: $\alpha 1\ _{(A,B,D)}\ \alpha 2\ _{(A,B,C)}$ and $\beta_{(1,2,3)}$.[1-5] These receptors are expressed in tissues of various systems and organs of mammals and the proportions of the α and the β receptors are tissue dependant. For example, tissues of bronchial smooth muscle express largely β2-AR while those of cutaneous blood vessels contain exclusively α-AR sub-types.

It has been established that the β2-AR sub-type is involved in respiratory diseases such as such as asthma[6] and chronic bronchitis, nervous system injury, and premature labor[8]. Currently, a number of drugs e.g., albuterol, formoterol, isoprenolol, or salmeterol having β2-AR agonist activities are being used to treat asthma. However, these drugs have limited utility as they are either non-selective thereby causing adverse side effects such as muscle tremor, tachycardia, palpitations, and restlesness[6], or have short duration of action and/or slow onset time of action.[7] Accordingly, there is a need for β2-selective AR agonists that are fast acting and have increased potency and/or longer duration of action.

The multibinding compounds of the present invention fulfill this need.

SUMMARY OF THE INVENTION

This invention is directed to novel multibinding compounds (agents) that are agonists of β2 adrenergic receptor and are therefore useful in the treatment and prevention of respiratory diseases such as asthma and chronic bronchitis. They are also useful in the treatment of nervous system injury and premature labor.

Accordingly, in one of its composition aspects, this invention provides a multibinding compound of Formula (I):

wherein:
p is an integer of from 2 to 10;
q is an integer of from 1 to 20,
L is a ligand wherein:
one of the ligands, L, is a compound of formula (a):

wherein:
Ar$^1$ is selected from the group consisting of aryl, heteroaryl, cycloalkyl, substituted cycloalkyl, and heterocyclyl wherein each of said $Ar^1$ and $Ar^2$ substituent optionally links the ligand to a linker;

$R^1$ is selected from the group consisting of hydrogen, alkyl, and substituted alkyl, or $R^1$ is a covalent bond linking the ligand to a linker;

$R^2$ and $R^3$ are independently selected from the group consisting of hydrogen, alkyl, acyl, and substituted alkyl, or $R^2$ and $R^3$ are a covalent bond linking the ligand to a linker; and the other ligands are independently selected from a compound of formula (b):

—Q—$Ar^2$ (b)

wherein:

$Ar^2$ is selected from the group consisting of aryl, heteroaryl, cycloalkyl, substituted cycloalkyl, and heterocyclyl;

Q is a covalent bond, or a substituted alkylene group wherein one or more of the carbon atoms in said substituted alkylene group is optionally replaced by a substituent selected from —$NR^a$— (where $R^a$ is hydrogen, alkyl, acyl, or a covalent bond linking the ligand to a linker), —O—, —S(O)$_n$ (where n is an integer of from 0 to 2), —CO—, —$PR^b$— (where $R^b$ is alkyl), —P(O)$_2$—, and —O—P(O)O— and links the ligand to a linker;

each linker, X, in the multibinding compound of Formula (I) independently has the formula:

—$X^a$—Z—($Y^a$—Z)$_m$—$X^a$— wherein:

m is an integer of from 0 to 20;

$X^a$ at each separate occurrence is selected from the group consisting of —O—, —S—, —NR—, —C(O)—, —C(O)O—, —OC(O)—, —C(O)NR—, —NRC(O)—, C(S), —C(S)O—, —C(S)NR—, —NRC(S)—, or a covalent bond where R is as defined below;

Z at each separate occurrence is selected from the group consisting of alkylene, substituted alkylene, alkenylene, substituted alkenylene, alkynylene, substituted alkynylene, or a covalent bond;

each $Y^a$ at each separate occurrence is selected from the group consisting of —O—, —C(O)—, —OC(O)—, —C(O)O—, —NR—, —S(O)n—, —C(O)NR'—, —NR'C(O)—, —NR'C(O)NR'—, —NR'C(S)NR'—, —C(=NR')—NR'—, —NR'—C(=NR')—, —OC(O)—NR'—, —NR'—C(O)—O—, —N=C($X^a$)—NR'—, —NR'—C($X^a$)=N—, —P(O)(OR')—O—, —O—P(O)(OR')—, —S(O)$_n$CR' R"—, —S(O), —NR'—, —NR'—S(O)$_n$—, and a covalent bond; where n is 0, 1 or 2; and R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclic provided that $X^a$, $X^b$, and Z are not covalent bonds at the same time; and pharmaceutically acceptable salts thereof provided that:

(i) when Q is a 2-hydroxyethylamino group then the linker is not alkylene or —C(O)-alkylene-C(O)—; and (ii) when Q, $X^a$, and $X^b$ are covalent bonds then Z is not alkylene.

Preferably, q is less than p in the multibinding compounds of this invention.

In another aspect, this invention provides a pharmaceutical composition comprising a pharmaceutically acceptable carrier and an effective amount of a multibinding compound of Formula (I):

(L)$_p$(X)$_{-q}$ (I)

wherein:

p is an integer of from 2 to 10;

q is an integer of from 1 to 20,

L is a ligand wherein:

one of the ligands, L, is a compound of formula (a):

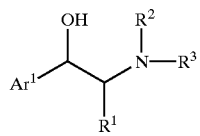

(a)

wherein:

$Ar^1$ is selected from the group consisting of aryl, heteroaryl, cycloalkyl, substituted cycloalkyl, and heterocyclyl wherein each of said $Ar^1$ and $Ar^2$ substituent optionally links the ligand to a linker;

$R^1$ is selected from the group consisting of hydrogen, alkyl, and substituted alkyl, or $R^1$ is a covalent bond linking the ligand to a linker;

$R^2$ and $R^3$ are independently selected from the group consisting of hydrogen, alkyl, acyl, and substituted alkyl, or $R^2$ and $R^3$ are a covalent bond linking the ligand to a linker; and the other ligands are independently selected from a compound of formula (b):

—Q—$Ar^2$ (b)

wherein:

$Ar^2$ is selected from the group consisting of aryl, heteroaryl, cycloalkyl, substituted cycloalkyl, and heterocyclyl;

Q is a covalent bond, or a substituted alkylene group wherein one or more of the carbon atoms in said substituted alkylene group is optionally replaced by a substituent selected from —$NR^a$— (where $R^a$ is hydrogen, alkyl, acyl, or a covalent bond linking the ligand to a linker), —O—, —S(O)$_n$ (where n is an integer of from 0 to 2), —CO—, —$PR^b$— (where $R^b$ is alkyl), —P(O)$_2$—, and —O—P(O)O— and links the ligand to a linker;

each linker, X, in the multibinding compound of Formula (I) independently has the formula:

—$X^a$—Z—($Y^a$—Z)$_m$—$X^a$— wherein:

m is an integer of from 0 to 20;

$X^a$ at each separate occurrence is selected from the group consisting of —O—, —S—, —NR—, —C(O)—, —C(O)O—, —OC(O)—, —C(O)NR—, —NRC(O)—, C(S), —C(S)O—, —C(S)NR—, —NRC(S)—, or a covalent bond where R is as defined below;

Z at each separate occurrence is selected from the group consisting of alkylene, substituted alkylene, alkenylene, substituted alkenylene, alkynylene, substituted alkynylene, or a covalent bond;

each $Y^a$ at each separate occurrence is selected from the group consisting of —O—, —C(O)—, —OC (O)—, —C(O)O—, —NR—, —S(O)n—, —C(O)
NR'—, —NR'C(O)—, —NR'C(O)NR'—, —NR'C
(S)NR'—, —C(=NR')—NR'—, —NR'—C
(=NR')—, —OC(O)—NR'—, —NR'—C(O)—
O—, —N=C($X^a$)—NR'—, —NR'C($X^a$)
=N—, —P(O)(OR')—O—, —O—P(O)(OR')—,
—S(O)$_n$CR'R"—, —S(O)$_n$—NR'—, —NR'—S
(O)$_n$—, and a covalent bond; where n is 0, 1 or 2;
and R, R' and R" at each separate occurrence are
selected from the group consisting of hydrogen,
alkyl, substituted alkyl, cycloalkyl, substituted
cycloalkyl, alkenyl, substituted alkenyl,
cycloalkenyl, substituted cycloalkenyl, alkynyl,
substituted alkynyl, aryl, heteroaryl, and hetero-
cyclic provided that $X^a$, $X^b$, and Z are not covalent
bonds at the same time; and pharmaceutically acceptable salts thereof provided that:
  (i) when Q is a 2-hydroxyethylamino group then the
  linker is not alkylene or —C(O)-alkylene-C(O)—; and
  (ii) when Q, $X^a$, and $X^b$ are covalent bonds then Z is not
  alkylene.

In still another aspect, this invention provides a method of
treating diseases mediated by a β2 adrenergic receptor in a
mammal, said method comprising administering to said
mammal a therapeutically effective amount of a pharmaceu-
tical composition comprising a pharmaceutically acceptable
carrier and a multibinding compound of Formula (I):

   (I)

wherein:
  p is an integer of from 2 to 10;
  q is an integer of from 1 to 20,
  L is a ligand wherein:
    one of the ligands, L, is a compound of formula (a):

   (a)

wherein:
    $Ar^1$ is selected from the group consisting of aryl,
    heteroaryl, cycloalkyl, substituted cycloalkyl, and
    heterocyclyl wherein each of said $Ar^1$ and $Ar^2$
    substituent optionally links the ligand to a linker;
    $R^1$ is selected from the group consisting of hydrogen,
    alkyl, and substituted alkyl, or $R^1$ is a covalent
    bond linking the ligand to a linker;
    $R^2$ and $R^3$ are independently selected from the group
    consisting of hydrogen, alkyl, acyl, and substi-
    tuted alkyl, or $R^2$ and $R^3$ are a covalent bond
    linking the ligand to a linker; and
  the other ligands are independently selected from a
  compound of formula (b):

   (b)

wherein:
    $Ar^2$ is selected from the group consisting of aryl,
    heteroaryl, cycloalkyl, substituted cycloalkyl, and
    heterocyclyl;
    Q is a covalent bond, or a substituted alkylene group
    wherein one or more of the carbon atoms in said
    substituted alkylene group is optionally replaced by a substituent selected from —$NR^a$— (where $R^a$
is hydrogen, alkyl, acyl, or a covalent bond linking
the ligand to a linker), —O—, —S(O)$_n$ (where n
is an integer of from 0 to 2), —CO—, —$PR^b$—
(where $R^b$ is alkyl), —P(O)$_2$—, and —O—P(O)
O— and links the ligand to a linker;
  each linker, X, in the multibinding compound of For-
  mula (I) independently has the formula:

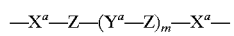

wherein:
    m is an integer of from 0 to 20;
    $X^a$ at each separate occurrence is selected from the
    group consisting of —O—, —S—, —NR—,
    —C(O)—, —C(O)O—, —OC(O)—, —C(O)
    NR—, —NRC(O)—, C(S), —C(S)O—, —C(S)
    NR—, —NRC(S)—, or a covalent bond where R
    is as defined below;
    Z at each separate occurrence is selected from the
    group consisting of alkylene, substituted alkylene,
    alkenylene, substituted alkenylene, alkynylene,
    substituted alkynylene, or a covalent bond;
    each $Y^a$ at each separate occurrence is selected from
    the group consisting of —O—, —C(O)—, —OC
    (O)—, —C(O)O—, —NR—, —S(O)n—, —C(O)
    NR'—, —NR'C(O)—, —NR'C(O)NR'—, —NR'C
    (S)NR'—, —C(=NR')—NR'—, —NR'—C
    (=NR')—, —OC(O)—NR'—, —NR'—C(O)—
    O—, —N=C($X^a$)—NR'—, —NR'—
    C($X^a$)=N—, —P(O)(OR')—O—, —O—P(O)
    (OR')—, —S(O)$_n$CR'R"—, —S(O)$_n$—NR'—,
    —NR'—S(O)$_n$—, and a covalent bond; where n is
    0, 1 or 2; and R, R' and R" at each separate
    occurrence are selected from the group consisting
    of hydrogen, alkyl, substituted alkyl, cycloalkyl,
    substituted cycloalkyl, alkenyl, substituted
    alkenyl, cycloalkenyl, substituted cycloalkenyl,
    alkynyl, substituted alkynyl, aryl, heteroaryl, and
    heterocyclic provided that $X^a$, $X^b$, and Z are not
    covalent bonds at the same time; and
pharmaceutically acceptable salts thereof provided that:
  (i) when a Q is 2-hydroxyethylamino group then the
  linker is not alkylene or —C(O)-alkylene-C(O)—; and
  (ii) when Q, $X^a$, and $X^b$ are covalent bonds then Z is not
  alkylene.

In still another aspect, this invention is directed to general
synthetic methods for generating large libraries of diverse
multimeric compounds which multimeric compounds are
candidates for possessing multibinding properties for β2
adrenergic receptor. The diverse multimeric compound
libraries provided by this invention are synthesized by
combining a linker or linkers with a ligand or ligands to
provide for a library of multimeric compounds wherein the
linker and ligand each have complementary functional
groups permitting covalent linkage. The library of linkers is
preferably selected to have diverse properties such as
valency, linker length, linker geometry and rigidity, hydro-
philicity or hydrophobicity, amphiphilicity, acidity, basicity
and polarization. The library of ligands is preferably selected
to have diverse attachment points on the same ligand,
different functional groups at the same site of otherwise the
same ligand, and the like.

This invention is also directed to libraries of diverse
multimeric compounds which multimeric compounds are
candidates for possessing multibinding properties for β2
adrenergic receptor. These libraries are prepared via the methods described above and permit the rapid and efficient evaluation of what molecular constraints impart multibinding properties to a ligand or a class of ligands targeting a receptor.

Accordingly, in one of its method aspects, this invention is directed to a method for identifying multimeric ligand compounds possessing multibinding properties for β2 adrenergic receptor which method comprises:

(a) identifying a ligand or a mixture of ligands wherein each ligand contains at least one reactive functionality;

(b) identifying a library of linkers wherein each linker in said library comprises at least two functional groups having complementary reactivity to at least one of the reactive functional groups of the ligand;

(c) preparing a multimeric ligand compound library by combining at least two stoichiometric equivalents of the ligand or mixture of ligands identified in (a) with the library of linkers identified in (b) under conditions wherein the complementary functional groups react to form a covalent linkage between said linker and at least two of said ligands; and (d) assaying the multimeric ligand compounds produced in (c) above to identify multimeric ligand compounds possessing multibinding properties for β2 adrenergic receptor.

In another of its method aspects, this invention is directed to a method for identifying multimeric ligand compounds possessing multibinding properties for β2 adrenergic receptor which method comprises:

(a) identifying a library of ligands wherein each ligand contains at least one reactive functionality;

(b) identifying a linker or mixture of linkers wherein each linker comprises at least two functional groups having complementary reactivity to at least one of the reactive functional groups of the ligand;

(c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands; and (d) assaying the multimeric ligand compounds produced in (c) above to identify multimeric ligand compounds possessing multibinding properties for β2 adrenergic receptor.

The preparation of the multimeric ligand compound library is achieved by either the sequential or concurrent combination of the two or more stoichiometric equivalents of the ligands identified in (a) with the linkers identified in (b). Sequential addition is preferred when a mixture of different ligands is employed to ensure heterodimeric or multimeric compounds are prepared. Concurrent addition of the ligands occurs when at least a portion of the multimer comounds prepared are homomultimeric compounds.

The assay protocols recited in (d) can be conducted on the multimeric ligand compound library produced in (c) above, or preferably, each member of the library is isolated by preparative liquid chromatography mass spectrometry (LCMS).

In one of its composition aspects, this invention is directed to a library of multimeric ligand compounds which may possess multivalent properties for β2 adrenergic receptor which library is prepared by the method comprising:

(a) identifying a ligand or a mixture of ligands wherein each ligand contains at least one reactive functionality;

(b) identifying a library of linkers wherein each linker in said library comprises at least two functional groups having complementary reactivity to at least one of the reactive functional groups of the ligand; and (c) preparing a multimeric ligand compound library by combining at least two stoichiometric equivalents of the ligand or mixture of ligands identified in (a) with the library of linkers identified in (b) under conditions wherein the complementary functional groups react to form a covalent linkage between said linker and at least two of said ligands.

In another of its composition aspects, this invention is directed to a library of multimeric ligand compounds which may possess multivalent properties for β2 adrenergic receptor which library is prepared by the method comprising:

(a) identifying a library of ligands wherein each ligand contains at least one reactive functionality;

(b) identifying a linker or mixture of linkers wherein each linker comprises at least two functional groups having complementary reactivity to at least one of the reactive functional groups of the ligand; and (c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands.

In a preferred embodiment, the library of linkers employed in either the methods or the library aspects of this invention is selected from the group comprising flexible linkers, rigid linkers, hydrophobic linkers, hydrophilic linkers, linkers of different geometry, acidic linkers, basic linkers, linkers of different polarization and amphiphilic linkers. For example, in one embodiment, each of the linkers in the linker library may comprise linkers of different chain length and/or having different complementary reactive groups. Such linker lengths can preferably range from about 2 to 100 Å.

In another preferred embodiment, the ligand or mixture of ligands is selected to have reactive functionality at different sites on said ligands in order to provide for a range of orientations of said ligand on said multimeric ligand compounds. Such reactive functionality includes, by way of example, carboxylic acids, carboxylic acid halides, carboxyl esters, amines, halides, isocyanates, vinyl unsaturation, ketones, aldehydes, thiols, alcohols, anhydrides, and precursors thereof. It is understood, of course, that the reactive functionality on the ligand is selected to be complementary to at least one of the reactive groups on the linker so that a covalent linkage can be formed between the linker and the ligand.

In other embodiments, the multimeric ligand compound is homomeric (i.e., each of the ligands is the same, although it may be attached at different points) or heterodimeric (i.e., at least one of the ligands is different from the other ligands).

In addition to the combinatorial methods described herein, this invention provides for an iterative process for rationally evaluating what molecular constraints impart multibinding properties to a class of multimeric compounds or ligands targeting a receptor. Specifically, this method aspect is directed to a method for identifying multimeric ligand compounds possessing multibinding properties for β2 adrenergic receptor which method comprises:

(a) preparing a first collection or iteration of multimeric compounds which is prepared by contacting at least two stoichiometric equivalents of the ligand or mixture of ligands which target a receptor with a linker or mixture of linkers wherein said ligand or mixture of ligands comprises at least one reactive functionality and said linker or mixture of linkers comprises at least two functional groups having complementary reactivity to at least one of the reactive functional groups of the ligand wherein said contacting is conducted under conditions wherein the complementary functional groups react to form a covalent linkage between said linker and at least two of said ligands;

(b) assaying said first collection or iteration of multimeric compounds to assess which if any of said multimeric compounds possess multibinding properties for β2 adrenergic receptor;

(c) repeating the process of (a) and (b) above until at least one multimeric compound is found to possess multibinding properties for β2 adrenergic receptor;

(d) evaluating what molecular constraints imparted multibinding properties to the multimeric compound or compounds for β2 adrenergic receptor found in the first iteration recited in (a)–(c) above;

(e) creating a second collection or iteration of multimeric compounds which elaborates upon the particular molecular constraints imparting multibinding properties to the multimeric compound or compounds found in said first iteration;

(f) evaluating what molecular constraints imparted enhanced multibinding properties to the multimeric compound or compounds found in the second collection or iteration recited in (e) above;

(g) optionally repeating steps (e) and (f) to further elaborate upon said molecular constraints.

Preferably, steps (e) and (f) are repeated at least two times, more preferably at from 2–50 times, even more preferably from 3 to 50 times, and still more preferably at least 5–50 times.

DETAILED DESCRIPTION OF THE INVENTION

Definitions

Figure 1:
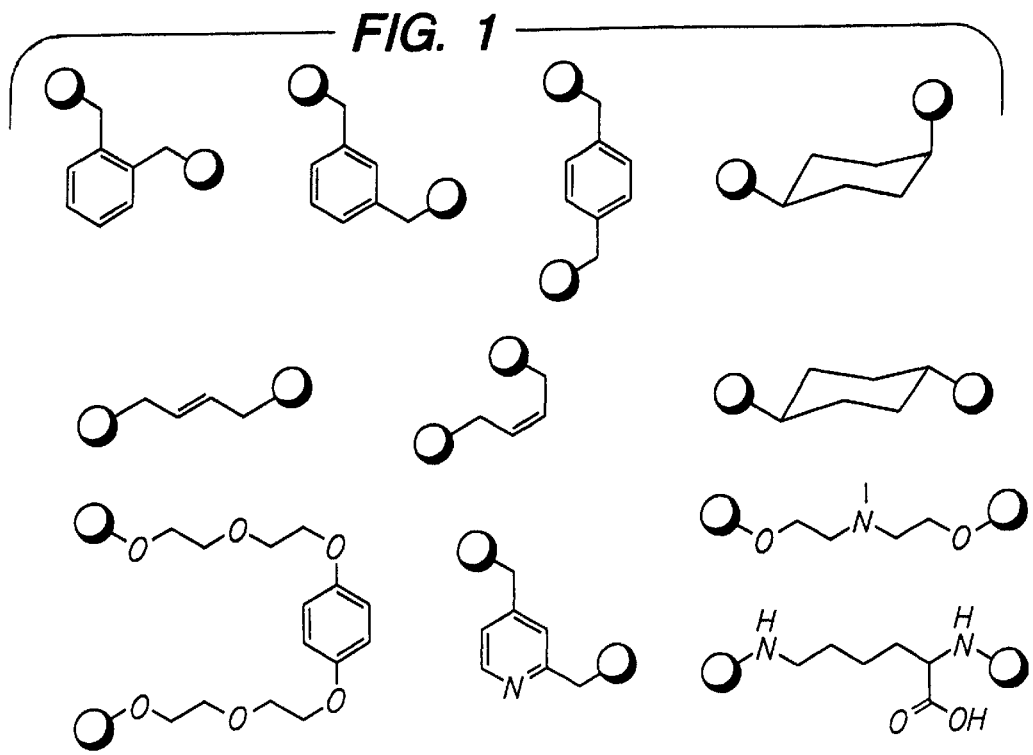
FIG. 1 illustrates examples of multibinding compounds comprising 2 ligands attached in different formats to a linker.

This invention is directed to multibinding compounds which are β2 adrenergic receptor agonists, pharmaceutical compositions containing such compounds and methods for treating diseases mediated by β2 adrenergic receptor in mammals. When discussing such compounds, compositions or methods, the following terms have the following meanings unless otherwise indicated. Any undefined terms have their art recognized meanings.

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. This term is exemplified by groups such as hydroxymethyl, hydroxyethyl, hydroxypropyl, 2-aminoethyl, 3-aminopropyl, 2-methylaminoethyl, 3-dimethylaminopropyl, 2-sulfonamidoethyl, 2-carboxyethyl, and the like.

The term "alkylene" refers to a diradical of a branched or unbranched saturated hydrocarbon chain, preferably having from 1 to 40 carbon atoms, more preferably 1 to 10 carbon atoms and even more preferably 1 to 6 carbon atoms.

This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures.

The term "alkaryl" or "aralkyl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted arnino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. This term is exemplified by groups such as ethenylene (—CH=CH—), the propenylene isomers (e.g., —CH$_2$CH=CH—, —C(CH$_3$)=CH—, and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1–6 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

The term "alkynylene" refers to a diradical of an unsaturated hydrocarbon preferably having from 2 to 40 carbon atoms, more preferably 2 to 10 carbon atoms and even more preferably 2 to 6 carbon atoms and having at least 1 and preferably from 1–6 sites of acetylene (triple bond) unsaturation. Preferred alkynylene groups includeethynylene (—C≡C—), propargylene (—CH$_2$C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl The term "acyl" refers to the groups HC(O)—, alkyl-C(O)—, substituted alkyl-C(O)—, alkenyl-C(O)—, substituted alkenyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, alkenyl, substituted alkenyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "sulfonylamino" refers to the group —NRSO$_2$R$^a$ where R is hydrogen, alkyl, substituted alkyl, aralkyl, or heteroaralkyl, and R$^a$ is alkyl, substituted alkyl, amino, or substituted amino wherein alkyl, substituted alkyl, aralkyl, heteroaralkyl and substituted amino are as defined herein.

The term "aminoacyl" refers to the group —NRC(O)R where each R is independently hydrogen, alkyl, substituted alkyl, alkenyl, substituted alkenyl, amino, substituted amino, aryl, heteroaryl, or heterocyclic wherein alkyl, substituted alkyl, alkenyl, substituted alkenyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). The aryl group may optionally be fused to a heterocyclic or cycloalkyl group. Preferred aryls include phenyl, naphthyl and the like. Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, stilfonylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "amino" refers to the group —NH$_2$.

The term "substituted amino" refers to the group —NRR where each R is independently selected from the group consisting of hydrogen, alkyl, substituted alkyl, acyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl alkynyl are as defined herein.

The term "cycloalkyl" refers to cyclic alkyl groups of from 3 to 20 carbon atoms having a single cyclic ring or multiple condensed rings, said cycloalkyl group may optionally be fused to an aryl or heteroaryl group. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkyl, substituted alkyl, alkenyl, substituted alkenyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkyl, substituted alkyl, alkenyl, substituted alkenyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring). The heteroaryl ring may optionally be fused to a cycloalkyl or heterocyclyl ring. Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO,-heteroaryl and trihalomethyl. Preferred heteroaryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "heteroaryloxy" refers to the group heteroaryl-O—.

The term "heterocycle" or "heterocyclyl" refers to a monoradical saturated unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring and further wherein one, two, or three of the ring carbon atoms may optionally be replaced with a carbonyl group (i.e., a keto group). Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Preferred heterocyclics include morpholino, piperidinyl, and the like.

Examples of heteroaryls and heterocycles include, but are not limited to, pyrrole, thiophene, furan, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, pyrrolidine, piperidine, piperazine, indoline, morpholine, tetrahydrofuranyl, tetrahydrothiophene, and the like as well as N-alkoxy-nitrogen containing heterocycles.

The term "heterocyclooxy" refers to the group heterocyclic-O—.

The term "thioheterocyclooxy" refers to the group heterocyclic-S—.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "spiro-attached cycloalkyl group" refers to a cycloalkyl group joined to another ring via one carbon atom common to both rings.

The term "thiol" refers to the group —SH.

The term "thioalkoxy" or "alkylthio" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "pharmaceutically-acceptable salt" refers to salts which retain the biological effectiveness and properties of the multibinding compounds of this invention and which are not biologically or otherwise undesirable. In many cases, the multibinding compounds of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri (cycloalkyl) amines, substituted cycloalkyl amines, disubstituted cycloalkyl amine, trisubstituted cycloalkyl amines, cycloalkenyl amines, di(cycloalkenyl) amines, tri (cycloalkenyl) amines, substituted cycloalkenyl amines, disubstituted cycloalkenyl amine, trisubstitutedcycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(isopropyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically-acceptable cation" refers to the cation of a pharmaceutically-acceptable salt.

The term "library" refers to at least 3, preferably from $10^2$ to $10^9$ and more preferably from $10^2$ to $10^4$ multimeric compounds. Preferably, these compounds are prepared as a multiplicity of compounds in a single solution or reaction mixture which permits facile synthesis thereof. In one embodiment, thelibrary of multimeric compounds can be directly assayed for multibinding properties. In another embodiment, each member of the library of multimeric compounds is first isolated and, optionally, characterized. This member is then assayed for multibinding properties.

The term "collection" refers to a set of multimeric compounds which are prepared either sequentially or concurrently (e.g., combinatorially). The collection comprises at least 2 members; preferably from 2 to $10^9$ members and still more preferably from 10 to $10^4$ members.

The term "multimeric compound" refers to compounds comprising from 2 to 10 ligands covalently connected through at least one linker which compounds may or may not possess multibinding properties (as defined herein).

The term "pseudohalide" refers to functional groups which react in displacement reactions in a manner similar to a halogen. Such functional groups include, by way of example, mesyl, tosyl, azido and cyano groups.

The term "protecting group" or "blocking group" refers to any group which when bound to one or more hydroxyl, thiol, amino or carboxyl groups of the compounds (including intermediates thereof) prevents reactions from occurring at these groups and which protecting group can be removed by conventional chemical or enzymatic steps to reestablish the hydroxyl, thiol, amino or carboxyl group (See., T. W. Greene and P. G. H. Wuts, "*Protective Groups in Organic Synthesis*", $2^{nd}$ Ed.). The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product.

Preferred removable thiol blocking groups include disulfide groups, acyl groups, benzyl groups, and the like.

Preferred removable amino blocking groups include conventional substituents such as t-butyoxycarbonyl (t-BOC), benzyloxycarbonyl (CBZ), fluorenylmethoxy-carbonyl (FMOC), allyloxycarbonyl (ALOC), and the like which can be removed by conventional conditions compatible with the nature of the product.

Preferred carboxyl protecting groups include esters such as methyl, ethyl, propyl, t-butyl etc. which can be removed by mild conditions compatible with the nature of the product.

The term "optional" or "optionally" means that the subsequently described event, circumstance or substituent may or may not occur, and that the description includes instances where said event or circumstance occurs and instances where it does not.

The term "ligand" or "ligands" as used herein denotes a compound that is a binding partner for a β2 adrenergic receptor and is bound thereto by complementarity. Preferred ligands are those that are either β2 adrenergic receptor agonist or antagonist. The specific region or regions of the ligand that is (are) recognized by the receptor is designated as the "ligand domain". A ligand may be either capable of binding to the receptor by itself, or may require the presence of one or more non-ligand components for binding (e.g., $Ca^{+2}$, $Mg^{+2}$ or a water molecule is required for the binding of a ligand to various ligand binding sites). Examples of ligands useful in this invention are described herein. Those skilled in the art will appreciate that portions of the ligand structure that are not essential for specific molecular recognition and binding activity may be varied substantially, replaced or substituted with unrelated structures (for example, with ancillary groups as defined below) and, in some cases, omitted entirely without affecting the binding interaction. The primary requirement for a ligand is that it has a ligand domain as defined above. It is understood that the term ligand is not intended to be limited to compounds known to be useful in binding to β2 adrenergic receptor (e.g., known drugs). Those skilled in the art will understand that the term ligand can equally apply to a molecule that is not normally associated with β2 adrenergic receptor binding properties. In addition, it should be noted that ligands that exhibit marginal activity or lack useful activity as monomers can be highly active as multivalent compounds because of the benefits conferred by multivalency.

The term "ligand" or "ligands" as used herein is intended to include the racemic forms of the ligands as well as individual enantiomers and diasteromers and non-racemic mixtures thereof.

The term "multibinding compound or agent" refers to a compound that is capable of multivalency, as defined below, and which has 2–10 ligands covalently bound to one or more linkers. In all cases, each ligand and linker in the multibinding compound is independently selected such that the multibinding compound includes both symmetric compounds (i.e., where each ligand as well as each linker is identical) and asymmetric compounds((i.e., where at least one of the ligands is different from the other ligand(s) and/or at least one linker is different from the other linker(s)). Multibinding compounds provide a biological and/or therapeutic effect greater than the aggregate of unlinked ligands equivalent thereto which are made available for binding. That is to say that the biological and/or therapeutic effect of the ligands attached to the multibinding compound is greater than that achieved by the same amount of unlinked ligands made available for binding to the ligand binding sites (receptors). The phrase "increased biological or therapeutic effect" includes, for example: increased affinity, increased selectivity for target, increased specificity for target, increased potency, increased efficacy, decreased toxicity, improved duration of activity or action, increased ability to kill cells such as fungal pathogens, cancer cells, etc., decreased side effects, increased therapeutic index, improved bioavailibity, improved pharmacokinetics, improved activity spectrum, and the like. The multibinding compounds of this invention will exhibit at least one and preferably more than one of the above-mentioned affects.

Furthermore, the multibinding compound of the present invention can either be composed of ligands that are known to be β2 adrenergic receptor agonists or they can be a composed of ligands that are known to be β2 adrenergic receptor agonists and β2 adrenergic receptor antagonists provided that they exhibit an overall β2 adrenergic receptor agonistic activity.

The term "univalency" as used herein refers to a single binding interaction between one ligand as defined herein with one ligand binding site as defined herein. It should be noted that a compound having multiple copies of a ligand (or ligands) exhibit univalency when only one ligand is interacting with a ligand binding site. Examples of univalent interactions are depicted below.

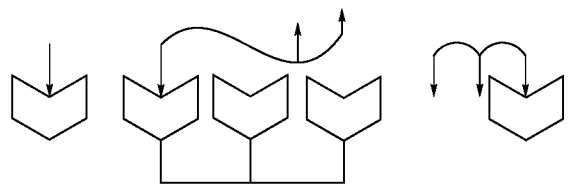

The term "multivalency" as used herein refers to the concurrent binding of from 2 to 10 linked ligands (which may be the same or different) and two or more corresponding receptors (ligand binding sites) which may be the same or different.

For example, two ligands connected through a linker that bind concurrently to two ligand binding sites would be considered as bivalency; three ligands thus connected would be an example of trivalency. An example of trivalent binding, illustrating a multibinding compound bearing three ligands versus a monovalent binding interaction, is shown below:

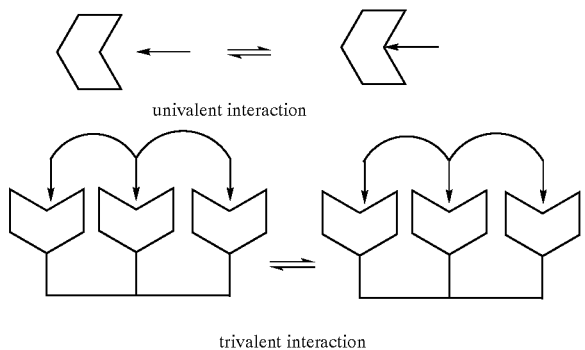

univalent interaction trivalent interaction

It should be understood that not all compounds that contain multiple copies of a ligand attached to a linker or to linkers necessarily exhibit the phenomena of multivalency, i.e., that the biological and/or therapeutic effect of the multibinding agent is greater than the sum of the aggregate of unlinked ligands made available for binding to the ligand binding site (receptor). For multivalency to occur, the ligands that are connected by a linker or linkers have to be presented to their ligand binding sites by the linker(s) in a specific manner in order to bring about the desired ligand-orienting result, and thus produce a multibinding event.

The term "potency" refers to the minimum concentration at which a ligand is able to achieve a desirable biological or therapeutic effect. The potency of a ligand is typically proportional to its affinity for its ligand binding site. In some cases, the potency may be non-linearly correlated with its affinity. In comparing the potency of two drugs, e.g., a multibinding agent and the aggregate of its unlinked ligand, the dose-response curve of each is determined under identical test conditions (e.g., in an in vitro or in vivo assay, in an appropriate animal model such a human patient). The finding that the multibinding agent produces an equivalent biological or therapeutic effect at a lower concentration than the aggregate unlinked ligand is indicative of enhanced potency.

The term "selectivity" or "specificity" is a measure of the binding preferences of a ligand for different ligand binding sites (receptors). The selectivity of a ligand with respect to its target ligand binding site relative to another ligand binding site is given by the ratio of the respective values of $K_d$ (i.e., the dissociation constants for each ligand-receptor complex) or, in cases where a biological effect is observed below the $K_d$, the ratio of the respective $EC_{50}$'s (i.e., the concentrations that produce 50% of the maximum response for the ligand interacting with the two distinct ligand binding sites (receptors)).

The term "ligand binding site" denotes the site on the β-adrenergic receptor that recognizes a ligand domain and provides a binding partner for the ligand. The ligand binding site may be defined by monomeric or multimeric structures. This interaction may be capable of producing a unique biological effect, for example, agonism, antagonism, and modulatory effects, or it may maintain an ongoing biological event, and the like.

It should be recognized that the ligand binding sites of the receptor that participate in biological multivalent binding interactions are constrained to varying degrees by their intra- and inter-molecular associations. For example, ligand binding sites may be covalently joined to a single structure, noncovalently associated in a multimeric structure, embedded in a membrane or polymeric matrix. and so on and therefore have less translational and rotational freedom than if the same structures were present as monomers in solution.

The terms "agonism" and "antagonism" is well known in the art. The term "modulatory effect" refers to the ability of the ligand to change the activity of an agonist or antagonist through binding to a ligand binding site.

The term "inert organic solvent" or "inert solvent" means a solvent which is inert under the conditions of the reaction being described in conjunction therewith including, by way of example only, benzene, toluene, acetonitrile, tetrahydrofuran, dimethylformamide, chloroform, methylene chloride, diethyl ether, ethyl acetate, acetone, methylethyl ketone, methanol, ethanol, propanol, isopropanol, t-butanol, dioxane, pyridine, and the like. Unless specified to the contrary, the solvents used in the reactions described herein are inert solvents.

The term "treatment" refers to any treatment of a pathologic condition in a mammal, particularly a human, and includes:

(i) preventing the pathologic condition from occurring in a subject which may be predisposed to the condition but has not yet been diagnosed with the condition and, accordingly, the treatment constitutes prophylactic treatment for the disease condition;

(ii) inhibiting the pathologic condition, i.e., arresting its development;

(iii) relieving the pathologic condition, i.e., causing regression of the pathologic condition; or (iv) relieving the conditions mediated by the pathologic condition.

The term "pathologic condition which is modulated by treatment with a ligand" covers all disease states (i.e., pathologic conditions) which are generally acknowledged in the art to be usefully treated with a ligand for the β2-adrenergic receptor in general, and those disease states which have been found to be usefully treated by a specific multibinding compound of our invention. Such disease states include, by way of example only, the treatment of a mammal afflicted with asthma, chronic bronchitis, and the like.

The term "therapeutically effective amount" refers to that amount of multibinding compound which is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "linker", identified where appropriate by the symbol 'X' refers to a group or groups that covalently attaches from 2 to 10 ligands (as identified above) in a manner that provides for a compound capable of multivalency. Among other features, the linker is a ligand-orienting entity that permits attachment of at least two copies of a ligand (which may be the same or different) thereto. In some cases, the linker may itself be biologically active. The term "linker" does not, however, extend to cover solid inert supports such as beads, glass particles, fibers, and the like. But it is understood that the multibinding compounds of this invention can be attached to a solid support if desired. For example, such attachment to solid supports can be made for use in separation and purification processes and similar applications.

The extent to which multivalent binding is realized depends upon the efficiency with which the linker or linkers that joins the ligands presents these ligands to the array of available ligand binding sites. Beyond presenting these ligands for multivalent interactions with ligand binding sites, the linker or linkers spatially constrains these interactions to occur within dimensions defined by the linker or linkers. Thus, the structural features of the linker (valency, geometry, orientation, size, flexibility, chemical composition, etc.) are features of multibinding agents that play an important role in determining their activities.

The linkers used in this invention are selected to allow multivalent binding of ligands to the ligand binding sites of a β2 adrenergic receptor, whether such sites are located interiorly, both interiorly and on the periphery of the receptor structure, or at any intermediate position thereof.

I. Representative bivalent multibinding compounds of Formula (I) and/or (II) where, in Formula (I), $Ar^1$ and $Ar^2$ are 4-hydroxy-3-hydroxymethylphenyl, Q is 2-hydroxyethylamino, $R^1$ and $R^2$ are hydrogen and linker, X, is defined as defined below and, in Formula (II), $Ar^1$ and $Ar^2$ are both 4-hydroxy-3-hydroxymethylphenyl and linker, X, is as defined below are:

$Ar^1$ is aryl, more preferably $Ar^1$ is:
(a) a phenyl ring of formula (c):

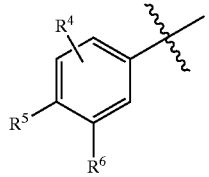

(c)

wherein:
$R^4$ is hydrogen, alkyl, halo, or alkoxy, preferably hydrogen, methyl, fluoro, chloro, or methoxy;
$R^5$ is hydrogen, hydroxy, halo, halo, amino, or —$NHSO_2R^a$ where $R^a$ is alkyl, preferably hydrogen, hydroxy, fluoro, chloro, amino, or —$NHSO_2CH_3$; and
$R^6$ is hydrogen, halo, hydroxy, alkoxy, substituted alkyl, sulfonylamino, aminoacyl, or acylamino;

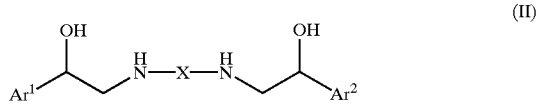

| Cpd. # | Stereochem. at *C | X |
|---|---|---|
| 1 | RS | —$(CH_2)_3$—O—[$(CH_2)_2O$]$_{73}$—$(CH_2)_3$— |
| 2 | RS | —$(CH_2)_3$—O—[$(CH_2)_2O$]$_{74}$—$(CH_2)_3$— |
| 3 | RS | —$CH(CH_3)CH_2$—[O—$CH(CH_3)CH_2$—]n-O—$CH_2$—$CH(CH_3)$— n = 4–9 |
| 4 | RS | —$(CH_2)_2$—O—$(CH_2)_2$—O—$(CH_2)_2$— |
| 5 | RS | —$(CH_2)_3$—O—$(CH_2)_2$—O—$(CH_2)_2$—O—$(CH_2)_3$— |
| 6 | RS | —$(CH_2)_3$—O—$(CH_2)_4$—O—$(CH_2)_3$— |
| 7 | RS | —$(CH_2)_6$—O—$(CH_2)_6$— |
| 8 | RS | —$(CH_2)_6$—O—$(CH_2)_6$—O—$(CH_2)_6$— |

PREFERRED EMBODIMENTS

While the broadest definition of this invention is set forth in the Summary of the Invention, certain compounds of Formula (I) are preferred.

A) A preferred group is a bivalent multibinding compound of Formula (II):

(II)

$Ar^1$—CH(OH)—CH$_2$—NH—X—NH—CH$_2$—CH(OH)—$Ar^2$ (i) Within this group (A), a more preferred group of compounds is that wherein:

preferably hydrogen, chloro, fluoro, hydroxy, methoxy, hydroxymethyl, —$CH_2SO_2CH_3$, —$NHSO_2CH_3$, —$NHCHO$, —$CONH_2$, or —$NHCONH_2$.

(ii) Another more preferred group of compounds within group (A) is that wherein:
$Ar^1$ is heteroaryl, more preferably $Ar^1$ is 2,8-dihydroxyquinolin-5-yl or 3-bromoisoxazol-5-yl.

(iii) Yet another more preferred group of compounds within group (A) is that wherein:
$Ar^1$ is heterocyclyl, more preferably $Ar^1$ is heterocyclyl fused to an aryl ring, most preferably 6-fluorochroman-2-yl.

Within this group A(i)–(iii), an even more preferred group of compounds is that wherein:
X is a linker selected from the group consisting of -(alkylene)-O—[(alkylene)-O—]$_n$-(alkylene)- (n is 0, 1–9, 73 or 74).

Within the above preferred, more preferred group of compounds, a particularly preferred group of compounds is that wherein:

(i) $Ar^2$ is same as $Ar^1$ as defined in preferred embodiment (A)(i)–(iii) above.

Another particularly preferred group of compounds is that wherein:

(ii) Ar2 is a phenyl ring of formula (d):

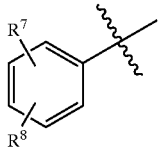

(d)

wherein:

$R^7$ is hydrogen, alkyl, alkenyl, substituted alkyl, halo, alkoxy, substituted alkoxy, hydroxy, aminoacyl, or heteroaryl, preferably hydrogen, methyl, propen-2-yl, fluoro, chloro, methoxy, —CH$_2$CO$_2$Me, hydroxy, —CH$_2$CONH$_2$, —NHCOCH$_3$, imidazol-1-yl, or 1-methyl-4-trifluoromethylimidazol-2-yl; and $R^8$ is hydrogen, halo, alkoxy, substituted alkoxy, acylamino, preferably hydrogen, fluoro, chloro, methoxy, —CH$_2$CO$_2$Me, or —CONH$_2$.

(iii) Yet another particularly preferred group of compounds is that wherein:

$Ar^1$ is naphthyl, pyridyl, benzimidazol-1-yl, indolyl, 2-cyanoindolyl, carbazolyl, 4-methylindanyl, 5-(CH$_3$CO$_2$CH$_2$O—)-1,2,3,4-tetrahydronaphthyl, 1H-2-oxoindole, 2,3,4-trihydrothianaphthalene, 4-hydroxybenzthiazolin-2-one or 4-oxo-2,3-dihydrothianapthalene.

Within the above preferred, more preferred, and particularly preferred groups, even more particularly preferred group is that wherein:

$Ar^1$ is phenyl, 4-hydroxyphenyl, 3,4-dihydroxyphenyl, 3,4-dichlorophenyl, 2-chloro-3,4-dihydroxyphenyl, 2-fluoro-3,4-dihydroxyphenyl, 2-chloro-3,5-dihydroxyphenyl, 2-fluoro-3,5-dihydroxyphenyl, 4-hydroxy-3-methoxyphenyl, 4-hydroxy-3-hydroxymethylphenyl, 4-hydroxy-3-(HCONH—)phenyl, 4-hydroxy-3-(NH$_2$CO—)phenyl, 3-chlorophenyl, 2,5-dimethoxyphenyl, 4-(CH$_3$SO$_2$NH—)-phenyl, 4-hydroxy-3-(CH$_3$SO$_2$CH$_2$—)phenyl, 4-hydroxy-3-(CH$_3$SO$_2$NH—)phenyl, 4-hydroxy-3-(NH$_2$CONH—)phenyl, 3,5-dichloro-4-aminophenyl,

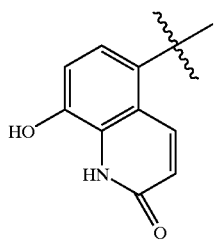 or 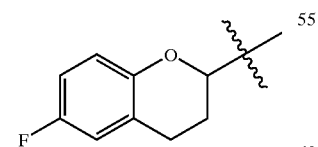

preferably 4-hydroxy-3-hydroxymethylphenyl, 4-hydroxy-3-(HCONH—)phenyl, 3,5-dichloro-4-aminophenyl, or

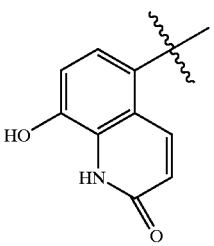

X is —(CH$_2$)$_3$—O—[(CH$_2$)$_2$—O]$_{73}$—(CH$_2$)$_3$—, —(CH$_2$)$_3$—O—[(CH$_2$)$_2$—O]$_{74}$—(CH$_2$)$_3$—, —CH(CH$_3$)CH$_2$—[O—CH(CH$_3$)CH$_2$—]n-O—CH$_2$—CH(CH$_3$)— (n is 4–9), —(CH$_2$)$_2$—O—(CH$_2$)$_2$—O—(CH$_2$)$_2$—, —(CH$_2$)$_3$O—(CH$_2$)$_2$—O—(CH$_2$)$_2$—O—(CH$_2$)$_3$—, —(CH$_2$)—O—(CH$_2$)$_4$—O—(CH$_2$)$_3$—, —(CH$_2$)$_6$O—(CH$_2$)$_6$—, and —(CH$_2$)$_6$—O—(CH$_2$)$_6$—O—(CH$_2$)$_6$—; and $Ar^2$ is:

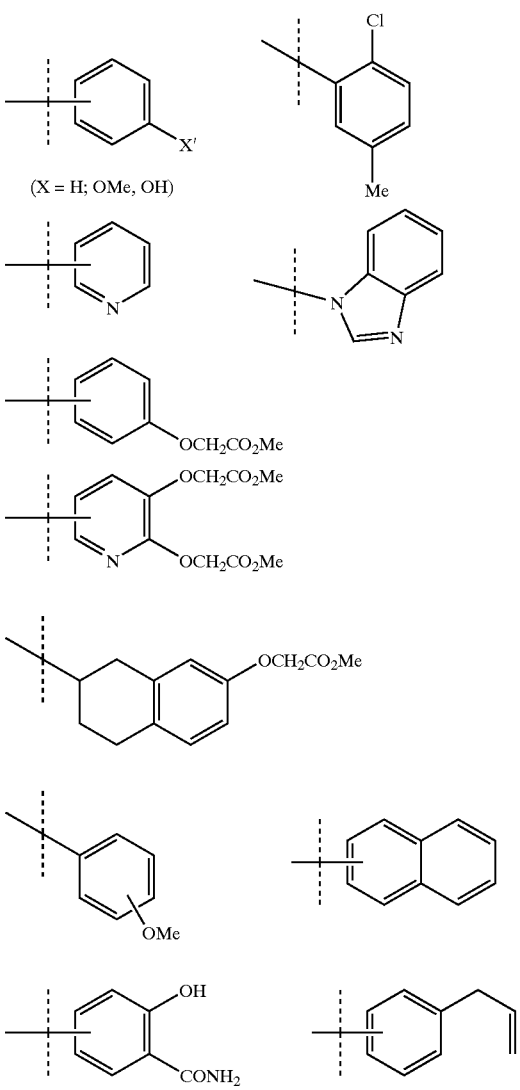

-continued

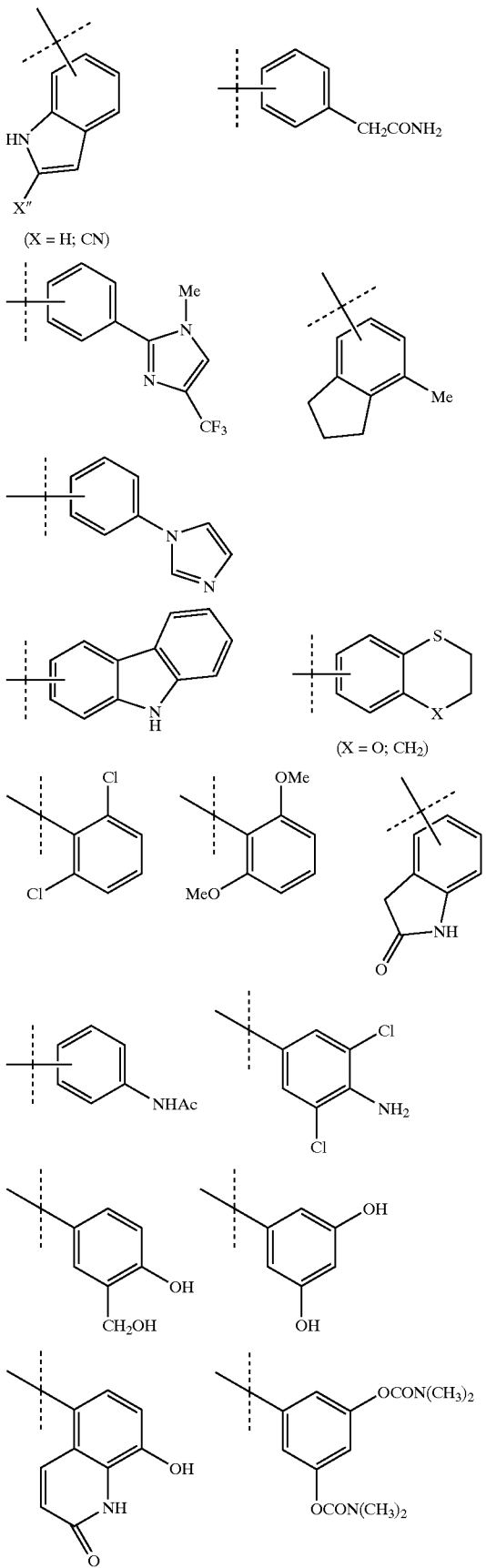

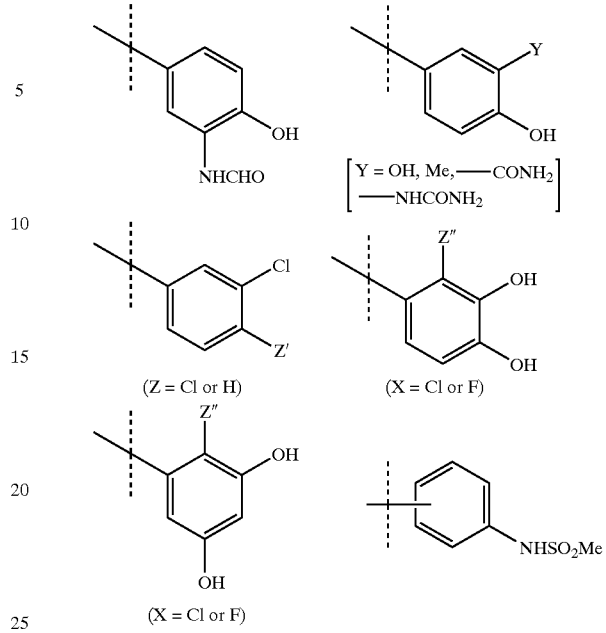

Another preferred group is a bivalent multibinding compound of Formula (III):

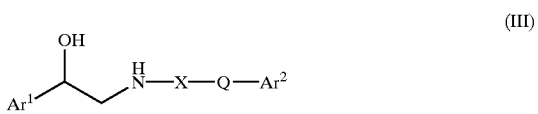

(III)

wherein:

X is a bond;

Q is a substituted alkylene group wherein one or more of the carbon atoms in said substituted alkylene group is optionally replaced by a heteroatom such as —NR$^a$— (where R$^a$ is hydrogen, alkyl, or acyl) or —O—, preferably —NHCH$_2$—CH(OH)—CH$_2$—O—; and Ar$^1$ and Ar$^1$ are as defined in (A) above.

GENERAL SYNTHETIC SCHEME

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1–15 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989).

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Furthermore, it will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Second Edition, Wiley, New York, 1991, and references cited therein.

These schemes are merely illustrative of some methods by which the compounds of this invention can be synthesized, and various modifications to these schemes can be made and will be suggested to one skilled in the art having referred to this disclosure.

Preparation of a Multibinding Compound of Formula (I)

In general, a bivalent multibinding compound of Formula (I) can be prepared as illustrated and described in Schemes A-D below.

A bivalent multibinding compound of Formula (I) can be prepared by covalently attaching the ligands, L, to a linker, X, as shown in Scheme A below.

Scheme A

Method (a)

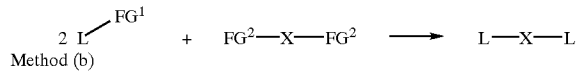

Method (b)

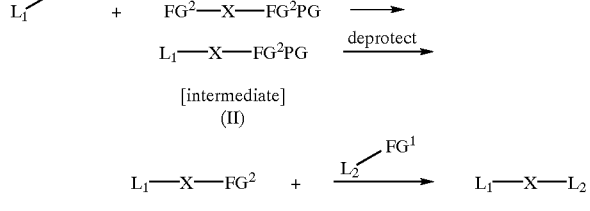

In method (a), a bivalent multibinding compound of Formula (I) is prepared in one step, by covalently attaching the ligands, L, to a linker, X, where $FG^1$ and $FG^2$ represent a functional group such as halo, amino, hydroxy, thio, aldehyde, ketone, carboxy, carboxy derivatives such as acid halide, ester, amido, and the like. This method is preferred for preparing compounds of Formula (I) where both the ligands are identical.

In method (b), the compounds of Formula (I) are prepared in a stepwise manner by covalently attaching one equivalent of a ligand, $L_1$, with a ligand X where where $FG^1$ and $FG^2$ represent a functional group as defined above, and $FG^2PG$ is a protected functional group to give an intermediate of formula (II). Deprotection of the second functional group in (II), followed by reaction with a ligand $L_2$, which may be same or different than ligand $L_1$, then provides a compound of Formula (I). This method is suitable for preparing compounds of Formula (I) where the ligands are the non-identical.

The ligands are covalently attached to the linker using conventional chemical techniques providing for covalent linkage of the ligand to the linker. Reaction chemistries resulting in such linkages are well known in the art and involve the use of complementary functional groups on the linker and ligand as shown in Table I below.

TABLE 1

Representative Complementary Binding Chemistries

| First Reactive Group | Second Reactive Group | Linkage |
|---|---|---|
| carboxyl | amine | amide |
| sulfonyl halide | amine | sulfonamide |
| hydroxyl | alkyl/aryl halide | ether |
| hydroxyl | isocyanate | urethane |
| amine | epoxide | β-hydroxyamine |
| amine | alkyl/aryl halide | alkylamine |
| hydroxyl | carboxyl | ester |
| amine | aldehyde | amine |

Reaction between a carboxylic acid of either the linker or the ligand and a primary or secondary amine of the ligand or the linker in the presence of suitable, well-known activating agents such as dicyclohexylcarbodiimide, results in formation of an amide bond covalently linking the ligand to the linker; reaction between an amine group of either the linker or the ligand and a sulfonyl halide of the ligand or the linker, in the presence of a base such as triethylamine, pyridine, an the like results in formation of a sulfonamide bond covalently linking the ligand to the linker; and reaction between an alcohol or phenol group of either the linker or the ligand and an alkyl or aryl halide of the ligand or the linker in the presence of a base such as triethylamine, pyridine, and the like, results in formation of an ether bond covalently linking the ligand to the linker.

A bivalent multibinding compound of Formula (I) where $Ar^1$ is same as $Ar^2$, Q is 2-hydroxyethylamino, and $R^1$ and $R^2$ are hydrogen can also be prepared from an α,α-dihydroxyacetophenone derivative of formula 1 as shown in Scheme B below.

Scheme B

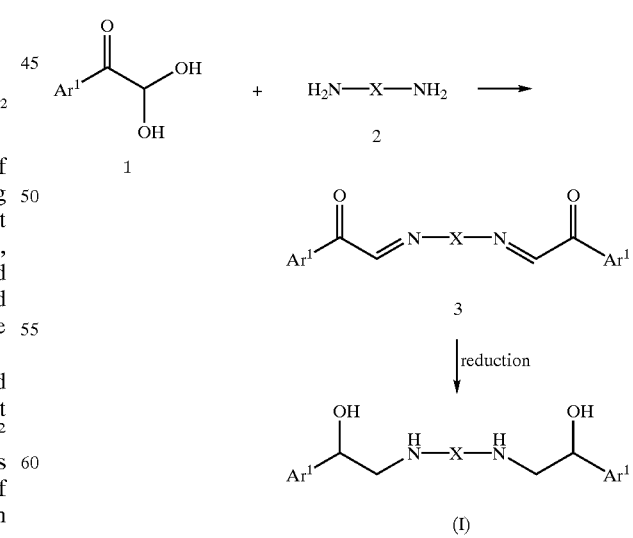

Condensation of an α,α-dihydroxyacetophenone derivative of formula 1 with a diamine of formula 2 in an ethereal solution such as tetrahydrofuran provides an imine of formula 3. Reduction of the imine with a suitable reducing agent such as borane provides a compound of Formula (1). Suitable reaction solvents are tetrahydrofuran, and the like. Compound 1 where $Ar^1$ is phenyl is prepared by heating acetophenone in 48% hydrobromic acid in dimethylsulfoxide.

Compounds of formula 1 can be prepared by methods well known in the art. For example, α,α-dihydroxy-4-hydroxy-3-methoxycarbonylacetophenone can be prepared by heating 5-acetylsalicylic acid methyl ester in 48% hydrobromic acid.

Alternatively, a bivalent multibinding compound of Formula (I) where $Ar^1$ is same as $Ar^2$, Q is 2-hydroxyethylamino, $R^1$ and $R^2$ are hydrogen can be prepared from an epoxide of formula 1 as shown in Scheme C below.

Scheme C

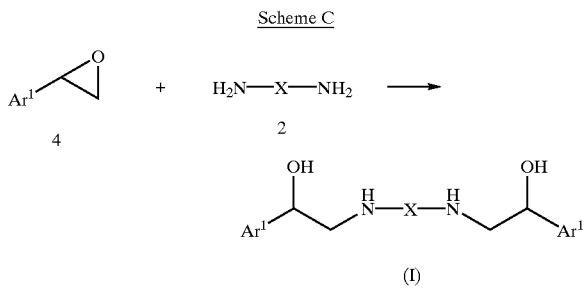

A compound of (I) can be prepared by reacting an epoxide of formula 5 with a diamine of formula 2. Epoxides 4 are either commercially available or they can be prepared by the methods described in Kierstead, R. W. et. al. *J. Med. Chem.* 26, 1561–1569, (1983) or Hett, R. et. al. *Tet. Lett.*35, 9345–9348 (1994).

Another method of preparing a bivalent multibinding compound of Formula (I) where $Ar^1$ is same as $Ar^2$, Q is 2-hydroxyethylamino, $R^1$ and $R^2$ are hydrogen is shown in Scheme D below.

Scheme D

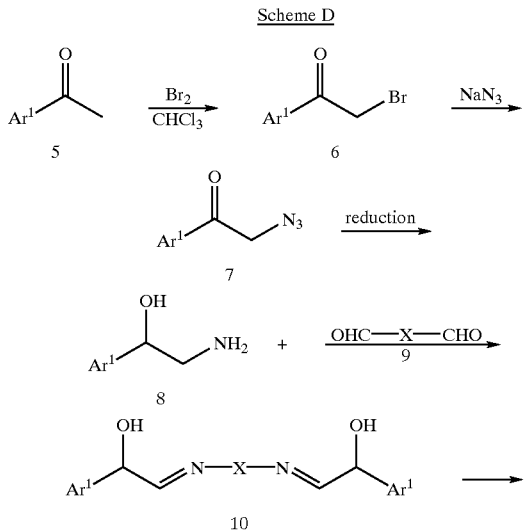

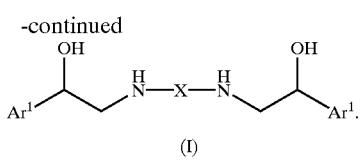

Bromination of an acetophenone derivative of formula 5 with bromine in a halogenated organic solvent such as chloroform provides an α-bromoacetophenone derivative of formula 6. Treatment of 6 with sodium azide followed by reduction of the resulting azide 7 with a suitable reducing agent such as lithium aluminum hydride provides ethanolamine derivative of formula 8. Condensation of 2 equivalents of 8 with a dialdehyde compound 9 provides an imine of formula 10 which is converted to a compound of Formula (1) as described in Scheme A above.

Any compound which is a β2 adrenergic receptor agonist or antagonist provided that the multibinding compound of the Formula (I) acts as a β2 agonist can be used as a ligand in this invention. Typically, a compound selected for use as a ligand will have at least one functional group, such as an amino, hydroxyl, thiol or carboxyl group and the like, which allows the compound to be readily coupled to the linker. Compounds having such functionality are either known in the art or can be prepared by routine modification of known compounds using conventional reagents and procedures.

Linkers can be attached to different positions on the ligand molecule to achieve different orientations of the ligand domains, and thereby facilitate multivalency. While a number of positions on β-adrenergic-modulating ligands are synthetically practical for linking, it is preferred to preserve those ligand substructures which are most important for ligand-receptor binding. At present, the aryl group and the sidechain nitrogen are preferred points of attachment.

It will be apparent to one skilled in the art that the above chemistries are not limited to preparing bivalent multibinding compounds of Formula (I) and can be used to prepare tri-, tetra-, etc., multibinding compounds of Formula (I).

The linker is attached to the ligand at a position that retains ligand domain-ligand binding site interaction and specifically which permits the ligand domain of the ligand to orient itself to bind to the ligand binding site. Such positions and synthetic protocols for linkage are well known in the art. The term linker embraces everything that is not considered to be part of the ligand.

The relative orientation in which the ligand domains are displayed derives from the particular point or points of attachment of the ligands to the linker, and on the framework geometry. The determination of where acceptable substitutions can be made on a ligand is typically based on prior knowledge of structure-activity relationships (SAR) of the ligand and/or congeners and/or structural information about ligand-receptor complexes (e.g., X-ray crystallography, NMR, and the like). Such positions and the synthetic methods for covalent attachment are well known in the art. Following attachment to the selected linker (or attachment to a significant portion of the linker, for example 2–10 atoms of the linker), the univalent linker-ligand conjugate may be tested for retention of activity in the relevant assay.

The linker, when covalently attached to multiple copies of the ligands, provides a biocompatible, substantially non-immunogenic multibinding compound. The biological activity of the multibinding compound is highly sensitive to the valency, geometry, composition, size, flexibility or rigidity, etc. of the linker and, in turn, on the overall structure of the multibinding compound, as well as the presence or absence of anionic or cationic charge, the relative hydrophobicity/hydrophilicity of the linker, and the like on the linker. Accordingly, the linker is preferably chosen to maximize the biological activity of the multibinding compound. The linker may be chosen to enhance the biological activity of the molecule. In general, the linker may be chosen from any organic molecule construct that orients two or more ligands to their ligand binding sites to permit multivalency. In this regard, the linker can be considered as a "framework" on which the ligands are arranged in order to bring about the desired ligand-orienting result, and thus produce a multibinding compound.

For example, different orientations can be achieved by including in the framework groups containing mono- or polycyclic groups, including aryl and/or heteroaryl groups, or structures incorporating one or more carbon-carbon multiple bonds (alkenyl, alkenylene, alkynyl or alkynylene groups). Other groups can also include oligomers and polymers which are branched- or straight-chain species. In preferred embodiments, rigidity is imparted by the presence of cyclic groups (e.g., aryl, heteroaryl, cycloalkyl, heterocyclic, etc.). In other preferred embodiments, the ring is a six or ten member ring. In still further preferred embodiments, the ring is an aromatic ring such as, for example, phenyl or naphthyl.

Different hydrophobic/hydrophilic characteristics of the linker as well as the presence or absence of charged moieties can readily be controlled by the skilled artisan. For example, the hydrophobic nature of a linker derived from hexamethylene diamine ($H_2N(CH_2)_6NH_2$) or related polyamines can be modified to be substantially more hydrophilic by replacing the alkylene group with a poly(oxyalkylene) group such as found in the commercially available "Jeffamines".

Different frameworks can be designed to provide preferred orientations of the ligands. Such frameworks may be represented by using an array of dots (as shown below) wherein each dot may potentially be an atom, such as C, O, N, S, P, H, F, Cl, Br, and F or the dot may alternatively indicate the absence of an atom at that position. To facilitate the understanding of the framework structure, the framework is illustrated as a two dimensional array in the following diagram, although clearly the framework is a three dimensional array in practice:

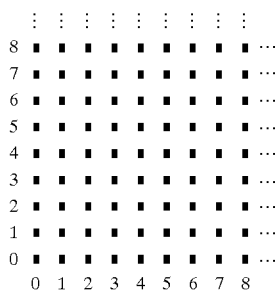

Each dot is either an atom, chosen from carbon, hydrogen, oxygen, nitrogen, sulfur, phosphorus, or halogen, or the dot represents a point in space (i.e., an absence of an atom). As is apparent to the skilled artisan, only certain atoms on the grid have the ability to act as an attachment point for the ligands, namely, C, O, N, S and P.

Atoms can be connected to each other via bonds (single, double or triple bonds with acceptable resonance and tautomeric forms), with regard to the usual constraints of chemical bonding. Ligands may be attached to the framework via single, double or triple bonds (with chemically acceptable tautomeric and resonance forms). Multiple ligand groups (2 to 10) can be attached to the framework such that the minimal, shortest path distance between adjacent ligand groups does not exceed 100 atoms. Preferably, the linker connections to the ligand is selected such that the maximum spatial distance between two adjacent ligands is no more than 100 Å.

An example of a linker as presented by the grid is shown below for a biphenyl construct.

Nodes (1,2), (2,0), (4,4), (5,2), (4,0), (6,2), (7,4), (9,4), (10,2), (9,0), (7,0) all represent carbon atoms. Node (10,0) represents a chlorine atom. All other nodes (or dots) are points in space (i.e., represent an absence of atoms).

Nodes (1,2) and (9,4) are attachment points. Hydrogen atoms are affixed to nodes (2,4), (4,4), (4,0), (2,0), (7,4), (10,2) and (7,0). Nodes (5,2) and (6,2) are connected by a single bond.

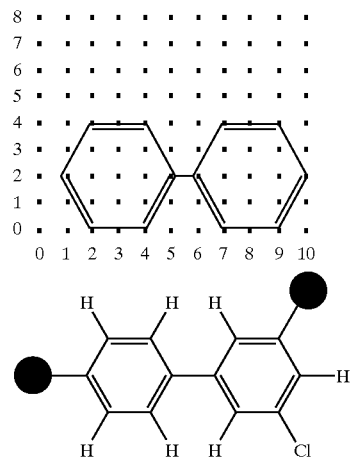

The carbon atoms present are connected by either a single or double bonds, taking into consideration the principle of resonance and/or tautomerism.

The intersection of the framework (linker) and the ligand group, and indeed, the framework (linker) itself can have many different bonding patterns. Examples of acceptable patterns of three contiguous atom arrangements are shown in the following diagram:

| CCC | NCC | OCC | SCC | PCC |
|-----|-----|-----|-----|-----|
| CCN | NCN | OCN | SCN | PCN |
| CCO | NCO | OCO | SCO | PCO |
| CCS | NCS | OCS | SCS | PCS |
| CCP | NCP | OCP | SCP | PCP |
| CNC | NNC | ONC | SNC | PNC |
| CNN | NNN | ONN | SNN | PNN |
| CNO | NNO | ONO | SNO | PNO |
| CNS | NNS | ONS | SNS | PNS |
| CNP | NNP | ONP | SNP | PNP |
| COC | NOC | OOC | SOC | POC |
| COO | NON | OON | SON | PON |
| COC | NOO | OOO | SOO | POO |
| COP | NOP | OOS | SOS | POS |
|     |     | OOP | SOP | POP |
| CSC | NSC |     |     |     |
| CSN | NSN | OSC | SSC | PSC |
| CSO | NSO | OSN | SSN | PSN |
| CSS | NSS | OSO | SSO | PSO |

-continued

| CSP | NSP | OSS | SSS | PSS |
|---|---|---|---|---|
|  |  | OSP | SSP | PSP |
| CPC | NPC |  |  |  |
| CPN | NPN | OPC | SPC | PPC |
| CPO | NPO | OPN | SPN | PPN |
| CPS | NPS | OPO | SPO | PPO |
| CPP | NPP | OPS | SPS | PPS |
|  |  | OPP | SPP | PPP |

One skilled in the art would be able to identify bonding patterns that would produce multivalent compounds. Methods for producing these bonding arrangements are described in March, "Advanced Organic Chemistry", 4th Edition, Wiley-interscience, New York, N.Y. (1992). These arrangements are described in the grid of dots shown in the scheme above. All of the possible arrangements for the five most preferred atoms are shown. Each atom has a variety of acceptable oxidation states. The bonding arrangements underlined are less acceptable and are not preferred.

Examples of molecular structures in which the above bonding patterns could be employed as components of the linker are shown below.

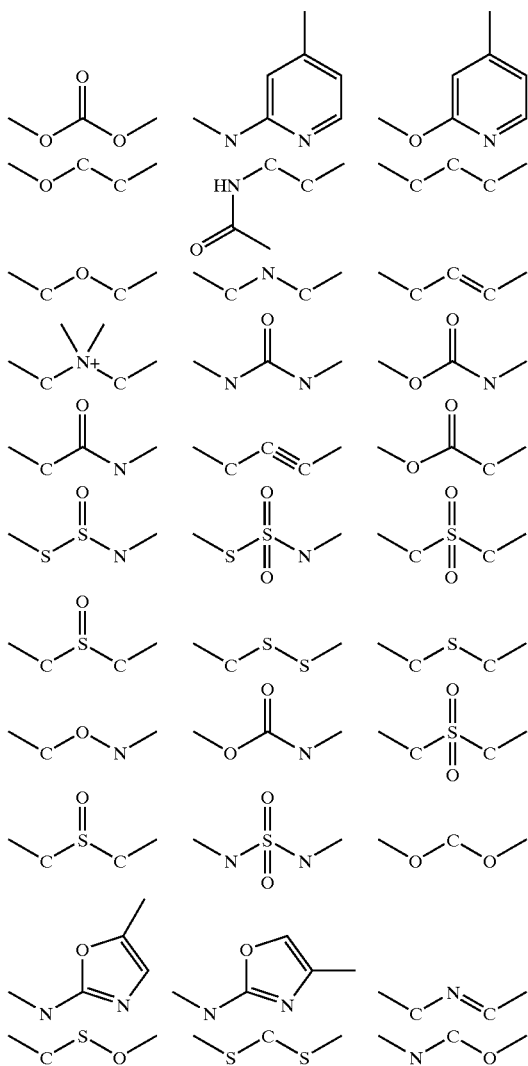

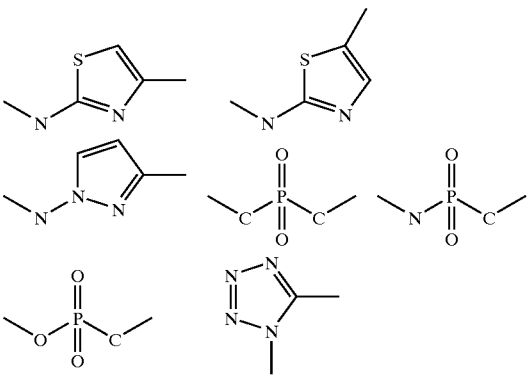

Figure 4:
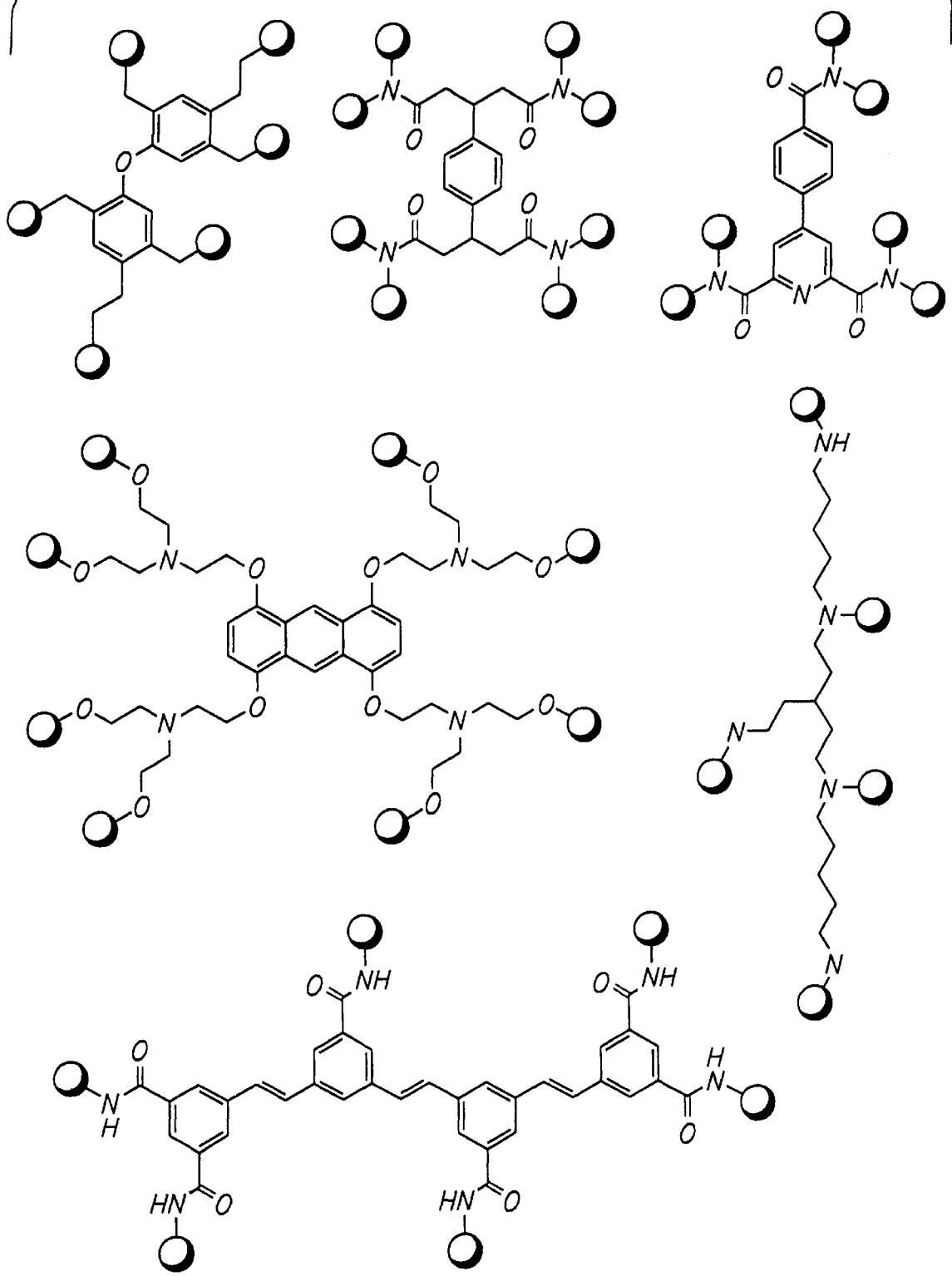
FIG. 4 illustrates examples of multibinding compounds comprising >4 ligands attached in different formats to a linker.

The identification of an appropriate framework geometry and size for ligand domain presentation are important steps in the construction of a multibinding compound with enhanced activity. Systematic spatial searching strategies can be used to aid in the identification of preferred frameworks through an iterative process. FIG. 4 illustrates a useful strategy for determining an optimal framework display orientation for ligand domains. Various other strategies are known to those skilled in the art of molecular design and can be used for preparing compounds of this invention.

As shown in FIG. 1, display vectors around similar central core structures such as a phenyl structure (Panel A) and a cyclohexane structure (Panel B) can be varied, as can the spacing of the ligand domain from the core structure (i.e., the length of the attaching moiety). It is to be noted that core structures other than those shown here can be used for determining the optimal framework display orientation of the ligands. The process may require the use of multiple copies of the same central core structure or combinations of different types of display cores.

Figure 2:
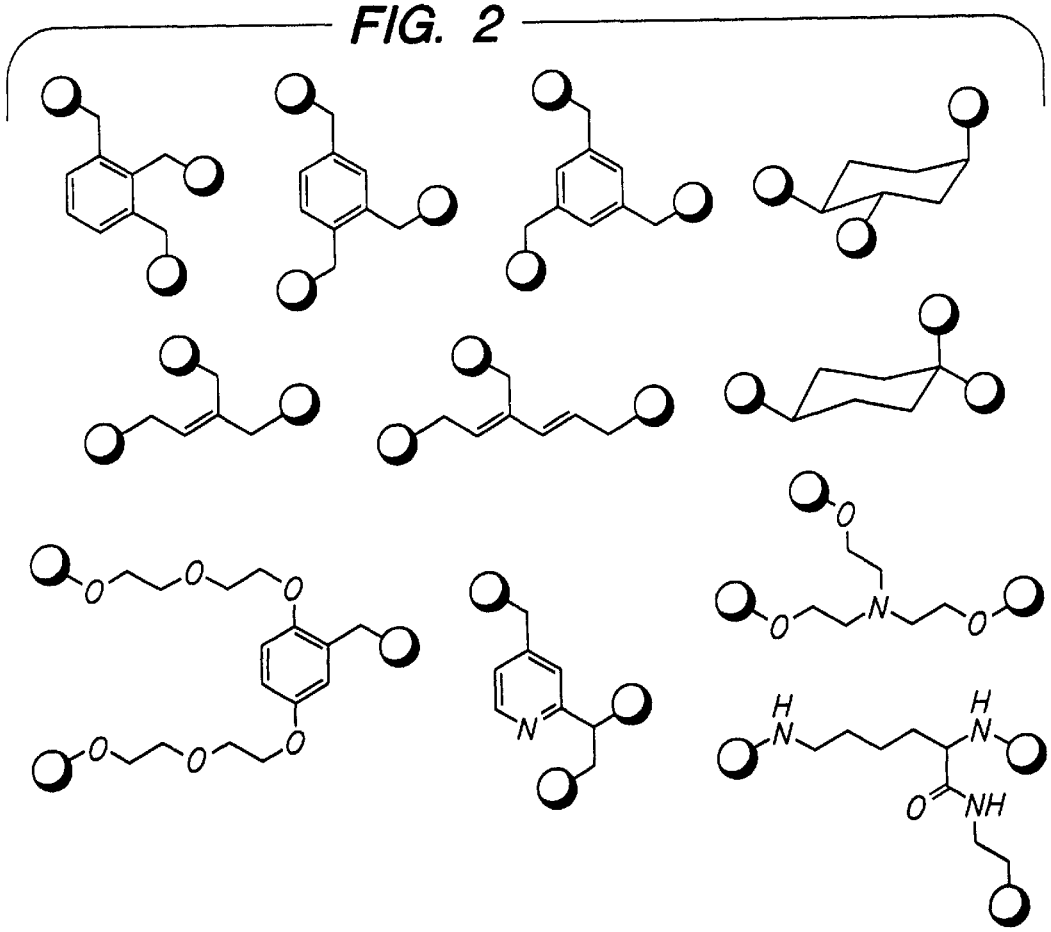
FIG. 2 illustrates examples of multibinding compounds comprising 3 ligands attached in different formats to a linker.
Figure 3:
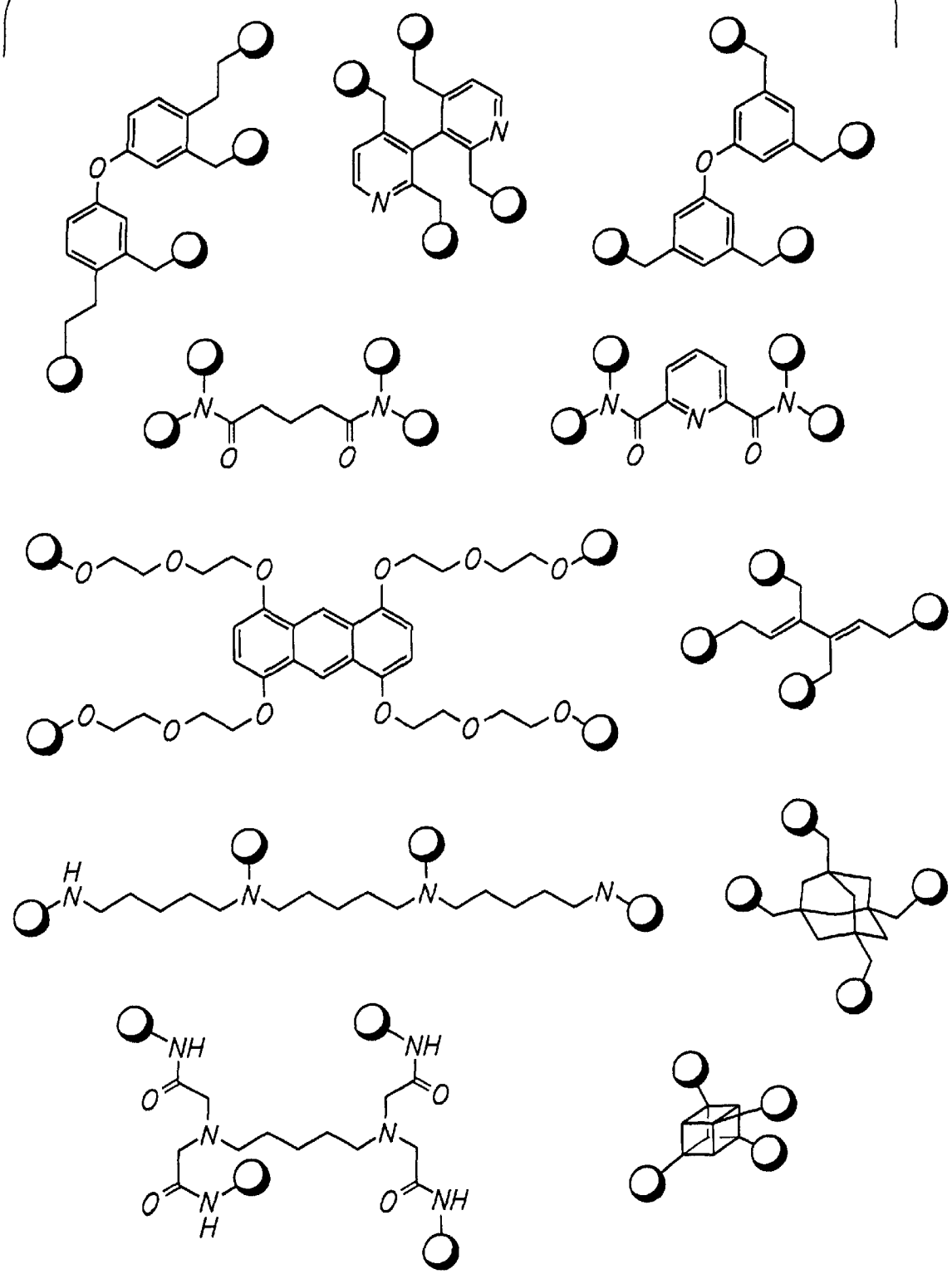
FIG. 3 illustrates examples of multibinding compounds comprising 4 ligands attached in different formats to a linker.

The above-described process can be extended to trimers (FIG. 2) and compound of higher valency (FIGS. 3 and 4).

Assays of each of the individual compounds of a collection generated as described above will lead to a subset of compounds with the desired enhanced activities (e.g., potency, selectivity, etc.). The analysis of this subset using a technique such as Ensemble Molecular Dynamics will provide a framework orientation that favors the properties desired. A wide diversity of linkers is commercially available (see, e.g., Available Chemical Directory (ACD)). Many of the linkers that are suitable for use in this invention fall into this category. Other can be readily synthesized by methods well known in the art and/or are described below.

Having selected a preferred framework geometry, the physical properties of the linker can be optimized by varying the chemical composition thereof. The composition of the linker can be varied in numerous ways to achieve the desired physical properties for the multibinding compound.

It can therefore be seen that there is a plethora of possibilities for the composition of a linker. Examples of linkers include aliphatic moieties, aromatic moieties, steroidal moieties, peptides, and the like. Specific examples are peptides or polyamides, hydrocarbons, aromatic groups, ethers, lipids, cationic or anionic groups, or a combination thereof.

Examples are given below, but it should be understood that various changes may be made and equivalents may be substituted without departing from the true spirit and scope of the invention. For example, properties of the linker can be modified by the addition or insertion of ancillary groups into or onto the linker, for example, to change the solubility of the multibinding compound (in water, fats, lipids, biological fluids, etc.), hydrophobicity, hydrophilicity, linker flexibility, antigenicity, stability, and the like. For example, the introduction of one or more poly(ethylene glycol) (PEG) groups onto or into the linker enhances the hydrophilicity and water solubility of the multibinding compound, increases both molecular weight and molecular size and, depending on the nature of the unPEGylated linker, may increase the in vivo retention time. Further PEG may decrease antigenicity and potentially enhances the overall rigidity of the linker.

Ancillary groups which enhance the water solubility/hydrophilicity of the linker and, accordingly, the resulting multibinding compounds are useful in practicing this invention. Thus, it is within the scope of the present invention to use ancillary groups such as, for example, small repeating units of ethylene glycols, alcohols, polyols (e.g., glycerin, glycerol propoxylate, saccharides, including mono-, oligosaccharides, etc.), carboxylates (e.g., small repeating units of glutamic acid, acrylic acid, etc.), amines (e.g., tetraethylenepentamine), and the like) to enhance the water solubility and/or hydrophilicity of the multibinding compounds of this invention. In preferred embodiments, the ancillary group used to improve water solubility/hydrophilicity will be a polyether.

The incorporation of lipophilic ancillary groups within the structure of the linker to enhance the lipophilicity and/or hydrophobicity of the multibinding compounds described herein is also within the scope of this invention. Lipophilic groups useful with the linkers of this invention include, by way of example only, aryl and heteroaryl groups which, as above, may be either unsubstituted or substituted with other groups, but are at least substituted with a group which allows their covalent attachment to the linker. Other lipophilic groups useful with the linkers of this invention include fatty acid derivatives which do not form bilayers in aqueous medium until higher concentrations are reached.

Also within the scope of this invention is the use of ancillary groups which result in the multibinding compound being incorporated or anchored into a vesicle or other membranous structure such as a liposome or a micelle. The term "lipid" refers to any fatty acid derivative that is capable of forming a bilayer or a micelle such that a hydrophobic portion of the lipid material orients toward the bilayer while a hydrophilic portion orients toward the aqueous phase. Hydrophilic characteristics derive from the presence of phosphato, carboxylic, sulfato, amino, sulfhydryl, nitro and other like groups well known in the art. Hydrophobicity could be conferred by the inclusion of groups that include, but are not limited to, long chain saturated and unsaturated aliphatic hydrocarbon groups of up to 20 carbon atoms and such groups substituted by one or more aryl, heteroaryl, cycloalkyl, and/or heterocyclic group(s). Preferred lipids are phosphglycerides and sphingolipids, representative examples of which include phosphatidylcholine, phosphatidylethanolamine, phosphatidylserine, phosphatidylinositol, phosphatidic acid, palmitoyleoyl phosphatidylcholine, lysophosphatidylcholine, lysophosphatidyl-ethanolamine, dipalmitoyl-phosphatidylcholine, dioleoylphosphatidylcholine, distearoyl-phosphatidylcholine or dilinoleoylphosphatidylcholine could be used. Other compounds lacking phosphorus, such as sphingolipid and glycosphingolipid families are also within the group designated as lipid. Additionally, the amphipathic lipids described above may be mixed with other lipids including triglycerides and sterols.

The flexibility of the linker can be manipulated by the inclusion of ancillary groups which are bulky and/or rigid. The presence of bulky or rigid groups can hinder free rotation about bonds in the linker or bonds between the linker and the ancillary group(s) or bonds between the linker and the functional groups. Rigid groups can include, for example, those groups whose conformational lability is restrained by the presence of rings and/or multiple bonds within the group, for example, aryl, heteroaryl, cycloalkyl, cycloalkenyl, and heterocyclic groups. Other groups which can impart rigidity include polypeptide groups such as oligo- or polyproline chains.

Rigidity can also be imparted electrostatically. Thus, if the ancillary groups are either positively or negatively charged, the similarly charged ancillary groups will force the presenter linker into a configuration affording the maximum distance between each of the like charges. The energetic cost of bringing the like-charged groups closer to each other will tend to hold the linker in a configuration that maintains the separation between the like-charged ancillary groups. Further ancillary groups bearing opposite charges will tend to be attracted to their oppositely charged counterparts and potentially may enter into both inter- and intramolecular ionic bonds. This non-covalent mechanism will tend to hold the linker into a conformation which allows bonding between the oppositely charged groups. The addition of ancillary groups which are charged, or alternatively, bear a latent charge when deprotected, following addition to the linker, include deprotectation of a carboxyl, hydroxyl, thiol or amino group by a change in pH, oxidation, reduction or other mechanisms known to those skilled in the art which result in removal of the protecting group, is within the scope of this invention.

Rigidity may also be imparted by internal hydrogen bonding or by hydrophobic collapse.

Bulky groups can include, for example, large atoms, ions (e.g., iodine, sulfur, metal ions, etc.) or groups containing large atoms, polycyclic groups, including aromatic groups, non-aromatic groups and structures incorporating one or more carbon-carbon multiple bonds (i.e., alkenes and alkynes). Bulky groups can also include oligomers and polymers which are branched- or straight-chain species. Species that are branched are expected to increase the rigidity of the structure more per unit molecular weight gain than are straight-chain species.

In preferred embodiments, rigidity is imparted by the presence of cyclic groups (e.g., aryl, heteroaryl, cycloalkyl, heterocyclic, etc.). In other preferred embodiments, the linker comprises one or more six-membered rings. In still further preferred embodiments, the ring is an aryl group such as, for example, phenyl or naphthyl.

In view of the above, it is apparent that the appropriate selection of a linker group providing suitable orientation, restricted/unrestricted rotation, the desired degree of hydrophobicity/hydrophilicity, etc. is well within the skill of the art. Eliminating or reducing antigenicity of the multibinding compounds described herein is also within the scope of this invention. In certain cases, the antigenicity of a multibinding compound may be eliminated or reduced by use of groups such as, for example, poly(ethylene glycol).

As explained above, the multibinding compounds described herein comprise 2–10 ligands attached to a linker that attaches the ligands in such a manner that they are presented to the enzyme for multivalent interactions with ligand binding sites thereon/therein. The linker spatially constrains these interactions to occur within dimensions defined by the linker. This and other factors increases the biological activity of the multibinding compound as compared to the same number of ligands made available in monobinding form.

The compounds of this invention are preferably represented by the empirical Formula $(L)_p(X)_q$ where L, X, p and q are as defined above. This is intended to include the several ways in which the ligands can be linked together in order to achieve the objective of multivalency, and a more detailed explanation is described below.

As noted previously, the linker may be considered as a framework to which ligands are attached. Thus, it should be recognized that the ligands can be attached at any suitable position on this framework, for example, at the termini of a linear chain or at any intermediate position.

The simplest and most preferred multibinding compound is a bivalent compound which can be represented as L—X—L, where each L is independently a ligand which may be the same or different and each X is independently the linker. Examples of such bivalent compounds are provided in FIG. 1 where each shaded circle represents a ligand. A trivalent compound could also be represented in a linear fashion, i.e., as a sequence of repeated units L—X—L—X—L, in which L is a ligand and is the same or different at each occurrence, as can X. However, a trimer can also be a radial multibinding compound comprising three ligands attached to a central core, and thus represented as $(L)_3X$, where the linker X could include, for example, an aryl or cycloalkyl group. Illustrations of trivalent and tetravalent compounds of this invention are found in FIGS. 2 and 3 respectively where, again, the shaded circles represent ligands. Tetravalent compounds can be represented in a linear array, e.g.,

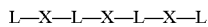

in a branched array, e.g.,

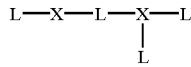

(a branched construct analogous to the isomers of butane—n-butyl, iso-butyl, sec-butyl, and t-butyl) or in a tetrahedral array, e.g.,

where X and L are as defined herein. Alternatively, it could be represented as an alkyl, aryl or cycloalkyl derivative as above with four (4) ligands attached to the core linker.

The same considerations apply to higher multibinding compounds of this invention containing 5–10 ligands as illustrated in FIG. 4 where, as before, the shaded circles represent ligands. However, for multibinding agents attached to a central linker such as aryl or cycloalkyl, there is a self-evident constraint that there must be sufficient attachment sites on the linker to accommodate the number of ligands present; for example, a benzene ring could not directly accommodate more than 6 ligands, whereas a multi-ring linker (e.g., biphenyl) could accommodate a larger number of ligands.

The above described compounds may alternatively be represented as cyclic chains of the form:

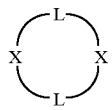

and variants thereof.

All of the above variations are intended to be within the scope of the invention defined by the Formula $(L)_p(X)_q$.

With the foregoing in mind, a preferred linker may be represented by the following formula:

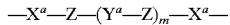

wherein:

m is an integer of from 0 to 20;

$X^a$ at each separate occurrence is selected from the group consisting of —O—, —S—, —NR—, —C(O)—, —C(O)O—, —OC(O)—, —C(O)NR—, —NRC(O)—, C(S), —C(S)O—, —C(S)NR—, —NRC(S)—, or a covalent bond where R is as defined below;

Z at each separate occurrence is selected from the group consisting of alkylene, substituted alkylene, alkenylene, substituted alkenylene, alkynylene, substituted alkynylene, or a covalent bond;

each $Y^a$ at each separate occurrence is selected from the group consisting of —O—, —C(O)—, —OC(O)—, —C(O)O—, —NR—, —S(O)n—, —C(O)NR'—, —NR'C(O)—, —NR'C(O)NR'—, —NR'C(S)NR'—, —C(=NR')—NR'—, —NR'—C(=NR')—, —OC(O)—NR'—, —NR'—C(O)—O—, —N=C($X^a$)—NR'—, —NR'—C($X^a$)=N—, —P(O)(OR')—O—, —O—P(O)(OR')—, —S(O)$_n$CR' R''—, —S(O)$_n$—NR'—, —NR'—S(O)$_n$— and a covalent bond; where n is 0, 1 or 2; and R, R' and R'' at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that at least one of $X^a$, Z, and $Y^a$ is not a covalent bond.

Additionally, the linker moiety can be optionally substituted at any atom therein by one or more alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic group.

In view of the above description of the linker, it is understood that the term "linker" when used in combination with the term "multibinding compound" includes both a covalently contiguous single linker (e.g., L—X—L) and multiple covalently non-contiguous linkers (L—X—L—X—L) within the multibinding compound.

Combinatorial Libraries

The methods described above lend themselves to combinatorial approaches for identifying multimeric compounds which possess multibinding properties.

Specifically, factors such as the proper juxtaposition of the individual ligands of a multibinding compound with respect to the relevant array of binding sites on a target or targets is important in optimizing the interaction of the multibinding compound with its target(s) and to maximize the biological advantage through multivalency. One approach is to identify a library of candidate multibinding compounds with properties spanning the multibinding parameters that are relevant for a particular target. These parameters include: (1) the identity of ligand(s), (2) the orientation of ligands, (3) the valency of the construct, (4) linker length, (5) linker geometry, (6) linker physical properties, and (7) linker chemical functional groups.

Libraries of multimeric compounds potentially possessing multibinding properties (i.e., candidate multibinding compounds) and comprising a multiplicity of such variables are prepared and these libraries are then evaluated via conventional assays corresponding to the ligand selected and the multibinding parameters desired. Considerations relevant to each of these variables are set forth below:

Selection of Ligand(s):

A single ligand or set of ligands is (are) selected for incorporation into the libraries of candidate multibinding compounds which library is directed against a particular biological target or targets e.g., β2 adrenergic receptor. The only requirement for the ligands chosen is that they are capable of interacting with the selected target(s). Thus, ligands may be known drugs, modified forms of known drugs, substructures of known drugs or substrates of modified forms of known drugs (which are competent to interact with the target), or other compounds. Ligands are preferably chosen based on known favorable properties that may be projected to be carried over to or amplified in multibinding forms. Favorable properties include demonstrated safety and efficacy in human patients, appropriate PK/ADME profiles, synthetic accessibility, and desirable physical properties such as solubility, log P, etc. However, it is crucial to note that ligands which display an unfavorable property from among the previous list may obtain a more favorable property through the process of multibinding compound formation; i.e., ligands should not necessarily be excluded on such a basis. For example, a ligand that is not sufficiently potent at a particular target so as to be efficacious in a human patient may become highly potent and efficacious when presented in multibinding form. A ligand that is potent and efficacious but not of utility because of a non-mechanism-related toxic side effect may have increased therapeutic index (increased potency relative to toxicity) as a multibinding compound. Compounds that exhibit short in vivo half-lives may have extended half-lives as multibinding compounds. Physical properties of ligands that limit their usefulness (e.g. poor bioavailability due to low solubility, hydrophobicity, hydrophilicity) may be rationally modulated in multibinding forms, providing compounds with physical properties consistent with the desired utility.

Orientation: Selection of Ligand Attachment Points and Linking Chemistry:

Several points are chosen on each ligand at which to attach the ligand to the linker. The selected points on the ligand/linker for attachment are functionalized to contain complementary reactive functional groups. This permits probing the effects of presenting the ligands to their receptor (s) in multiple relative orientations, an important multibinding design parameter. The only requirement for choosing attachment points is that attaching to at least one of these points does not abrogate activity of the ligand. Such points for attachment can be identified by structural information when available. For example, inspection of a co-crystal structure of a protease inhibitor bound to its target allows one to identify one or more sites where linker attachment will not preclude the enzyme:inhibitor interaction. Alternatively, evaluation of ligand/target binding by nuclear magnetic resonance will permit the identification of sites non-essential for ligand/target binding. See, for example, Fesik, et al., U.S. Pat. No. 5,891,643. When such structural information is not available, utilization of structure-activity relationships (SAR) for ligands will suggest positions where substantial structural variations are and are not allowed. In the absence of both structural and SAR information, a library is merely selected with multiple points of attachment to allow presentation of the ligand in multiple distinct orientations. Subsequent evaluation of this library will indicate what positions are suitable for attachment.

It is important to emphasize that positions of attachment that do abrogate the activity of the monomeric ligand may also be advantageously included in candidate multibinding compounds in the library provided that such compounds bear at least one ligand attached in a manner which does not abrogate intrinsic activity. This selection derives from, for example, heterobivalent interactions within the context of a single target molecule. For example, consider a receptor antagonist ligand bound to its target receptor, and then consider modifying this ligand by attaching to it a second copy of the same ligand with a linker which allows the second ligand to interact with the same receptor molecule at sites proximal to the antagonist binding site, which include elements of the receptor that are not part of the formal antagonist binding site and/or elements of the matrix surrounding the receptor such as the membrane. Here, the most favorable orientation for interaction of the second ligand molecule with the receptor/matrix may be achieved by attaching it to the linker at a position which abrogates activity of the ligand at the formal antagonist binding site. Another way to consider this is that the SAR of individual ligands within the context of a multibinding structure is often different from the SAR of those same ligands in momomeric form.

The foregoing discussion focused on bivalent interactions of dimeric compounds bearing two copies of the same ligand joined to a single linker through different attachment points, one of which may abrogate the binding/activity of the monomeric ligand. It should also be understood that bivalent advantage may also be attained with heterodimeric constructs bearing two different ligands that bind to common or different targets. For example, a $5HT_4$ receptor antagonist and a bladder-selective muscarinic $M_3$ antagonist may be joined to a linker through attachment points which do not abrogate the binding affinity of the monomeric ligands for their respective receptor sites. The dimeric compound may achieve enhanced affinity for both receptors due to favorable interactions between the $5HT_4$ ligand and elements of the $M_3$ receptor proximal to the formal $M_3$ antagonist binding site and between the $M_3$ ligand and elements of the $5HT_4$ receptor proximal to the formal $5HT_4$ antagonist binding site. Thus, the dimeric compound may be more potent and selective antagonist of overactive bladder and a superior therapy for urinary urge incontinence.

Once the ligand attachment points have been chosen, one identifies the types of chemical linkages that are possible at those points. The most preferred types of chemical linkages are those that are compatible with the overall structure of the ligand (or protected forms of the ligand) readily and generally formed stable and intrinsically inocuous under typical chemical and physiological conditions, and compatible with a large number of available linkers. Amide bonds, ethers, amines, carbamates, ureas; and sulfonamides are but a few examples of preferred linkages.

Linkers: Spanning Relevant Multibinding Parameters Through Selection of Valency, Linker Length, Linker Geometry, Rigidity, Physical Properties, and Chemical Functional Groups In the library of linkers employed to generate the library of candidate multibinding compounds, the selection of linkers employed in this library of linkers takes into consideration the following factors:

Valency:

In most instances the library of linkers is initiated with divalent linkers. The choice of ligands and proper juxtaposition of two ligands relative to their binding sites permits such molecules to exhibit target binding affinities and specificities more than sufficient to confer biological advantage. Furthermore, divalent linkers or constructs are also typically of modest size such that they retain the desirable biodistribution properties of small molecules.

Linker Length:

Linkers are chosen in a range of lengths to allow the spanning of a range of inter-ligand distances that encompass the distance preferable for a given divalent interaction. In some instances the preferred distance can be estimated rather precisely from high-resolution structural information of targets, typically enzymes and soluble receptor targets. In other instances where high-resolution structural information is not available (such as 7TM G-protein coupled receptors), one can make use of simple models to estimate the maximum distance between binding sites either on adjacent receptors or at different locations on the same receptor. In situations where two binding sites are present on the same target (or target subunit for multisubunit targets), preferred linker distances are 2–20 Å, with more preferred linker distances of 3–12 Å. In situations where two binding sites reside on separate (e.g., protein) target sites, preferred linker distances are 20–100 Å, with more preferred distances of 30–70 Å.

Linker Geometry and Rigidity:

The combination of ligand attachment site, linker length, linker geometry, and linker rigidity determine the possible ways in which the ligands of candidate multibinding compounds may be displayed in three dimensions and thereby presented to their binding sites. Linker geometry and rigidity are nominally determined by chemical composition and bonding pattern, which may be controlled and are systematically varied as another spanning function in a multibinding array. For example, linker geometry is varied by attaching two ligands to the ortho, meta, and para positions of a benzene ring, or in cis- or trans-arrangements at the 1,1-vs. 1,2- vs. 1,3- vs. 1,4-positions around a cyclohexane core or in cis- or trans-arrangements at a point of ethylene unsaturation. Linker rigidity is varied by controlling the number and relative energies of different conformational states possible for the linker. For example, a divalent compound bearing two ligands joined by 1,8-octyl linker has many more degrees of freedom, and is therefore less rigid than a compound in which the two ligands are attached to the 4,4' positions of a biphenyl linker.

Linker Physical Properties:

The physical properties of linkers are nominally determined by the chemical constitution and bonding patterns of the linker, and linker physical properties impact the overall physical properties of the candidate multibinding compounds in which they are included. A range of linker compositions is typically selected to provide a range of physical properties (hydrophobicity, hydrophilicity, amphiphilicity, polarization, acidity, and basicity) in the candidate multibinding compounds. The particular choice of linker physical properties is made within the context of the physical properties of the ligands they join and preferably the goal is to generate molecules with favorable PK/ADME properties. For example, linkers can be selected to avoid those that are too hydrophilic or too hydrophobic to be readily absorbed and/or distributed in vivo.

Linker Chemical Functional Groups:

Linker chemical functional groups are selected to be compatible with the chemistry chosen to connect linkers to the ligands and to impart the range of physical properties sufficient to span initial examination of this parameter.

Combinatorial Synthesis

Having chosen a set of n ligands (n being determined by the sum of the number of different attachment points for each ligand chosen) and m linkers by the process outlined above, a library of (n!)m candidate divalent multibinding compounds is prepared which spans the relevant multibinding design parameters for a particular target. For example, an array generated from two ligands, one which has two attachment points (A1, A2) and one which has three attachment points (B1, B2, B3) joined in all possible combinations provide for at least 15 possible combinations of multibinding compounds:

A1-A1 A1-A2 A1-B1 A1-B2 A1-B3 A2-A2 A2-B1 A2-B2 A2-B3 B1-B1 B1-B2 B1-B3 B2-B2 B2-B3 B3-B3

When each of these combinations is joined by 10 different linkers, a library of 150 candidate multibinding compounds results.

Given the combinatorial nature of the library, common chemistries are preferably used to join the reactive functionalies on the ligands with complementary reactive functionalities on the linkers. The library therefore lends itself to efficient parallel synthetic methods. The combinatorial library can employ solid phase chemistries well known in the art wherein the ligand and/or linker is attached to a solid support. Alternatively and preferably, the combinatorial libary is prepared in the solution phase. After synthesis, candidate multibinding compounds are optionally purified before assaying for activity by, for example, chromatographic methods (e.g., HPLC).

Analysis of Array by Biochemical, Analytical, Pharmacological, and Computational Methods:

Various methods are used to characterize the properties and activities of the candidate multibinding compounds in the library to determine which compounds possess multibinding properties. Physical constants such as solubility under various solvent conditions and logD/clogD values can be determined. A combination of NMR spectroscopy and computational methods is used to determine low-energy conformations of the candidate multibinding compounds in fluid media. The ability of the members of the library to bind to the desired target and other targets is determined by various standard methods, which include radioligand displacement assays for receptor and ion channel targets, and kinetic inhibition analysis for many enzyme targets. In vitro efficacy, such as for receptor agonists and antagonists, ion channel blockers, and antimicrobial activity, can also be determined. Pharmacological data, including oral absorption, everted gut penetration, other pharmacokinetic parameters and efficacy data can be determined in appropriate models. In this way, key structure-activity relationships are obtained for multibinding design parameters which are then used to direct future work.

The members of the library which exhibit multibinding properties, as defined herein, can be readily determined by conventional methods. First those members which exhibit multibinding properties are identified by conventional methods as described above including conventional assays (both in vitro and in vivo).

Second, ascertaining the structure of those compounds which exhibit multibinding properties can be accomplished via art recognized procedures. For example, each member of the library can be encrypted or tagged with appropriate information allowing determination of the structure of relevant members at a later time. See, for example, Dower, et al., International Patent Application Publication No. WO 93/06121; Brenner, et al., Proc. Natl. Acad. Sci., USA, 89:5181 (1992): Gallop, et al., U.S. Pat. No. 5,846,839; each of which are incorporated herein by reference in its entirety. Alternatively, the structure of relevant multivalent compounds can also be determined from soluble and untagged libaries of candidate multivalent compounds by methods known in the art such as those described by Hindsgaul, et al., Canadian Patent Application No. 2,240,325 which was published on Jul. 11, 1998. Such methods couple frontal affinity chromatography with mass spectroscopy to determine both the structure and relative binding affinities of candidate multibinding compounds to receptors.

The process set forth above for dimeric candidate multibinding compounds can, of course, be extended to trimeric candidate compounds and higher analogs thereof.

Follow-up Synthesis and Analysis of Additional Array(s):

Based on the information obtained through analysis of the initial library, an optional component of the process is to ascertain one or more promising multibinding "lead" compounds as defined by particular relative ligand orientations, linker lengths, linker geometries, etc. Additional libraries can then be generated around these leads to provide for further information regarding structure to activity relationships. These arrays typically bear more focused variations in linker structure in an effort to further optimize target affinity and/or activity at the target (antagonism, partial agonism, etc.), and/or alter physical properties. By iterative redesign/analysis using the novel principles of multibinding design along with classical medicinal chemistry, biochemistry, and pharmacology approaches, one is able to prepare and identify optimal multibinding compounds that exhibit biological advantage towards their targets and as therapeutic agents.

To further elaborate upon this procedure, suitable divalent linkers include, by way of example only, those derived from dicarboxylic acids, disulfonylhalides, dialdehydes, diketones, dihalides, diisocyanates,diamines, diols, mixtures of carboxylic acids, sulfonylhalides, aldehydes, ketones, halides, isocyanates, amines and diols. In each case, the carboxylic acid, sulfonylhalide, aldehyde, ketone, halide, isocyanate, amine and diol functional group is reacted with a complementary functionality on the ligand to form a covalent linkage. Such complementary functionality is well known in the art as illustrated in the following table:

| COMPLEMENTARY BINDING CHEMISTRIES | | |
|---|---|---|
| First Reactive Group | Second Reactive Group | Linkage |
| hydroxyl | isocyanate | urethane |
| amine | epoxide | β-amine |
| hydroxyamine | sulfonyl halide | sulfonamide |
| carboxyl acid | amine | amide |
| hydroxyl | alkyl/aryl halide | ether |
| aldehyde | amine/NaCNBH$_3$ | amine |
| ketone | amine/NaCNBH$_3$ | amine |
| amine | isocyanate | urea |

Exemplary linkers include the following linkers identified as X-1 through X-418 as set forth below:

Diacids

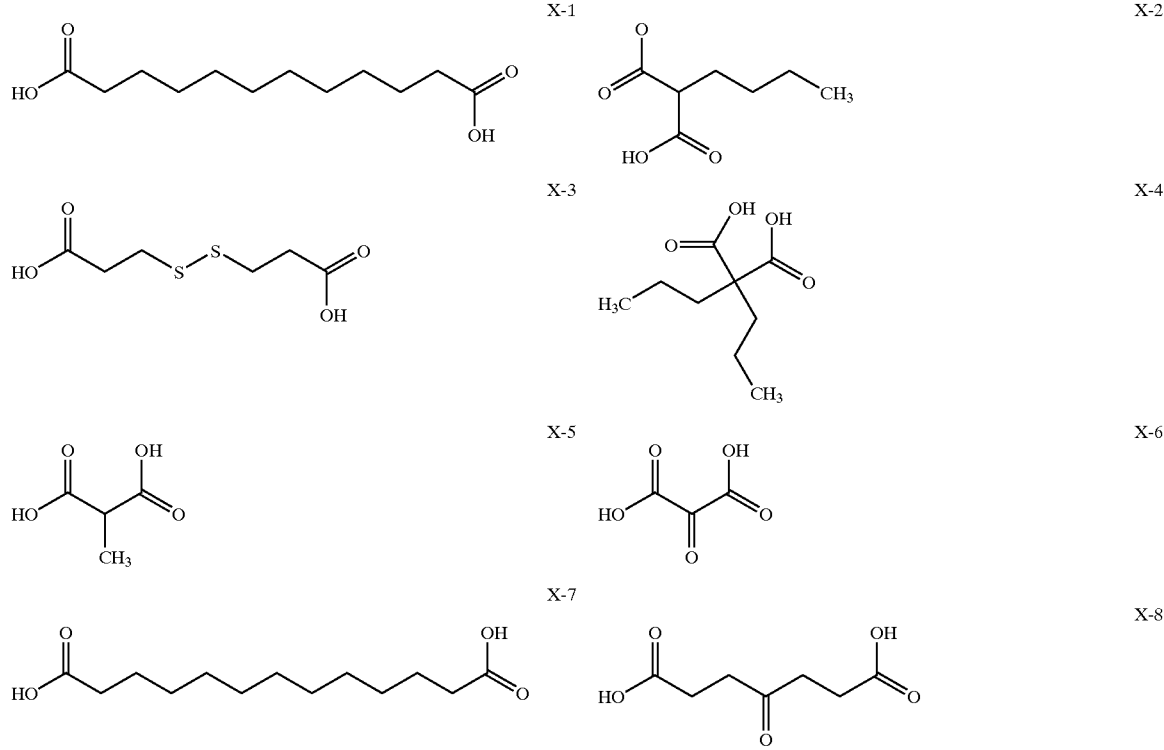

-continued
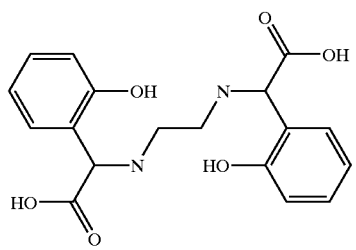
X-9
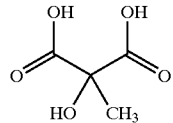
X-10
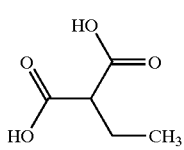
X-11
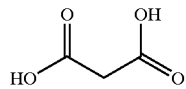
X-12
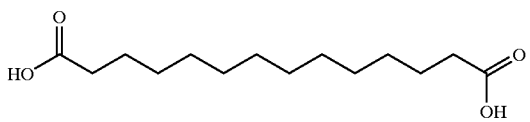
X-13
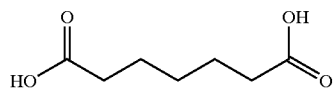
X-14
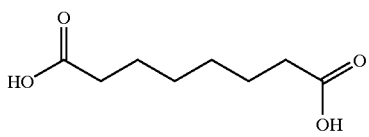
X-15
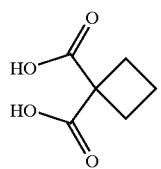
X-16
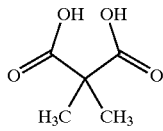
X-17
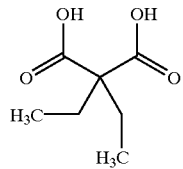
X-18
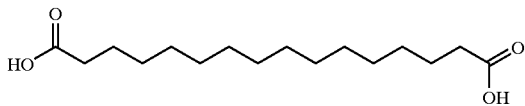
X-19
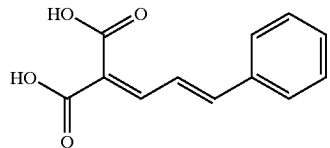
X-20
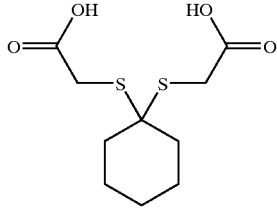
X-21
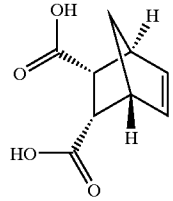
X-22
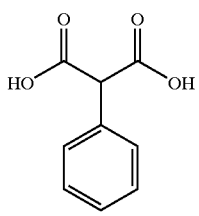
X-23
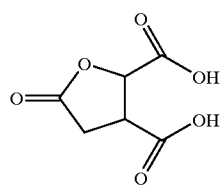
X-24

-continued
X-25
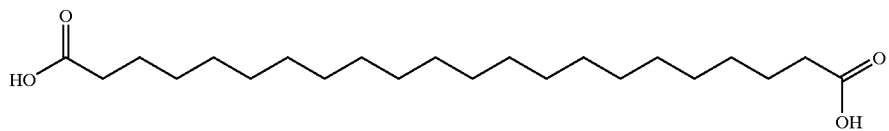
X-26
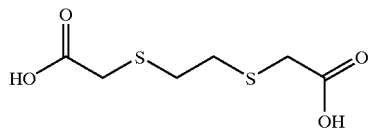
X-27
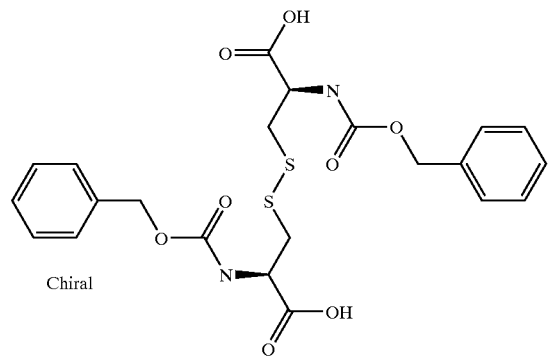
Chiral
X-28
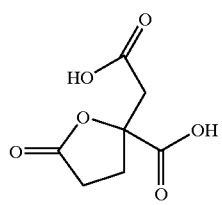
X-29
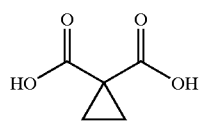
X-30
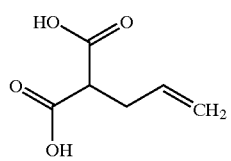
X-31
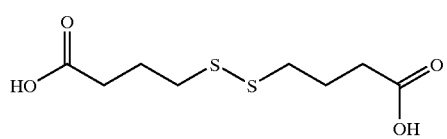
X-32
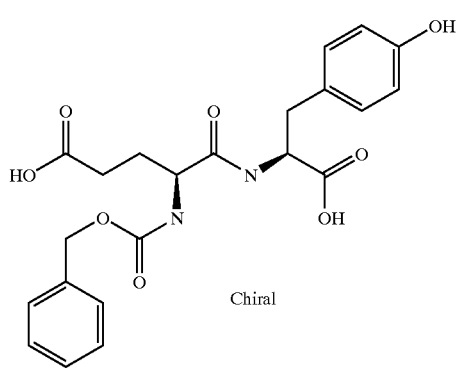
Chiral
X-33
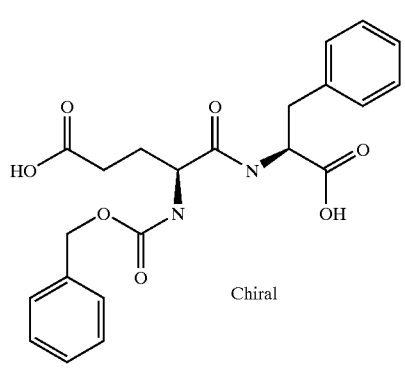
Chiral
X-34
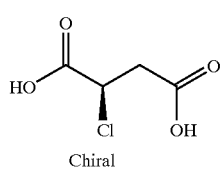
Chiral
X-35
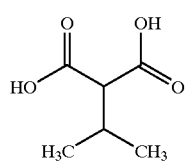
X-36
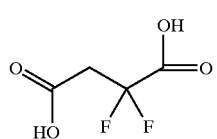
X-37
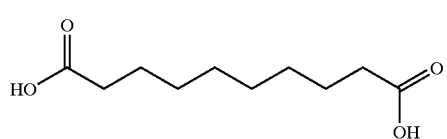

-continued
X-38
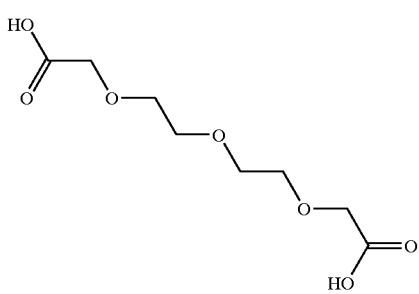
X-39
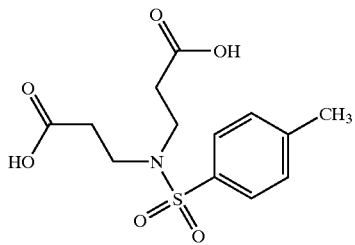
X-40
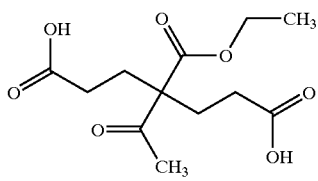
X-41
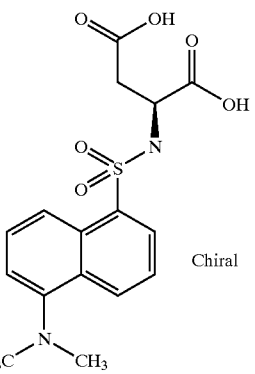
Chiral
X-42
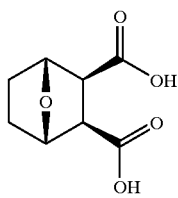
X-43
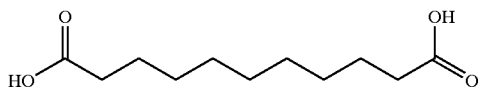
X-44
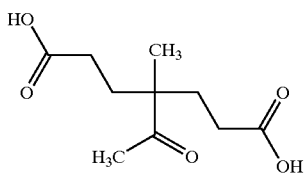
X-45
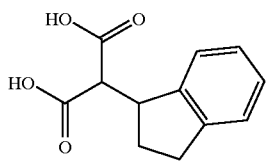
X-46
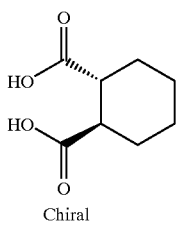
Chiral
X-47
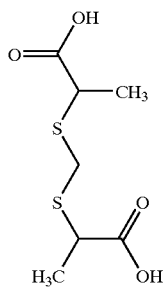
X-48
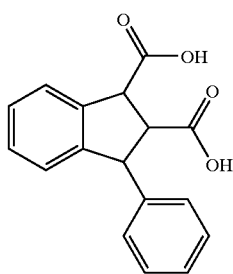

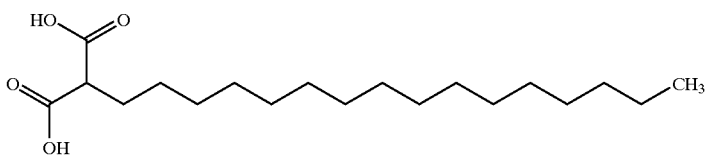
X-49
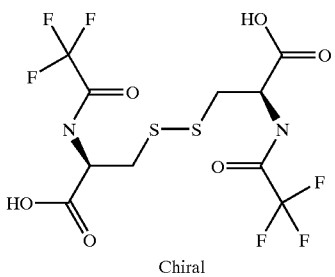
X-50
Chiral
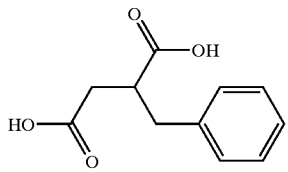
X-51
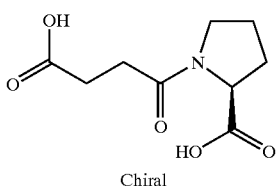
X-52
Chiral
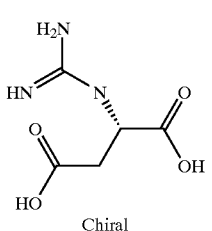
X-53
Chiral
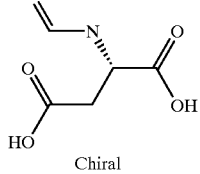
X-54
Chiral
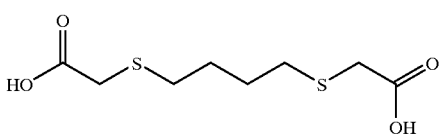
X-55
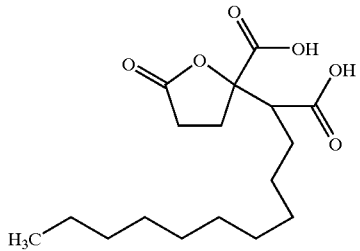
X-56
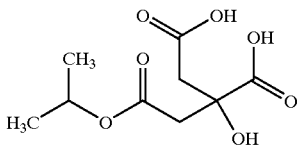
X-57
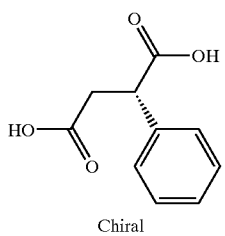
X-58
Chiral
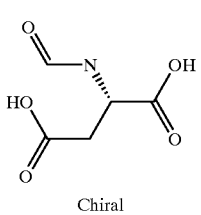
X-59
Chiral
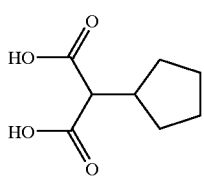
X-60

-continued
X-61
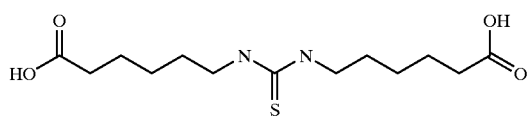
X-62
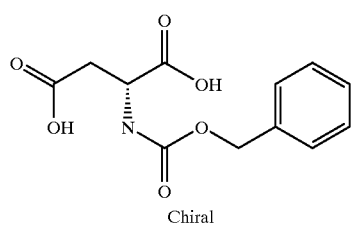
Chiral
X-63
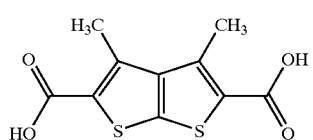
X-64
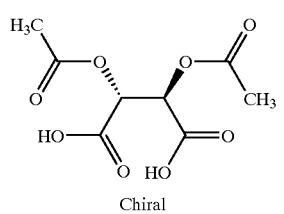
Chiral
X-65
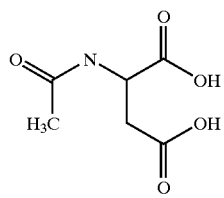
X-66
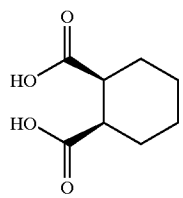
X-67
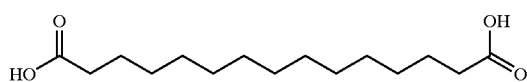
X-68
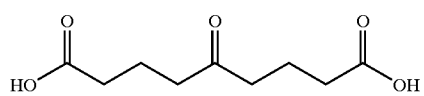
X-69
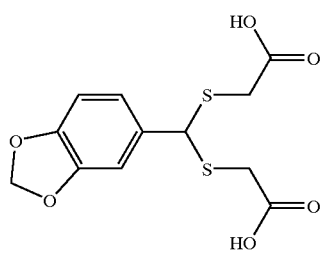
X-70
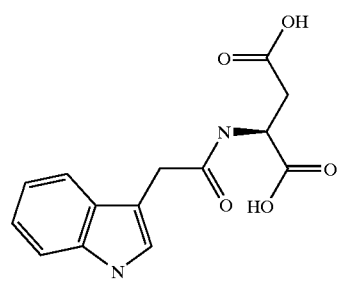
Chiral
X-71
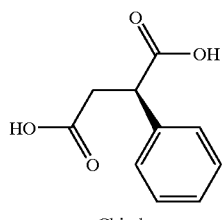
Chiral
X-72
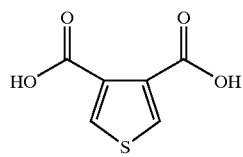
X-73
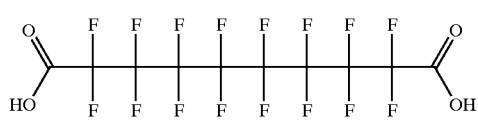
X-74
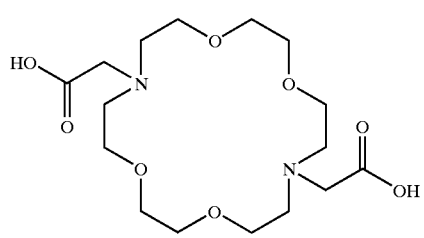

-continued
X-75
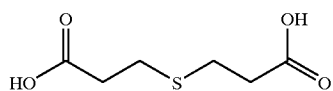
X-76
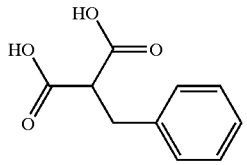
X-77
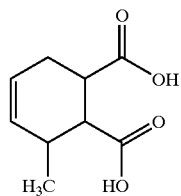
X-78
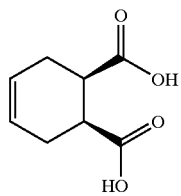
X-79
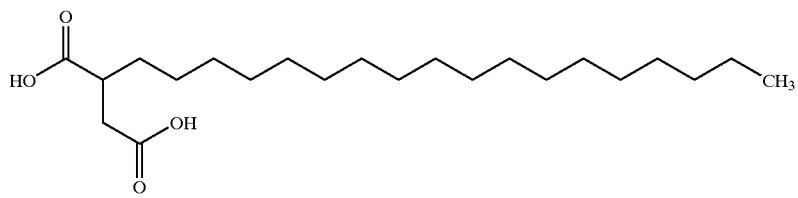
X-80
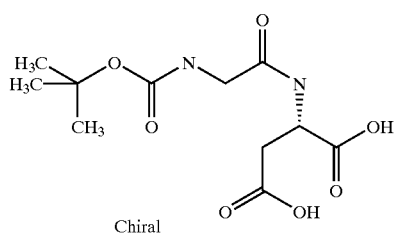
Chiral
X-81
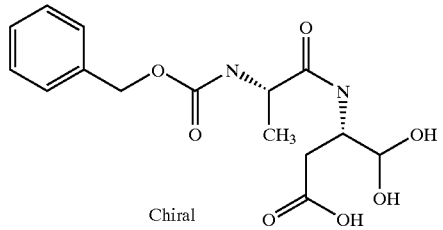
Chiral
X-82
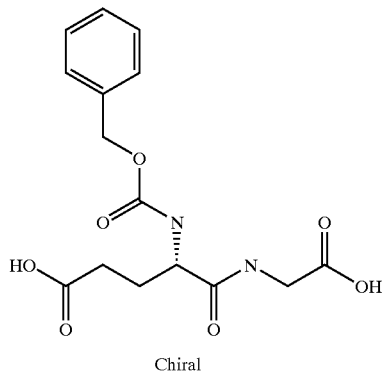
Chiral
X-83
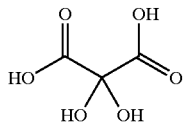
X-84
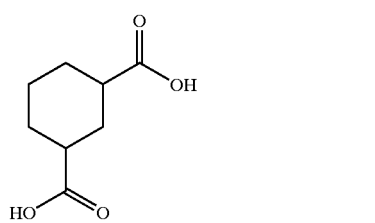
X-85
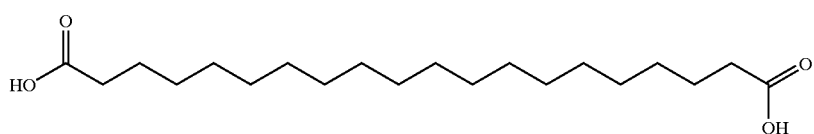

-continued
X-86
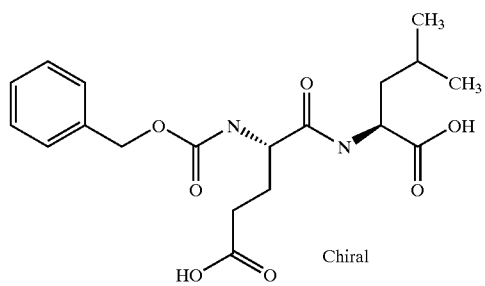
X-87
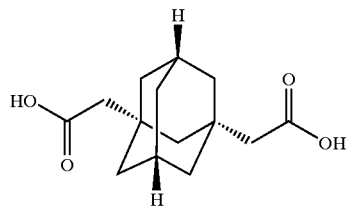
X-88
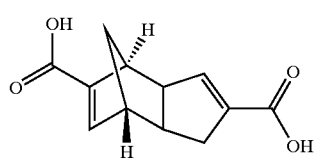
X-89
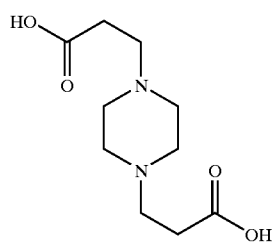
X-90
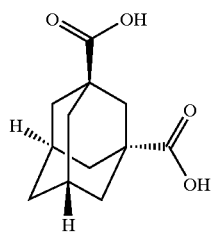
X-91
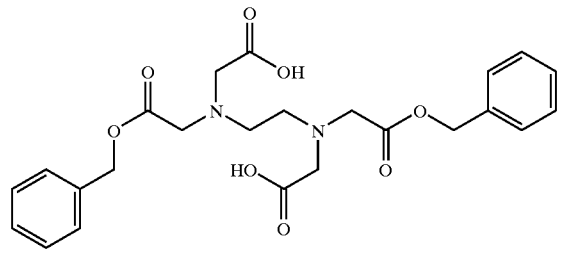
X-92
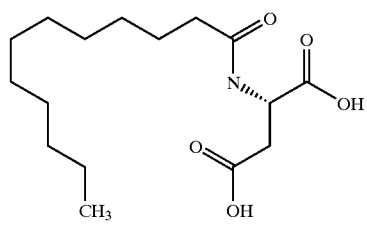
X-93
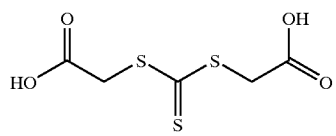
X-94
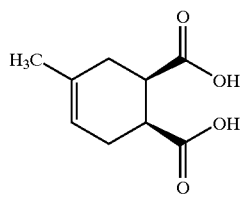
X-95
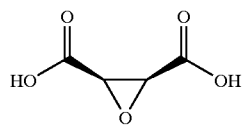
X-96
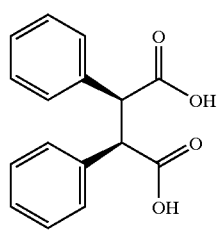
X-97
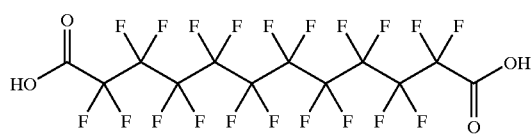

X-98 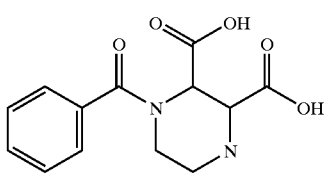
X-99 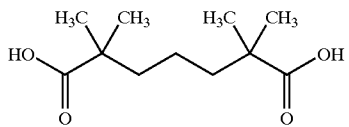
X-100 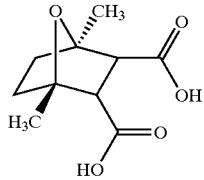
X-101 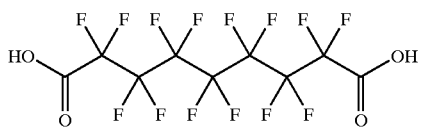
X-102 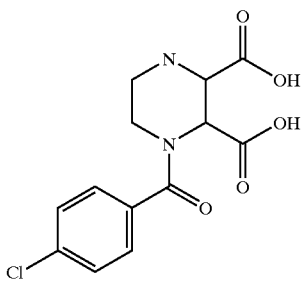
X-103 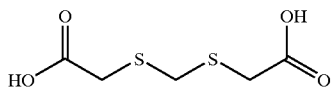
X-104 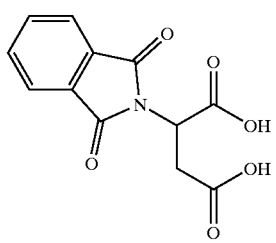
X-105 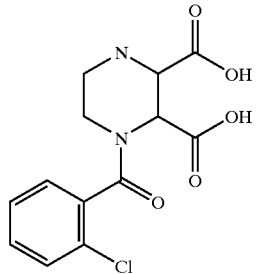
X-106 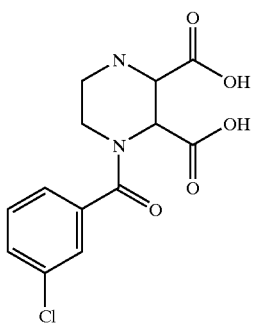
X-107 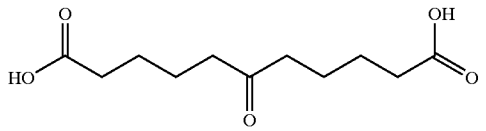
X-108
X-109

-continued
X-110
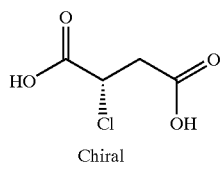
Chiral
X-111
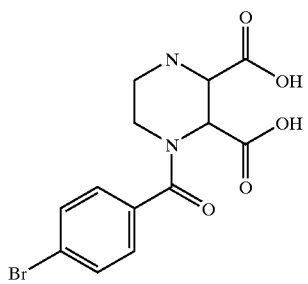
X-112
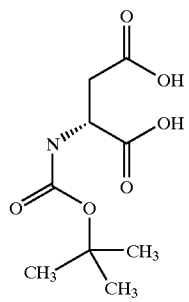
Chiral
X-113
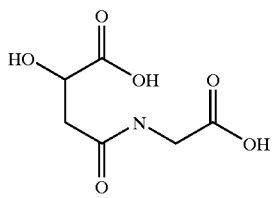
X-114
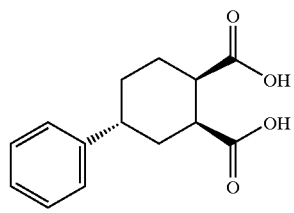
X-115
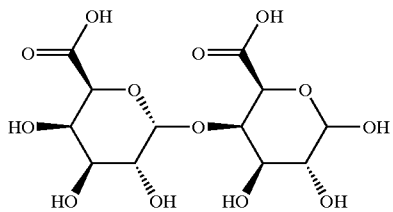
Chiral
X-116
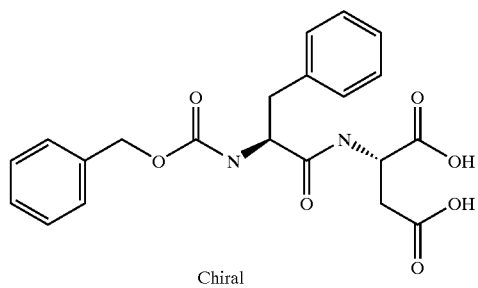
Chiral
X-117
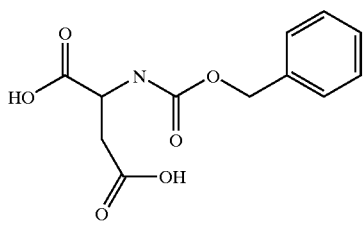
X-118
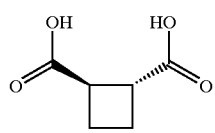
X-119
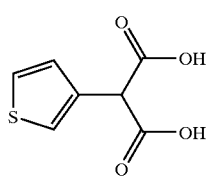
X-120
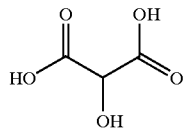
X-121
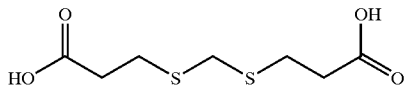

-continued
X-122 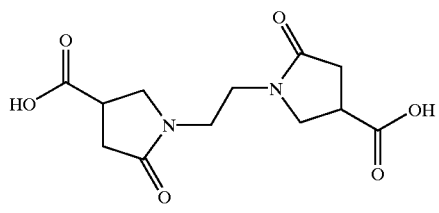
X-123 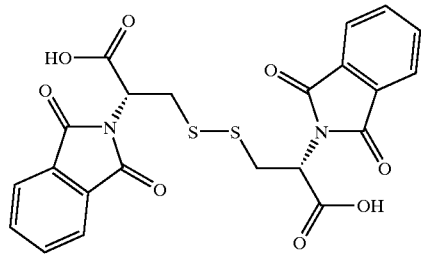
Chiral
X-124 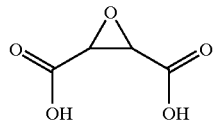
X-125 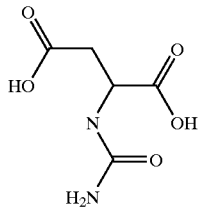
X-126 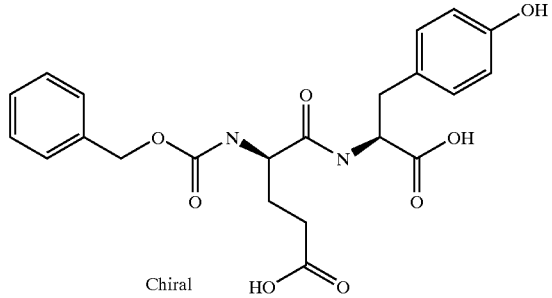
Chiral
X-127
X-128 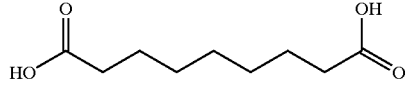
X-129 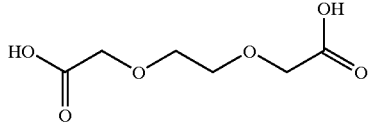
X-130 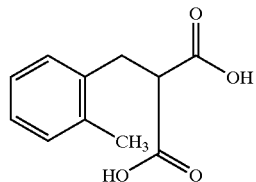
X-131 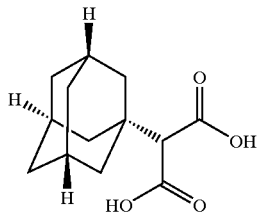
X-132 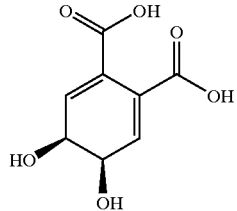
Disulfonyl Halides -continued X-133, X-134, X-135, X-136, X-137, X-138, X-139, X-140, X-141, X-142, X-143, X-144, X-145, X-146

| X-147 | X-148 |
|---|---|
| 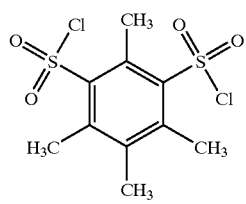 | 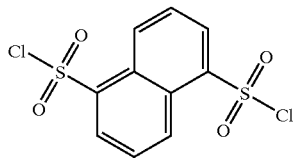 |
| X-149 | X-150 |
|---|---|
| 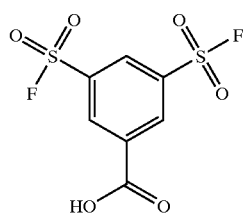 | 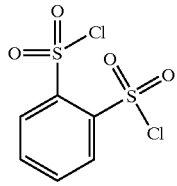 |
| X-151 | X-152 |
|---|---|
| 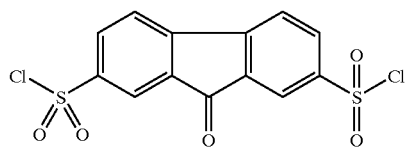 | 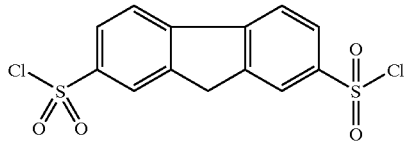 |
Dialdehydes
X-153
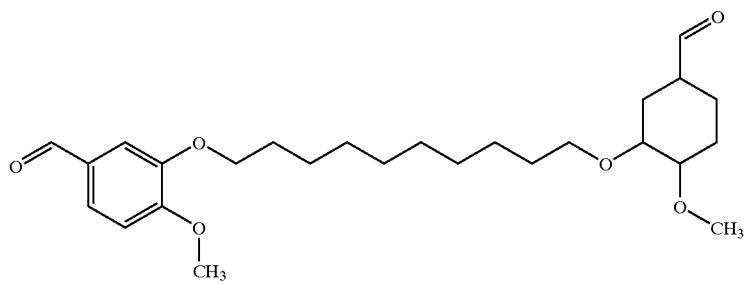
| X-154 | X-155 |
|---|---|
| 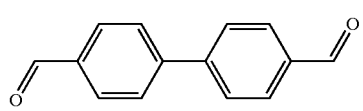 | 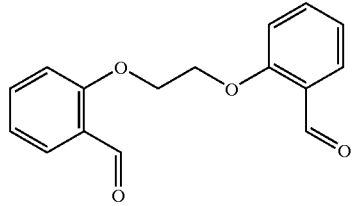 |
| X-156 | X-157 |
|---|---|
| 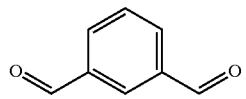 | 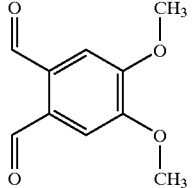 |
X-158 X-159
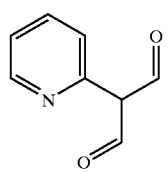
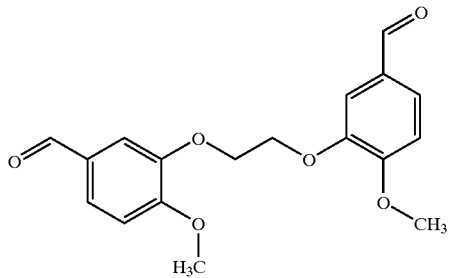

-continued
X-160
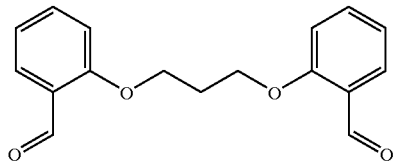
X-161
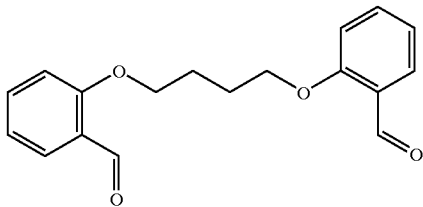
X-162
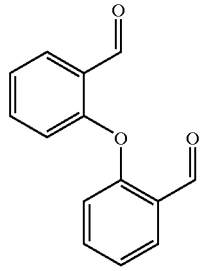
X-163
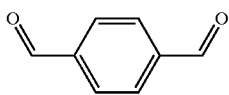
X-164
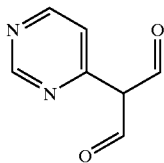
X-165
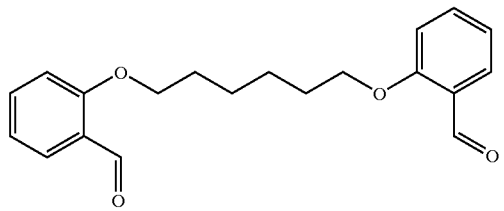
X-166
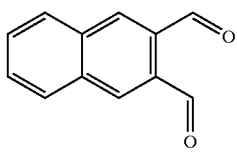
X-167
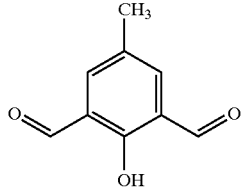
X-168
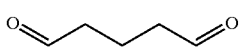
X-169
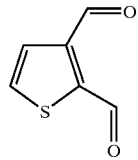
X-170
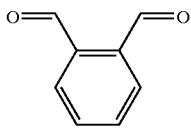
X-171
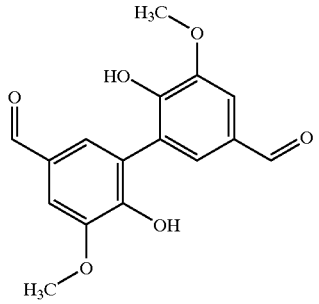
X-172
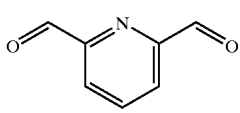
X-173
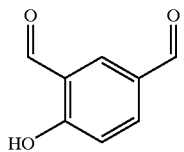

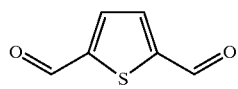
Dihalides
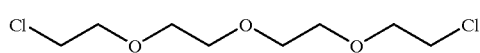
X-175
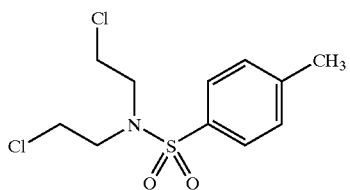
X-176
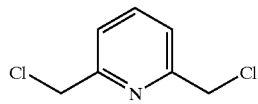
X-177
I~~~~I
X-178
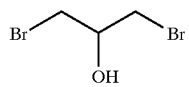
X-179
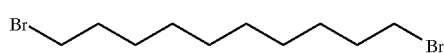
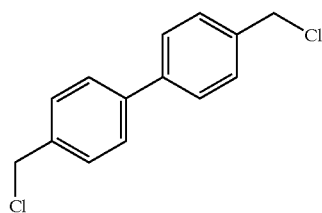
X-180
Br~~OH~~Br (with OH)
X-181
Cl~~O-C(=O)-O~~Cl
X-182
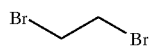
X-183
I~~~~~I
X-184
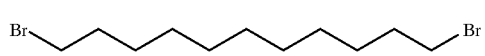
X-185
Cl-CH2-C(=CH2)-CH2-Cl
X-186
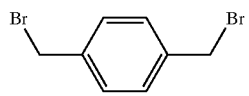
X-187
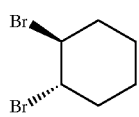
X-188
HOOC-(CH2)3-C6H4-N(CH2CH2Cl)2
X-189
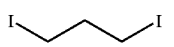
X-190
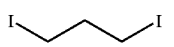
X-191
I~~~I
X-192

-continued
X-193 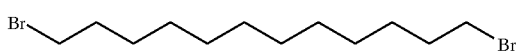
X-194 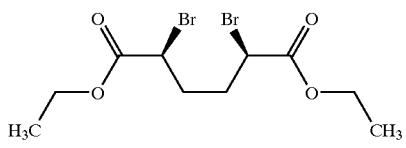
X-195 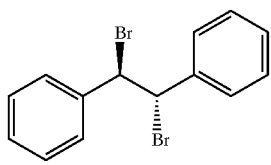
X-196 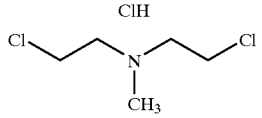
X-197 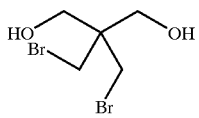
X-198 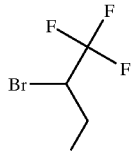
X-199 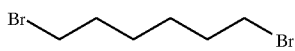
X-200 
X-201 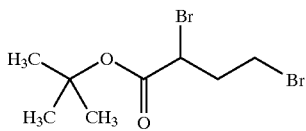
X-202 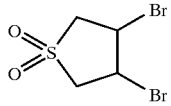
X-203 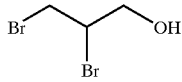
X-204 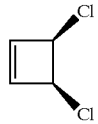
X-205 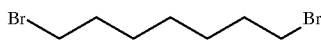
X-206 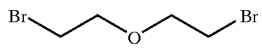
X-207 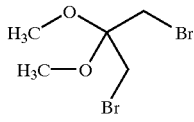
X-208 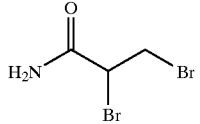
X-209 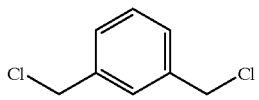
X-210 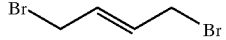
X-211 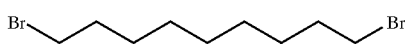
X-212 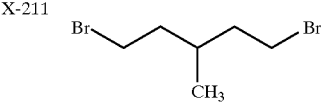
X-213 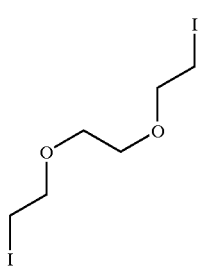
X-214 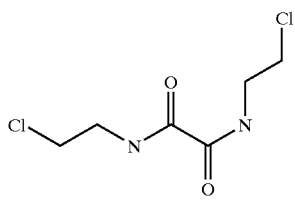
Diisocyanates -continued
X-215
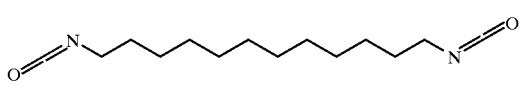
X-216
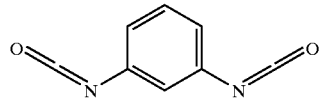
X-217
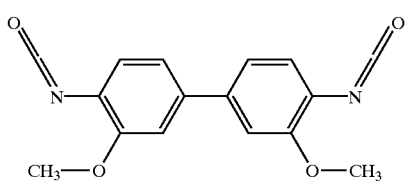
X-218
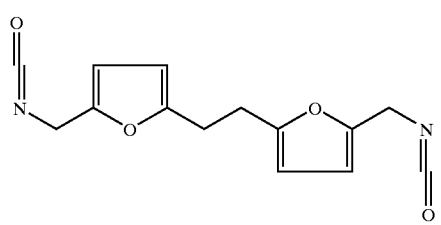
X-219
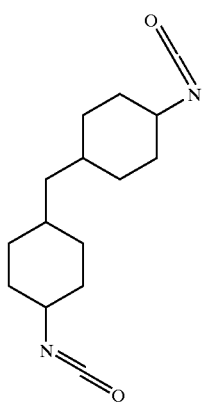
X-220
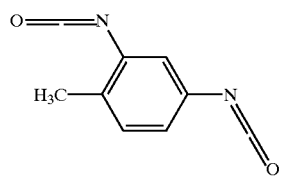
X-221
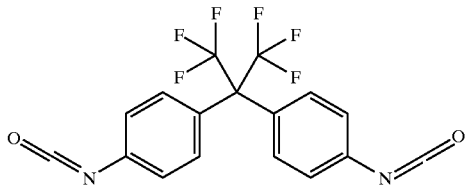
X-222
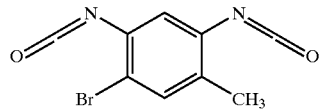
X-223
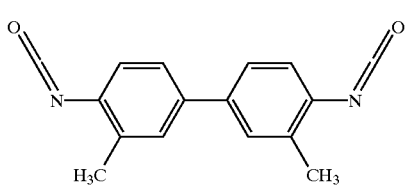
X-224
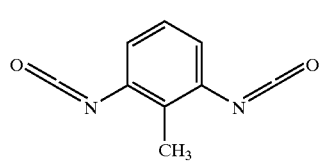
X-225
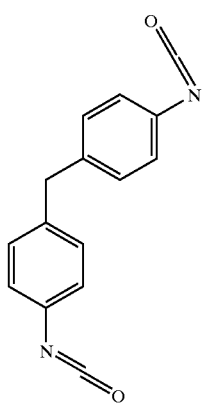
X-226
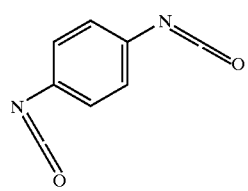

-continued
X-227 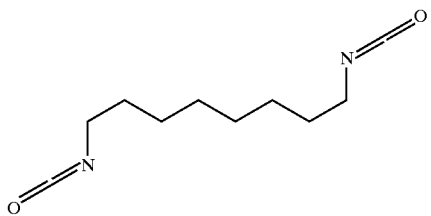
X-228 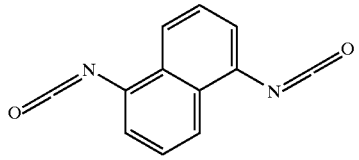
X-229 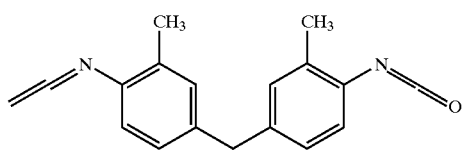
X-230 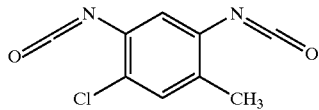
X-231 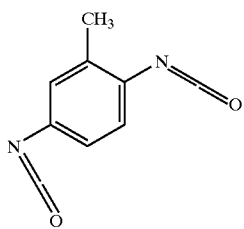
X-232 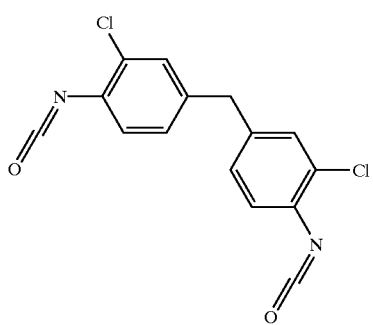
X-233 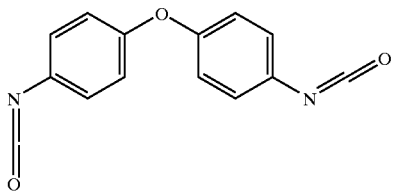
X-234 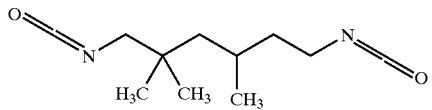
X-235 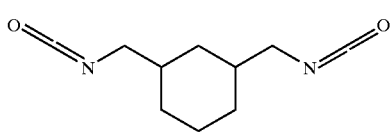
X-236 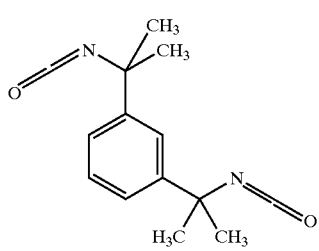
X-237
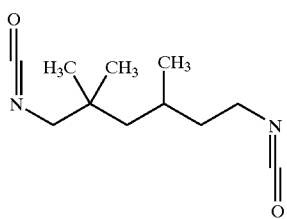 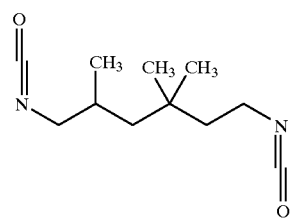

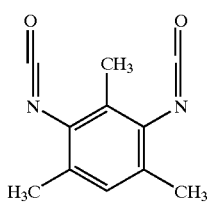
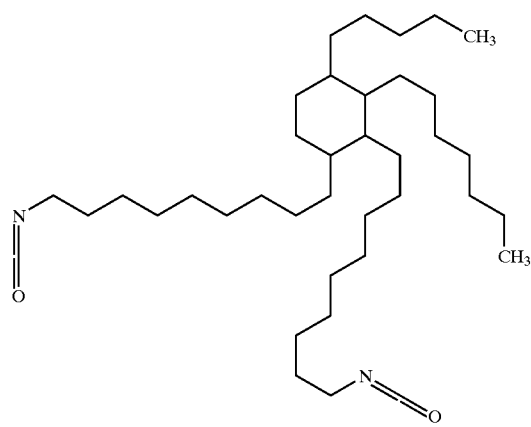
X-239
X-240 X-241
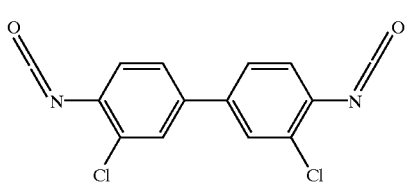
X-242 X-243
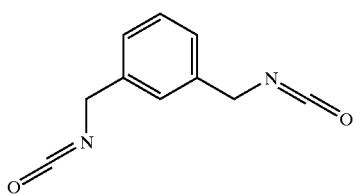
X-244 X-245
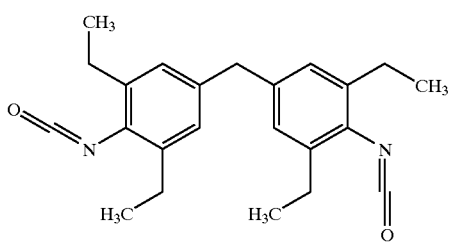
X-246 X-247
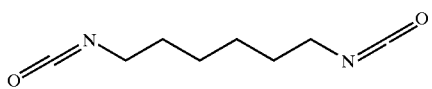
X-248
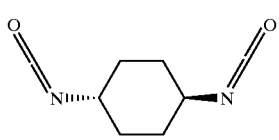
Diamines -continued
X-249
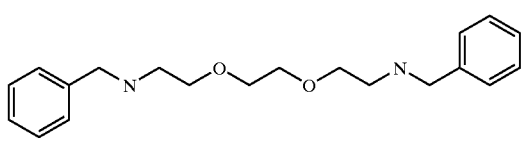
X-250
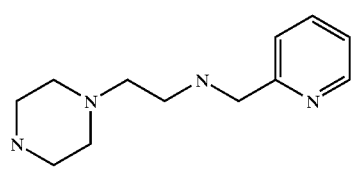
X-251
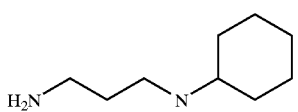
X-252
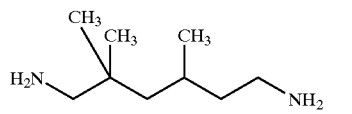
X-253
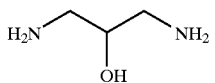
X-254
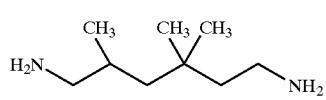
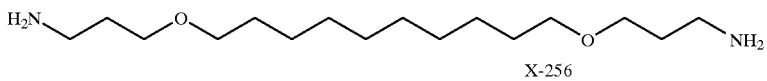
X-255
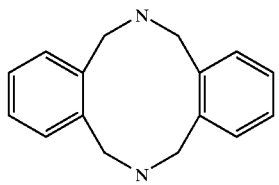
X-256
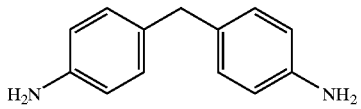
X-257
X-258
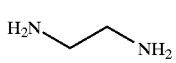
X-259
X-260
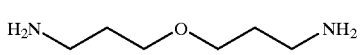
X-261
X-262
X-263
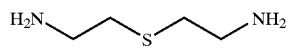
X-264
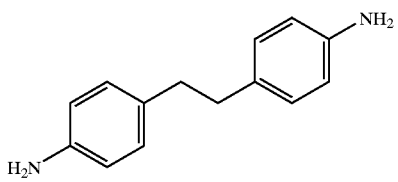
X-265
X-266
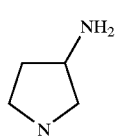
X-267
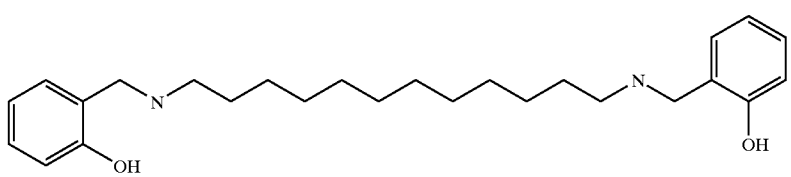

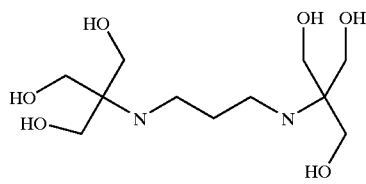
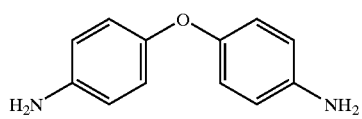
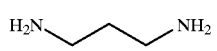
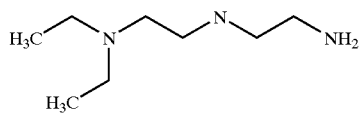
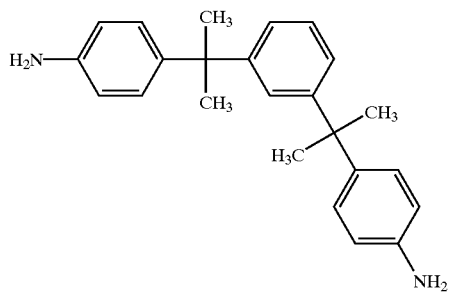
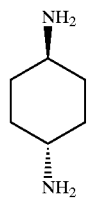
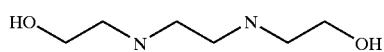
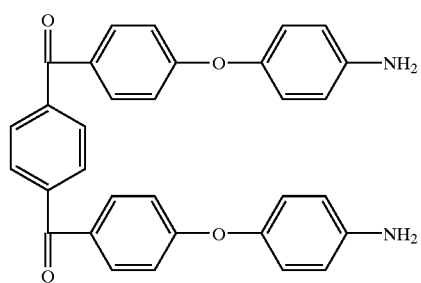
-continued
X-268 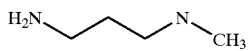 X-269
X-270 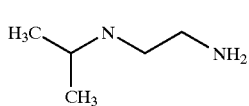 X-271
X-272 X-273
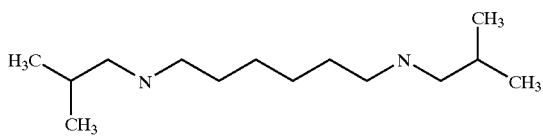
X-274 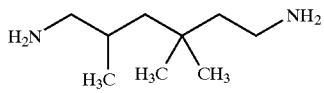 X-275
X-276 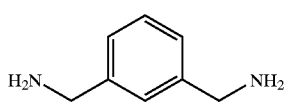 X-277
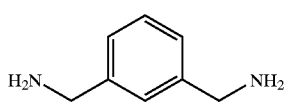
X-278 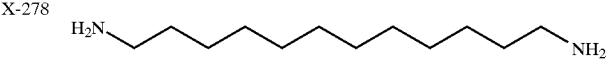 X-279
X-280 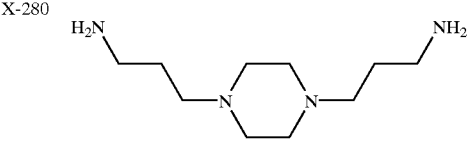 X-281
X-282 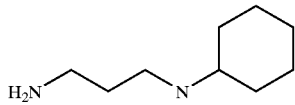 X-283

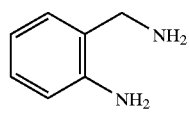
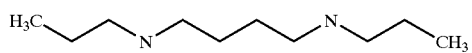
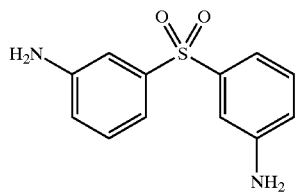
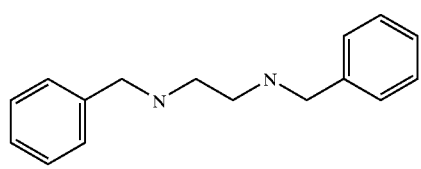
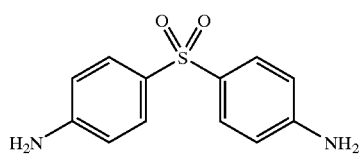
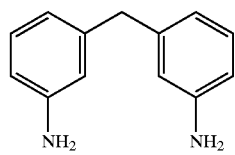
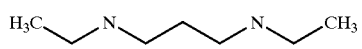
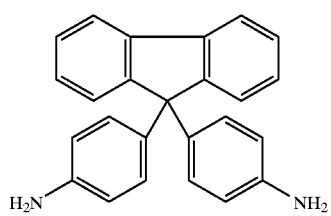
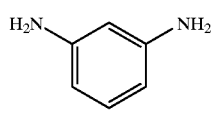
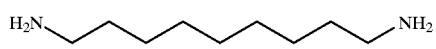
-continued
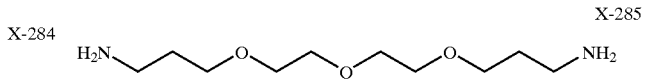
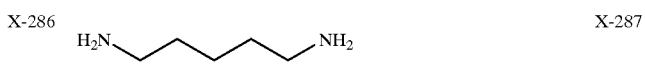
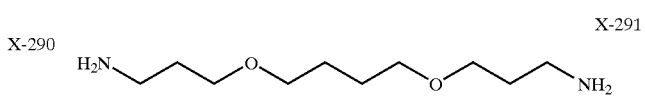
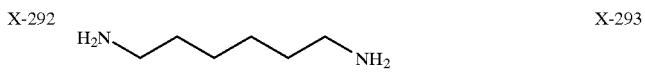
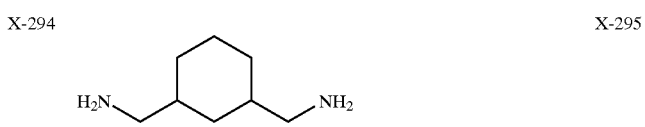
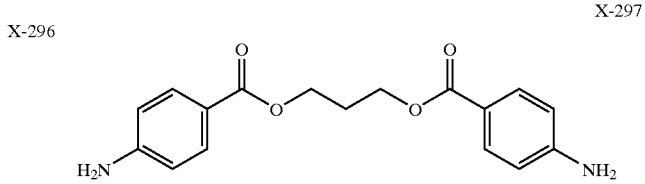
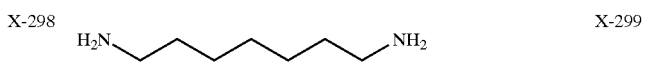
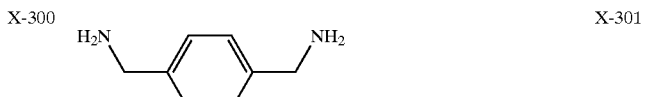
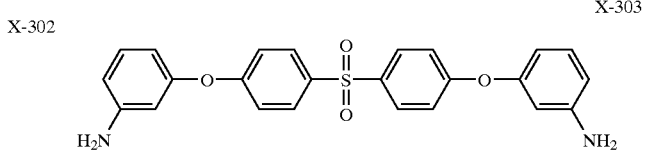
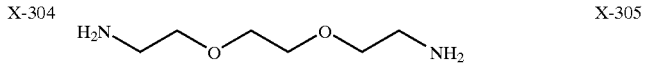

-continued
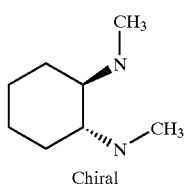
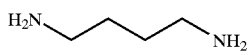 X-306 X-307
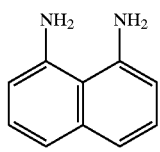
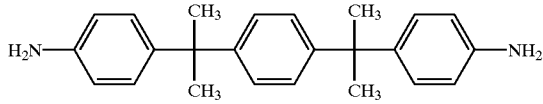 X-308 X-309
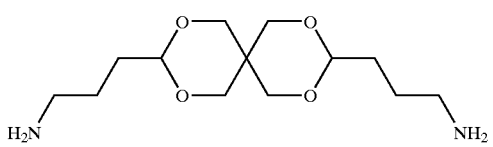
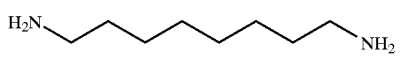 X-310 X-311
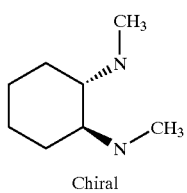
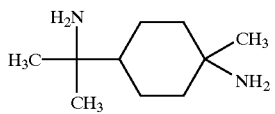 X-312 X-313
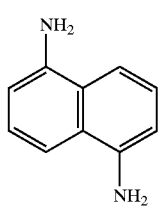
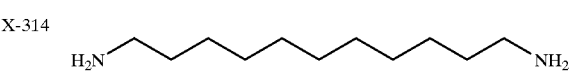 X-314 X-315
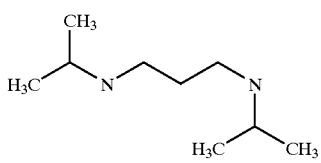
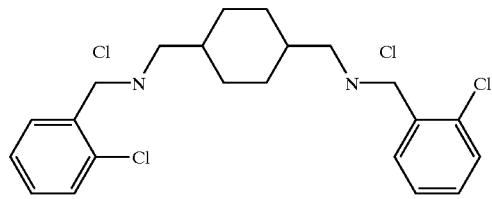 X-316 X-317
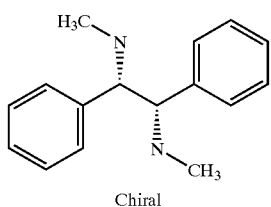
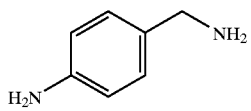 X-318 X-319
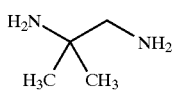
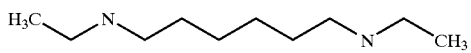 X-320 X-321
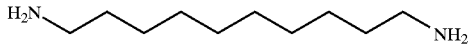
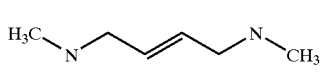 X-322 X-323
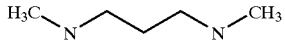
Diols
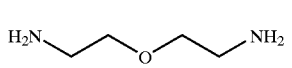 X-324 X-325

-continued
X-326
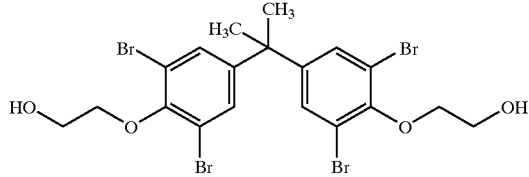
X-327
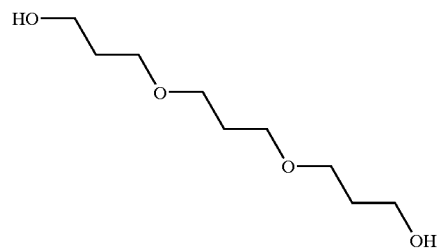
X-328
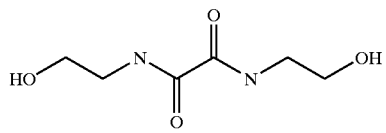
X-329
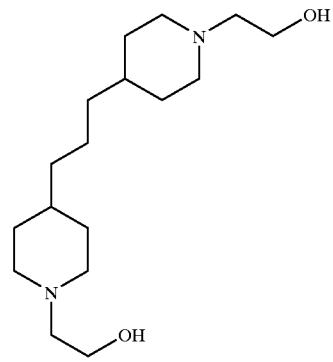
X-330
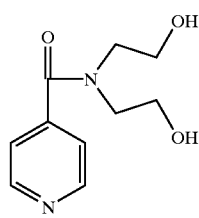
X-331
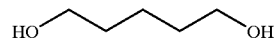
X-332
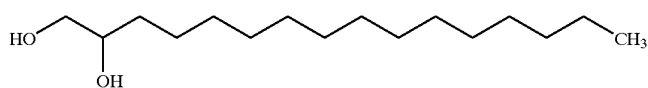
X-333
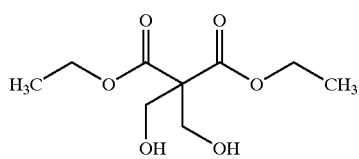
X-334
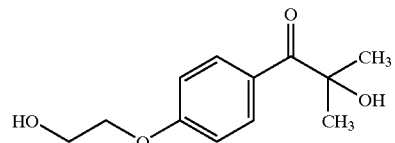
X-335
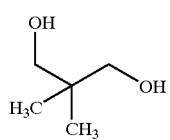
X-336
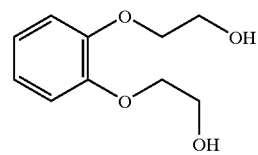
X-337
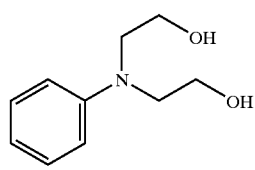
X-338
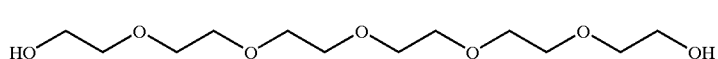

-continued

X-359 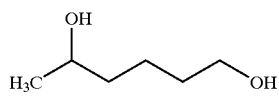
X-360 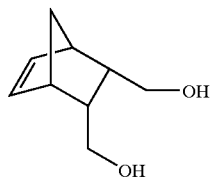
X-361 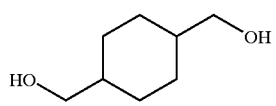
X-362 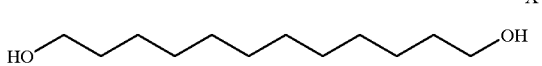
X-363 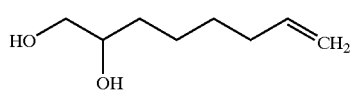
X-364 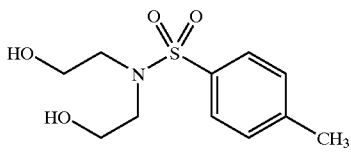
X-365 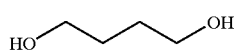
X-366 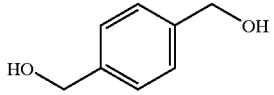
X-367 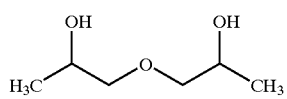
X-368 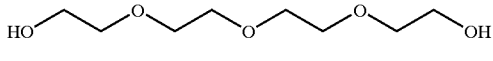
X-369 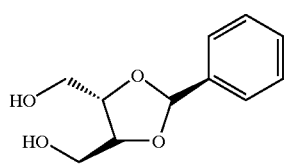
X-370 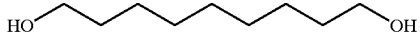
X-371 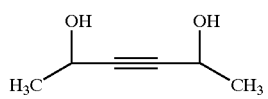
X-372 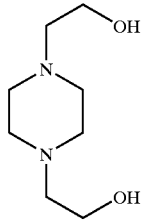
X-373 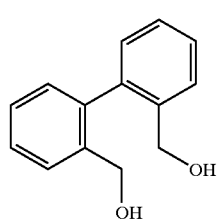
X-374 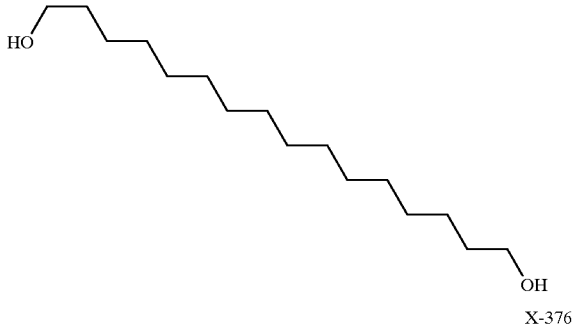
X-375 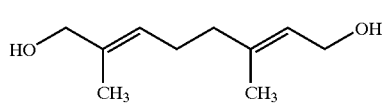
X-376 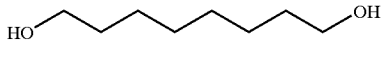

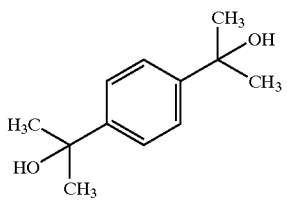
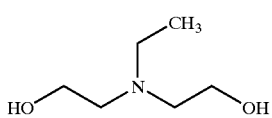
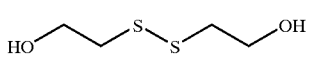
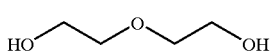
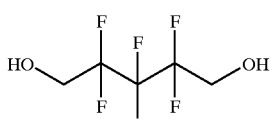
Dithiols
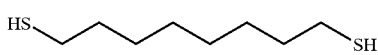
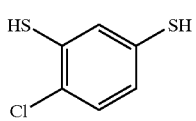
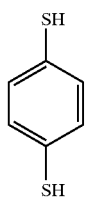
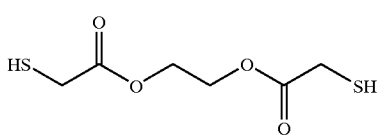
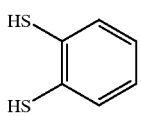
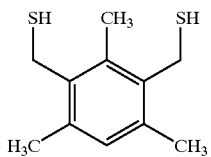
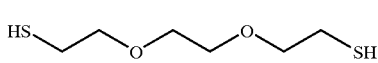
-continued
X-377 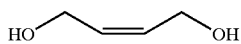 X-378
X-379 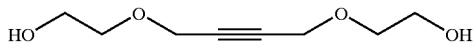 X-380
X-381 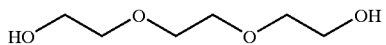 X-382
X-383  X-384
X-385
X-386 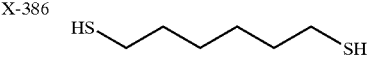 X-387
X-388  X-389
X-390 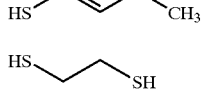 X-391
X-392 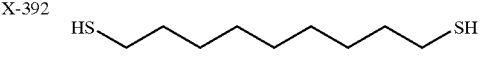 X-393
X-394 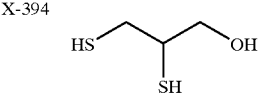 X-395
X-396 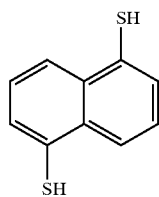 X-397
X-398 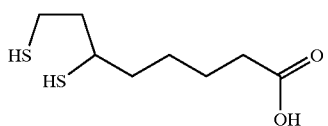 X-399

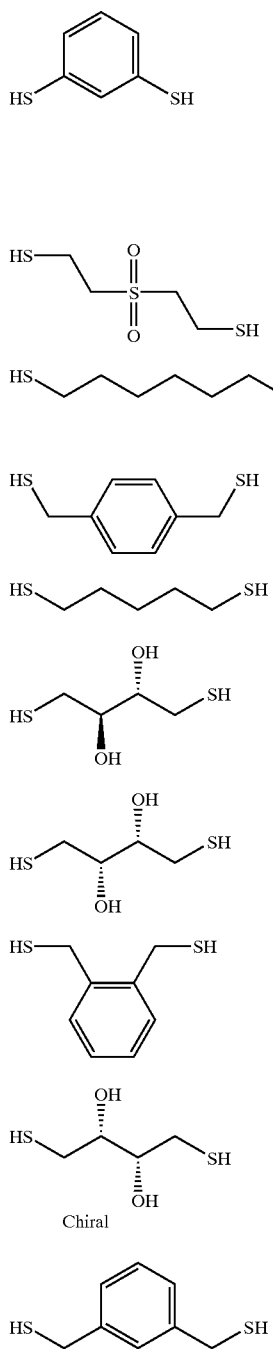

Representative ligands for use in this invention include, by way of example, L-1 and L-2 as identified above wherein L-1 is selected from a compound of formula (a) and L-2 is selected from a compound of formula (b).

Combinations of ligands (L) and linkers (X) per this invention include, by way example only, homo- and hetero-dimers wherein a first ligand is selected from L-1 and the second ligand and linker is selected from the following:

| | | | | | |
|---|---|---|---|---|---|
| L-2/X-1- | L-2/X-2- | L-2/X-3- | L-2/X-4- | L-2/X-5- | L-2/X-6- |
| L-2/X-7- | L-2/X-8- | L-2/X-9- | L-2/X-10- | L-2/X-11- | L-2/X-12- |
| L-2/X-13- | L-2/X-14- | L-2/X-15- | L-2/X-16- | L-2/X-17- | L-2/X-18- |
| L-2/X-19- | L-2/X-20- | L-2/X-21- | L-2/X-22- | L-2/X-23- | L-2/X-24- |

-continued

| | | | | | |
|---|---|---|---|---|---|
| L-2/X-25- | L-2/X-26- | L-2/X-27- | L-2/X-28- | L-2/X-29- | L-2/X-30- |
| L-2/X-31- | L-2/X-32- | L-2/X-33- | L-2/X-34- | L-2/X-35- | L-2/X-36- |
| L-2/X-37- | L-2/X-38- | L-2/X-39- | L-2/X-40- | L-2/X-41- | L-2/X-42- |
| L-2/X-43- | L-2/X-44- | L-2/X-45- | L-2/X-46- | L-2/X-47- | L-2/X-48- |
| L-2/X-49- | L-2/X-50- | L-2/X-51- | L-2/X-52- | L-2/X-53- | L-2/X-54- |
| L-2/X-55- | L-2/X-56- | L-2/X-57- | L-2/X-58- | L-2/X-59- | L-2/X-60- |
| L-2/X-61- | L-2/X-62- | L-2/X-63- | L-2/X-64- | L-2/X-65- | L-2/X-66- |
| L-2/X-67- | L-2/X-68- | L-2/X-69- | L-2/X-70- | L-2/X-71- | L-2/X-72- |
| L-2/X-73- | L-2/X-74- | L-2/X-75- | L-2/X-76- | L-2/X-77- | L-2/X-78- |
| L-2/X-79- | L-2/X-80- | L-2/X-81- | L-2/X-82- | L-2/X-83- | L-2/X-84- |
| L-2/X-85- | L-2/X-86- | L-2/X-87- | L-2/X-88- | L-2/X-89- | L-2/X-90- |
| L-2/X-91- | L-2/X-92- | L-2/X-93- | L-2/X-94- | L-2/X-95- | L-2/X-96- |
| L-2/X-97- | L-2/X-98- | L-2/X-99- | L-2/X-100- | L-2/X-101- | L-2/X-102- |
| L-2/X-103- | L-2/X-104- | L-2/X-105- | L-2/X-106- | L-2/X-107- | L-2/X-108- |
| L-2/X-109- | L-2/X-110- | L-2/X-111- | L-2/X-112- | L-2/X-113- | L-2/X-114- |
| L-2/X-115- | L-2/X-116- | L-2/X-117- | L-2/X-118- | L-2/X-119- | L-2/X-120- |
| L-2/X-121- | L-2/X-122- | L-2/X-123- | L-2/X-124- | L-2/X-125- | L-2/X-126- |
| L-2/X-127- | L-2/X-128- | L-2/X-129- | L-2/X-130- | L-2/X-131- | L-2/X-132- |
| L-2/X-133- | L-2/X-134- | L-2/X-135- | L-2/X-136- | L-2/X-137- | L-2/X-138- |
| L-2/X-139- | L-2/X-140- | L-2/X-141- | L-2/X-142- | L-2/X-143- | L-2/X-144- |
| L-2/X-145- | L-2/X-146- | L-2/X-147- | L-2/X-148- | L-2/X-149- | L-2/X-150- |
| L-2/X-151- | L-2/X-152- | L-2/X-153- | L-2/X-154- | L-2/X-155- | L-2/X-156- |
| L-2/X-157- | L-2/X-158- | L-2/X-159- | L-2/X-160- | L-2/X-161- | L-2/X-162- |
| L-2/X-163- | L-2/X-164- | L-2/X-165- | L-2/X-166- | L-2/X-167- | L-2/X-168- |
| L-2/X-169- | L-2/X-170- | L-2/X-171- | L-2/X-172- | | |
| L-2/X-173- | L-2/X-174- | L-2/X-175- | L-2/X-176- | L-2/X-177- | L-2/X-178- |
| L-2/X-179- | L-2/X-180- | L-2/X-181- | L-2/X-182- | L-2/X-183- | L-2/X-184- |
| L-2/X-185- | L-2/X-186- | L-2/X-187- | L-2/X-188- | L-2/X-189- | L-2/X-190- |
| L-2/X-191- | L-2/X-192- | L-2/X-193- | L-2/X-194- | L-2/X-195- | L-2/X-196- |
| L-2/X-197- | L-2/X-198- | L-2/X-199- | L-2/X-200- | L-2/X-201- | L-2/X-202- |
| L-2/X-203- | L-2/X-204- | L-2/X-205- | L-2/X-206- | L-2/X-207- | L-2/X-208- |
| L-2/X-209- | L-2/X-210- | L-2/X-211- | L-2/X-212- | L-2/X-213- | L-2/X-214- |
| L-2/X-215- | L-2/X-216- | L-2/X-217- | L-2/X-218- | L-2/X-219- | L-2/X-220- |
| L-2/X-221- | L-2/X-222- | L-2/X-223- | L-2/X-224- | L-2/X-225- | L-2/X-226- |
| L-2/X-227- | L-2/X-228- | L-2/X-229- | L-2/X-230- | L-2/X-231- | L-2/X-232- |
| L-2/X-233- | L-2/X-234- | L-2/X-235- | L-2/X-236- | L-2/X-237- | L-2/X-238- |
| L-2/X-239- | L-2/X-240- | L-2/X-241- | L-2/X-242- | L-2/X-243- | L-2/X-244- |
| L-2/X-245- | L-2/X-246- | L-2/X-247- | L-2/X-248- | L-2/X-249- | L-2/X-250- |
| L-2/X-251- | L-2/X-252- | L-2/X-253- | L-2/X-254- | L-2/X-255- | L-2/X-256- |
| L-2/X-257- | L-2/X-258- | L-2/X-259- | L-2/X-260- | L-2/X-261- | L-2/X-262- |
| L-2/X-263- | L-2/X-264- | L-2/X-265- | L-2/X-266- | L-2/X-267- | L-2/X-268- |
| L-2/X-269- | L-2/X-270- | L-2/X-271- | L-2/X-272- | L-2/X-273- | L-2/X-274- |
| L-2/X-275- | L-2/X-276- | L-2/X-277- | L-2/X-278- | L-2/X-279- | L-2/X-280- |
| L-2/X-281- | L-2/X-282- | L-2/X-283- | L-2/X-284- | L-2/X-285- | L-2/X-286- |
| L-2/X-287- | L-2/X-288- | L-2/X-289- | L-2/X-290- | L-2/X-291- | L-2/X-292- |
| L-2/X-293- | L-2/X-294- | L-2/X-295- | L-2/X-296- | L-2/X-297- | L-2/X-298- |
| L-2/X-299- | L-2/X-300- | L-2/X-301- | L-2/X-302- | L-2/X-303- | L-2/X-304- |
| L-2/X-305- | L-2/X-306- | L-2/X-307- | L-2/X-308- | L-2/X-309- | L-2/X-310- |
| L-2/X-311- | L-2/X-312- | L-2/X-313- | L-2/X-314- | L-2/X-315- | L-2/X-316- |
| L-2/X-317- | L-2/X-318- | L-2/X-319- | L-2/X-320- | L-2/X-321- | L-2/X-322- |
| L-2/X-323- | L-2/X-324- | L-2/X-325- | L-2/X-326- | L-2/X-327- | L-2/X-328- |
| L-2/X-329- | L-2/X-330- | L-2/X-331- | L-2/X-332- | L-2/X-333- | L-2/X-334- |
| L-2/X-335- | L-2/X-336- | L-2/X-337- | L-2/X-338- | L-2/X-339- | L-2/X-340- |
| L-2/X-341- | L-2/X-342- | L-2/X-343- | L-2/X-344- | L-2/X-345- | L-2/X-346- |
| L-2/X-347- | L-2/X-348- | L-2/X-349- | L-2/X-350- | L-2/X-351- | L-2/X-352- |
| L-2/X-353- | L-2/X-354- | L-2/X-355- | L-2/X-356- | L-2/X-357- | L-2/X-358- |
| L-2/X-359- | L-2/X-360- | L-2/X-361- | L-2/X-362- | L-2/X-363- | L-2/X-364- |
| L-2/X-365- | L-2/X-366- | L-2/X-367- | L-2/X-368- | L-2/X-369- | L-2/X-370- |
| L-2/X-371- | L-2/X-372- | L-2/X-373- | L-2/X-374- | L-2/X-375- | L-2/X-376- |
| L-2/X-377- | L-2/X-378- | L-2/X-379- | L-2/X-380- | L-2/X-381- | L-2/X-382- |
| L-2/X-383- | L-2/X-384- | L-2/X-385- | L-2/X-386- | L-2/X-387- | L-2/X-388- |
| L-2/X-389- | L-2/X-390- | L-2/X-391- | L-2/X-399- | L-2/X-393- | L-2/X-394- |
| L-2/X-395- | L-2/X-396- | L-2/X-397- | L-2/X-398- | L-2/X-399- | L-2/X-400- |
| L-2/X-401- | L-2/X-402- | L-2/X-403- | L-2/X-404- | L-2/X-405- | L-2/X-406- |
| L-2/X-407- | L-2/X-408- | L-2/X-409- | L-2/X-410- | L-2/X-411- | L-2/X-412- |
| L-2/X-413- | L-2/X-414- | L-2/X-415- | L-2/X-416- | L-2/X-417- | L-2/X-418- | and so on.

Utility, Testing, and Administration

Utility

The multibinding compounds of this invention are β2 adrenergic receptor agonists. Accordingly, the multibinding compounds and pharmaceutical compositions of this invention are useful in the treatment and prevention of diseases mediated by β2 adrenergic receptor such as asthma, bronchitis, and the like. They are also useful in the treatment of nervous system injury and premature labor. It is also contemplated that the multibinding compounds of this invention are useful for the treatment of metabolic disorders such as obesity, diabetes, and the like.

Testing

The β2 adrenergic receptor agonistic activity of the compounds of formula (I) to may be demonstrated by a variety of in vitro assays known to those of ordinary skill in the art, such as the assay described in the biological examples 1 and 2. It may also be assayed by the Ex vivo assays described in Ball, D. I. et al., "Salmterol a Novel, Long-acting beta 2-Adrenergic Agonist: Characterization of Pharmacological Activity in Vitro and in Vivo" Br. J. Pharmacol., 104, 665–671 (1991); Linden, A. et al., "Sameterol, Formoterol, and Salbutamol in the Isolated Guinea-Pig Trachea: Differences in Maximum Relaxant Effect and Potency but not in Functional Atagonism. Thorax, 48, 547–553, (1993); and Bials, A. T. et al., Inventigations into Factors Determining the Duration of Action of the Beta 2-Adrenoceptor Agonist, Salmateroal. Br. J. Pharmacol., 108, 505–515 (1993); or in vivo assays such as those described in Ball, D. I. et al., "Salmterol a Novel, Long-acting beta 2-Adrenergic Agonist: Characterization of Pharmacological Activity in Vitro and in Vivo" Br. J. Pharmacol., 104, 665–671 (1991); Kikkawa, H. et al., "RA-2005, a Novel, Long-acting, and Selective Beta 2-Adrenoceptor Agonist: Characterization of its in vivo Bronchodilating Action in Guinea Pigs and Cats in Comparison with other Beta 2-Agonists". Biol. Pharm. Bull., 17, 1047–1052, (1994); and Anderson, G. P., "Formeterol: Pharmacology, Colecular basis of Agonism and Mechanism of Long Duration of a Highly Potent and Selective Beta 2-Adrenoceptor Agonist Bronchodilator, Life Sciences, 52, 2145–2160, (1993).

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as injectable, intranasal, and oral compositions. Such compositions are prepared in a manner well known in the pharmaceutical art and comprise at least one active compound.

This invention also includes pharmaceutical compositions which contain as the active ingredient, one or more of the compounds described herein associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick sustained or delayed release of the active ingredient after administration to the patient by employing procedures known in the art.

The compositions are preferably formulated in a unit dosage form, each dosage containing from about 0.001 to about 1 g, more usually about 1 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of Formula (I) above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

EXAMPLES

The following preparations and examples are given to enable those skilled in the art to more clearly understand and to practice the present invention. They should not be considered as limiting the scope of the invention, but merely as being illustrative and representative thereof.

In the examples below, the following abbreviations have the following meanings. Unless otherwise stated, all temperatures are in degrees Celsius. If an abbreviation is not defined, it has its generally accepted meaning.

| | |
|---|---|
| Å = | Angstroms |
| cm = | centimeter |
| DCC = | dicyclohexyl carbodiimide |
| DMF = | N,N-dimethylformamide |
| DMSO = | dimethylsulfoxide |
| g = | gram |
| HPLC = | high performance liquid chromatography |
| MEM = | minimal essential medium |
| mg = | milligram |
| MIC = | minimum inhibitory concentration |
| min = | minute |
| mL = | milliliter |
| mm = | millimeter |
| mmol = | millimol |
| N = | normal |
| THF = | tetrahydrofuran |
| µL = | microliters |
| µm = | microns |

SYNTHETIC EXAMPLES

Example 1

Synthesis of a Bivalent Multibinding Compound of Formula (I) Where $Ar^1$ and $Ar^2$ are 4-Hydroxy-3-hydroxymethylphenyl, $R^1$–$R^3$ and $R^{11}$–$R^{13}$ are Hydrogen and the Ligand is —$(CH_2)_3$—O—$(CH_2)_2O]_{73-74}$—$(CH_2)_3$—

Step 1

To a solution of 5-acetylsalicylic acid methyl ester (5.0 g, 25.7 mmole) in dimethylsulfoxide (44 mL) was added 48% hydrobromic acid. The resulting mixture was stirred at 55° C. for 24 h, and poured into a slurry of ice-water (~200 mL), precipitating a pale yellow solid. The solid was filtered, washed with water (200 mL), and dried to give α,α-dihydroxy-4-hydroxy-3-methoxycarbonyl-acetophenone. The product was re-suspended in ethyl ether (~200 mL), filtered and dried to give (3.41 g, 59%) of pure product. $R_f$=0.8 (10% MeOH/$CH_2Cl_2$). $H^1$-NMR (4/1 $CDCl_3$/$CD_3OD$, 299.96 MHz): d (ppm) 8.73–8.72 (d, 1H), 8.28–8.24 (dd, 1H), 7.08–7.05 (d, 1H), 5.82 (s, 1H), 4.01 (s, 3H).

Step 2

To a suspension of α,α-dihydroxy-4-hydroxy-3-methoxycarbonyl-acetophenone (0.3 g, 1.33 mmole) in THF (10 mL) was added a solution of PEG-diamine, $NH_2(CH_2)_3O(CH_2CH_2O)_n(CH_2)_3NH_2$ (0.225 g, 0.066 mmol) (MW~3400; N=73–74; Shearwater Polymers, Inc.). The resulting suspension was stirred for 4 h at ambient temperature under nitrogen atmosphere. After cooling of the resulting solution in an ice bath, 2M borane dimethylsulfide solution in tetrahydrofuran (0.4 mL, 0.8 mmol) was added to the cooled reaction mixture. The resulting mixture was slowly warmed to room temperature and refluxed for 4 h under nitrogen atmosphere. The reaction mixture was cooled and methanol (1 mL) was added to the reaction mixture to quench the excess borane. After 30 min., of stirring at room temperature the solution was concentrated in vacuo to give a pale brown solid. The solid was washed with ethyl acetate and hexane mixture (1:2.5 mL) and then dried. The crude product was dissolved in water (3 mL) and purified by reverse phase preparative HPLC (using 20 to 60% acetonitrile/water mixture with 0.1% trifluoroacetic acid, flow rate=20 mL/min) and the desired product was collected.

$H^1$-NMR ($CD_3OD$, 299.96 MHz): δ (ppm) 7.18 (br s, 2H), 7.12–7.09 (br d, 2H), 6.79–6.77 (br d, 2H), 4.80–4.78 (m, 2H), 3.76–3.30 (br m, ~296H), 3.18–3.08 (br m, 8H), 1.84 (m, 4H).

Compound 2:

Proceeding as described above but substituting PEG-diamine, $NH_2(CH_2)_3O(CH_2CH_2O)_n(CH_2)_3NH_2$ with a Jeffamine of formula $CH_3CH(NH_2)(CH_2)[OCH(CH_3)CH_2]_nOCH_2CH(CH_3)NH$, (n=4–5) gave the desired compound where the linker is —$CH(CH_3)(CH_2)[OCH(CH_3)CH_2]_nOCH_2CH(CH_3)$—.

$H^1$-NMR ($CD_3OD$, 299.96 MHz): δ (ppm) 7.36 (br s, 2H), 7.19–7.16 (br dd, 2H), 6.81–6.78 (br s, 2H), 4.68 (s, 4H), 3.84 –3.36 (m), 3.28–3.14 (m, 4H), 136–1.32 (m, 6H), 1.20–1.08 (m, ~15H); ESMS: n=4; obsd. 697.7 $[M+H]^+$, 350.1 $[M+2H]^{2+}$;: n=5; obsd. 755.7 $[M+H]^+$, 378.5 $[M+2H]^{2+}$.

Compound 3:

Proceeding as described above but substituting PEG-diamine, $NH_2(CH_2)_3O(CH_2CH_2O)_n(CH_2)_3NH_2$ with a Jef-

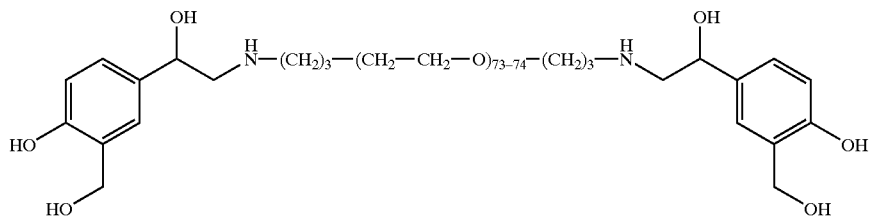

famine of formula $CH_3CH(NH_2)(CH_2)[OCH(CH_3)CH_2]_nOCH_2CH(CH_3)NH_2$ (n=5–6) gave the desired compound where the linker is $—CH(CH_3)(CH_2)[OCH(CH_3)CH_2]_nOCH_2CH(CH_3)—$. ESMS: n=5; obsd. 755.7 $[M+H]^+$, 379.6 $[M+2H]^{2+}$; n=6; obsd. 813.7 $[M+H]^+$, 407.5 $[M+2H]^{2+}$.

Compound 4:

Proceeding as described above but substituting PEG-diamine, $NH_2(CH_2)_3O(CH_2CH_2O)_n(CH_2)_3NH_2$ with a Jeffamine of formula $CH_3CH(NH_2)(CH_2)[OCH(CH_3)CH_2]_nOCH_2CH(CH_3)NH_2$ (n=7–9) gave the desired compound where the linker is $—CH(CH_3)(CH_2)[OCH(CH_3)CH_2]_nOCH_2CH(CH_3)—$. ESMS: n=7; obsd. 871.8 $[M+H]^+$, 436.3 $[M+2H]^{2+}$; n=8; obsd. 929.6 $[M+H]^+$, 465.6 $[M+2H]^{2+}$; n=9; obsd. 988.0 $[M+H]^+$, 494.1 $[M+2H]^{2+}$.

Compound 5:

Proceeding as described above but substituting PEG-diamine, $NH_2(CH_2)_3O(CH_2CH_2O)_n(CH_2)_3NH_2$ with 3,6-dioxa-1,8-octanediamine $NH_2(CH_2)_2O(CH_2)_2O(CH_2)_2NH_2$ gave the desired compound where the linker is $—(CH_2)_2O(CH_2)_2O(CH_2)_2—$.

$H^1$-NMR ($CD_3OD$, 299.96 MHz): δ (ppm) 7.34 (d, 2H), 7.17–7.14 (dd, 1H), 6.80–6.76 (d, 2H), 4.65 (s, 4H), 3.79–3.56 (m, 8H), 3.30–3.11 (m, 8H); ESMS ($C_{24}H_{36}N_2O_8$): calcd. 480.52, obsd. 481.3 $[M+H]^+$, 503.5 $[M+Na]^+$.

Compound 6:

Proceeding as described above but substituting PEG-diamine, $NH_2(CH_2)_3O(CH_2CH_2O)_n(CH_2)_3NH$, with 4,7,10-trioxa-1,13-tridecanediamine $NH_2(CH_2)_3O[(CH_2)_2O]_2(CH_2)_3NH_2$ gave the desired compound where the linker is $—(CH_2)_3O[(CH_2)_2O]_2(CH_2)_3—$.

ESMS ($C_{28}H_{44}N_2O_6$): calcd. 552.6, obsd. 553.4 $[M+H]^+$, 576.1 $[M+Na]^+$.

Compound 7:

Proceeding as described above but substituting PEG-diamine, $NH_2(CH_2)_3O(CH_2CH_2O)_n(CH_2)_3NH_2$ with 4,9-dioxa-1,12-dodecanediamine $NH_2(CH_2)_3O(CH_2)_4O(CH_2)_3NH_2$ gave the desired compound where the linker is $—(CH_2)_3O(CH_2)_4O(CH_2)_3—$.

ESMS ($C_{28}H_{44}N_2O_6$): calcd. 552.6, obsd. 553.4 $[M+H]^+$, 576.1 $[M+Na]^+$. ESMS ($C_{28}H_{44}N_2O_8$): calcd. 536.6, obsd. 537.3 $[M+H]^+$, 560.3 $[M+Na]^+$.

Compound 8:

Proceeding as described above but substituting PEG-diamine, $NH_2(CH_2)_3O(CH_2CH_2O)_n(CH_2)_3NH_2$ with a Jeffamine of formula $CH_3CH(NH_2)(CH_2)[OCH(CH_3)CH_2]_6OCH_2CH(CH_3)NH_2$ gave the desired compound where the linker is $—CH(CH_3)(CH_2)[OCH(CH_3)CH_2]_7OCH_2CH(CH_3)—$. ESMS: obsd. 819.3 $[M+H]^+$.

Compound 9:

Proceeding as described above but substituting PEG-diamine, $NH_2(CH_2)_3O(CH_2CH_2O)_n(CH_2)_3NH_2$ with a Jeffamine of formula $CH_3CH(NH_2)(CH_2)[OCH(CH_3)CH_2]_7OCH_2CH(CH_3)NH_2$ gave the desired compound where the linker is $—CH(CH_3)(CH_2)[OCH(CH_3)CH_2]_7OCH_2CH(CH_3)—$. ESMS: obsd. 876.5 $[M+H]^+$.

Compound 10:

Proceeding as described above but substituting PEG-diamine, $NH_2(CH_2)_3O(CH_2CH_2O)_n(CH_2)_3NH_2$ with a Jeffamine of formula $CH_3CH(NH_2)(CH_2)[OCH(CH_3)CH_2]_nOCH_2CH(CH_3)NH_2$ (n=8–9) gave the desired compound where the linker is $—CH(CH_3)(CH_2)[OCH(CH_3)CH_2]_nOCH_2CH(CH_3)—$. ESMS: obsd. n=8; 932.8 $[M+H]^+$; n=9; 991.8 $[M+H]^+$.

FORMULATION EXAMPLES

Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Example 2

A tablet Formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly.

The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Example 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Example 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Example 8

A formulation may be prepared as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Example 9

A formulation may be prepared as follows:

| Ingredient | Quantity |
| --- | --- |
| Active Ingredient | 5.0 mg |
| Corn Oil | 1.0 mL |

Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Other suitable formulations for use in the present invention can be found in *Remington's Pharmaceutical Sciences*, edited by E. W. Martin (Mack Publishing Company, 18th ed., 1990).

BIOLOGICAL EXAMPLES

Example 1

β2-Adrenergic Receptor In Vitro Functional Assay

The β2-adrenergic receptor functional activity of compounds of the invention was tested follows.
Cell Seeding and Growth:
Primary bronchial smooth muscle cells from a 21 yr. old male (Clonetics, San Diego, Calif.) were seeded at 50,000 cells/well in 24-well tissue culture plates. The media used was Clonetic's SmBM-2 supplemented with hEGF, Insulin, hFGF, and Fetal Bovine Serum. Cells were grown two days at 37° C., 5% $CO_2$ until confluent monolayers were seen.

Agonist Stimulation of Cells

The media was aspirated from each well and replaced with 250 ml fresh media containing 1 mM IBMX, a phospodiesterase inhibitor (Sigma, St Louis, Mo.). Cells were incubated for 15 minutes at 37° C., and then 250 ml of agonist at appropriate concentration was added. Cells were then incubated for an additional 10 minutes. Media was aspirated and 500 ml cold 70% EtOH was added to cells, and then removed to an empty 96-well deep-well plate after about 5 minutes. This step was then repeated. The deep-well plate was then spun in a speed-vac until all EtOH dried off, leaving dry pellets. cAMP (pmol/well) was quantitated using a cAMP ELISA kit from Stratagene (La Jolla, Calif.). $EC_{50}$ curves were generated using the 4-parameter fit equation:

$$y=(a-d)/(1+(x/c)^b)+d,$$

where, y=cpm
a=total binding
c=$IC_{50}$
x=[compound]
d=NS binding
b=slope
Fix NS binding and allow all other parameters to float.

Example 2

β2-Adrenergic Receptor In Vitro Radioligand Binding Assay

The β1/2-adrenergic receptor binding activity of compounds of the invention can be tested follows. SF9 cell membranes containing either β1 or β32-adrenergic receptor (NEN, Boston, Mass.) were incubated with 0.07 nM $^{125}I$-iodocyanopindolol (NEN, Boston, Mass.) in binding buffer containing 75mM Tris-HCl (pH 7.4), 12.5 mM MgCl, and 2 mM EDTA and varying concentrations of test compounds or buffer only (control) in 96-well plates. The plates were incubated at room temperature with shaking for 1 hour. The receptor bound radioligand was harvested by filtration over 96-well GF/B filter plates (Packard, Meriden, Conn.) pre-blocked with 0.3% polyethylenimine and washed twice with 200 μl PBS using cell harvester. The filters were washed thrice with 200 μl PBS using cell harvester and then resuspended in 40 μl scintillation cocktail. The filter-bound radioactivity was measured with a scintillation counter and $IC_{50}$ curves are generated using the standard 4-parameter fit equation described above.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula (II):

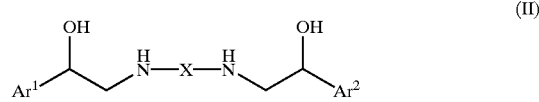

(II)

wherein:

$Ar^1$ is a phenyl ring of formula (c):

(c)

wherein:
$R^4$ is hydrogen, alkyl, halo, or alkoxy;.
$R^5$ is hydrogen, hydroxy, halo, amino, or —$NHSO_2R^a$ where $R^a$ is alkyl; and
$R^6$ is hydrogen, halo, alkoxy, substituted alkyl, sulfonylamino, aminoacyl, or acylamino;
X is selected from the group consisting of -(alkylene)-O—{(alkylene)-O—}$_n$-(alkylene)- (where n is an integer of from 0–9) and further wherein alkylene is —$(CH_2)_6$; and
Ar is either:
(i) a phenyl ring of formula (c'):

(c')

wherein:
$R^4$ is hydrogen, alkyl, halo, or alkoxy;
$R^5$ is hydrogen, hydroxy, halo, amino, or —$NHSO_2R^a$ where $R^a$ is alkyl; and
$R^6$ is hydrogen, halo, hydroxy, alkoxy, substituted alkyl, sulfonylamino, aminoacyl, or acylamino; or
(ii) a phenyl ring of formula (d):

(d)

wherein:
$R^7$ is hydrogen, alkyl, alkenyl, substituted alkyl, halo, alkoxy, substituted alkoxy, hydroxy, aminoacyl, or heteroaryl; and
$R^8$ is hydrogen, halo, alkoxy, substituted alkoxy, acylamino; or (iii) naphthyl, pyridyl, benzimidazol-1-yl, indolyl, 2-cyanoindolyl, carbazolyl, 4-methylindanyl, 5-(CH₃CO₂CH₂O—)-1,2,3,4-tetrahydronaphthyl, 1H-2oxoindole, 2,3,4-trihydrothianaphthalene, or 4-oxo-2,3-dihydrothianapthalene; or a pharmaceutically acceptable salt thereof.

2. A compound of formula II:

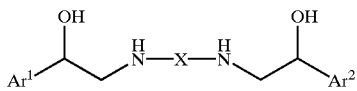

(II)

wherein:

Ar¹ is a phenyl ring of formula (c):

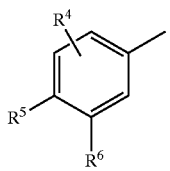

(c)

wherein:
$R^4$ is hydrogen, methyl, fluoro, chloro, methoxy;
$R^5$ is hydrogen, hydroxy, fluoro, chloro, amino, —NHSO₂CH₃; and
$R^6$ is hydrogen, chloro, fluoro, methoxy, hydroxymethyl, —CH₂SO₂CH₃, —NHSO₂CH₃, —NHCHO, —CONH₂, —NHCONH₂;

Ar² is either:
(i) a phenyl ring of formula (c'):

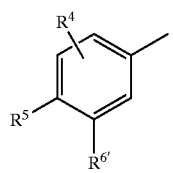

(c')

wherein:
$R^4$ is hydrogen, methyl, fluoro, chloro, methoxy;
$R^5$ is hydrogen, hydroxy, fluoro, chloro, amino, —NHSO₂CH₃; and
$R^6$ is hydrogen, chloro, fluoro, hydroxy, methoxy, hydroxymethyl, —CH₂SO₂CH₃, —NHSO₂CH₃, —NHCHO, —CONH₂, —NHCONH₂; or
(ii) a phenyl ring of formula (d):

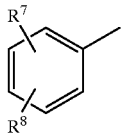

(d)

wherein:
$R^7$ is hydrogen, methyl, propen-2-yl, fluoro, chloro, methoxy, —CH₂CO₂Me, hydroxy, —CH₂CONH₂, —NHCOCH₃, imidazol-1-yl, or 1-methyl-4-trifluoromethyl-imidazol-2-yl; and
$R^8$ is hydrogen, fluoro, chloro, methoxy, —CH₂CO₂Me, or —CONH₂; or (iii) naphthyl, pyridyl, benzimidazol-1-yl, indolyl, 2yanoindolyl, carbazolyl, 4-methylindanyl, 5-(CH₃CO₂CH₂O—)-1,2,3,4-tetrahydronaphthyl, 1H-2-oxoindole, 2,3,4-trihydrothianaphthalene, or 4-oxo-2,3-dihydrothianapthalene; and X is selected from the group consisting of -(alkylene)-O—{(alkylene)-O—}ₙ-(alkylene)- (where n is an integer of from 0–9) and further wherein alkylene is —(CH₂)₆—.

3. A compound of Formula (II):

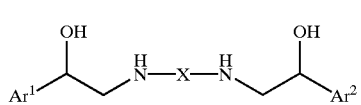

(II)

wherein:

Ar¹ is phenyl, 4-hydroxyphenyl, 3,4-dichlorophenyl, 2chloro-3,5-dihydroxyphenyl, 2-fluoro-3,5-dihydroxyphenyl, 4-hydroxy-3-methoxyphenyl, 4-hydroxy-3-hydroxymethylphenyl, 4-hydroxy-3-(HCONH—)phenyl, 4-hydroxy-3-(NH₂CO—)phenyl, 3-chlorophenyl, 2,5direthoxyphenyl, 4-(CH₃SO₂NH—)-phenyl, 4-hydroxy-3-(CH₃SO₂CH₂—)phenyl, 4-hydroxy-3-(CH₃SO₂NH—)phenyl, 4-hydroxy-3-(NH₂CONH—)phenyl, or 3,5-dichloro-4-aminophenyl;

X is selected from the group consisting of —(CH₂)₆—O—(CH₂)₆— and —(CH₂)₆—O—(CH₂)₆—O—(CH₂)₆—; and Ar² is:

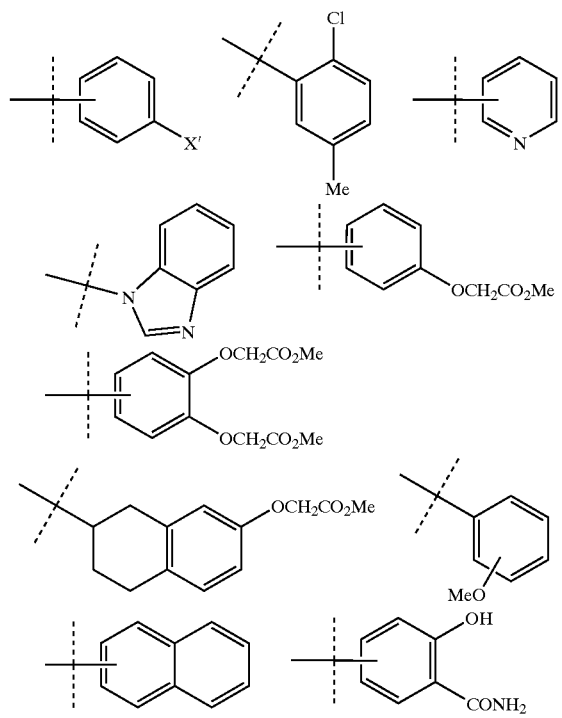

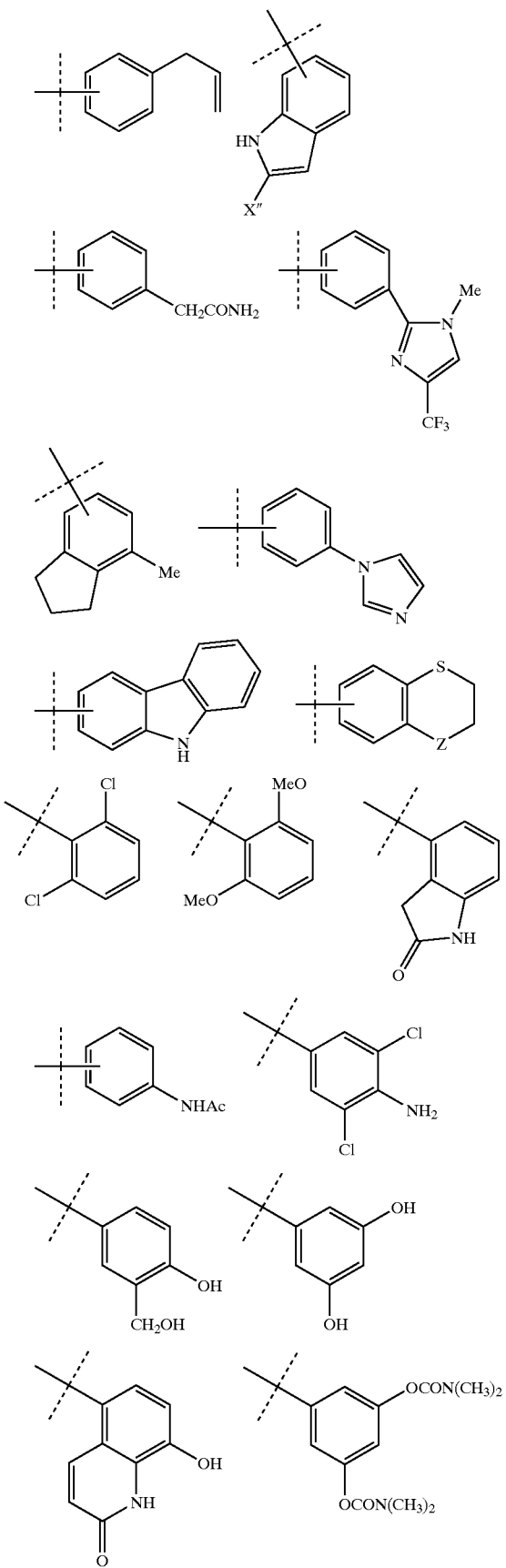
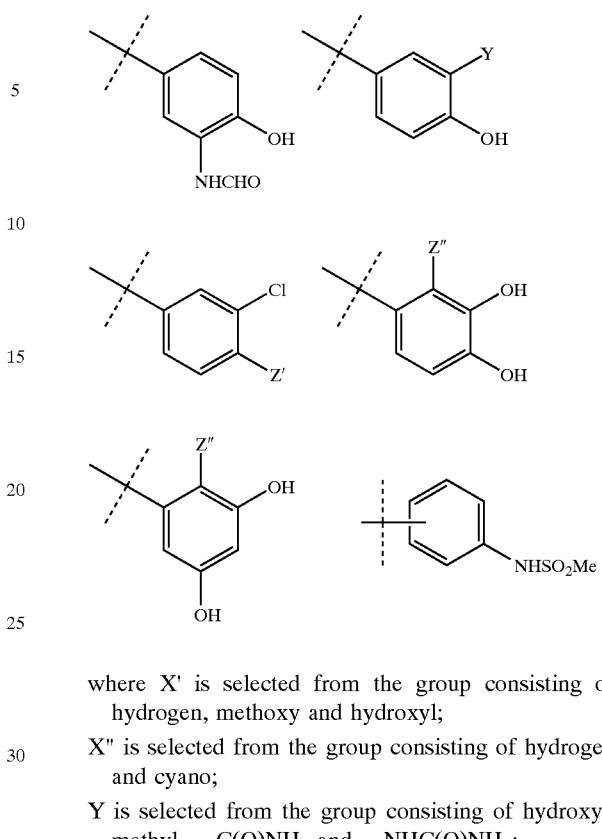

where X' is selected from the group consisting of hydrogen, methoxy and hydroxyl;

X" is selected from the group consisting of hydrogen and cyano;

Y is selected from the group consisting of hydroxyl, methyl, —C(O)NH$_2$ and —NHC(O)NH$_2$;

Z is selected from the group consisting of —O— and —CH$_2$—;

Z' is selected from the group consisting of chloro and hydrogen; and

Z" is selected from the group consisting of chloro and fluoro.

4. A pharmaceutical composition comprising a pharmaceutically acceptable carrier and an effective amount of a compound of claim 1.

5. A pharmaceutical composition comprising a pharmaceutically acceptable carrier and an effective amount of a compound of claim 3.

6. The compound according to claim 1 wherein X is selected from the group consisting of —(CH$_2$)$_6$—O—(CH$_2$)$_6$— and —(CH$_2$)$_6$—O—(CH$_2$)$_6$—O—(CH$_2$)$_6$—.

7. A compound of the formula:

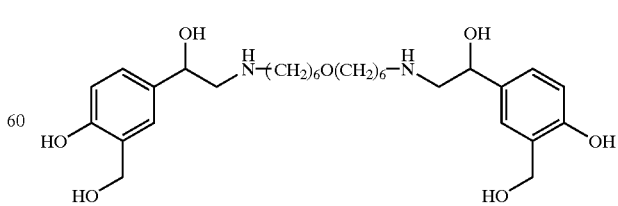

or a pharmaceutically acceptable salt thereof.

8. A compound of the formula:
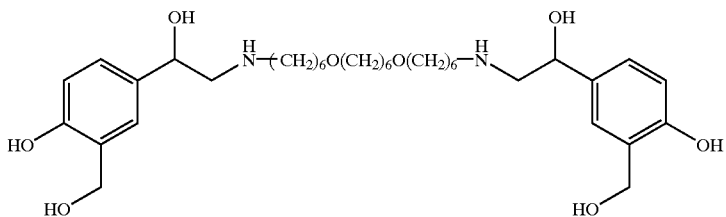
or a pharmaceutically acceptable salt thereof.
* * * * *

UNITED STATES PATENT AND TRADEMARK OFFICE
CERTIFICATE OF CORRECTION

PATENT NO.        : 6,593,497 B1                                         Page 1 of 1
APPLICATION NO.   : 09/504761
DATED             : July 15, 2003
INVENTOR(S)       : Choi et al.

It is certified that error appears in the above-identified patent and that said Letters Patent is hereby corrected as shown below:

Column 110
At line 34, (Claim 1), "Ar" should read -- $Ar^2$ --; and
At line 50, (Claim 1), "$R^6$" should read -- $R^{6'}$ --.

Column 111
At line 49, (Claim 2), "$R^6$" should read -- $R^{6'}$ --.

Column 112
At line 2, (Claim 2), "2yanoindolyl" should read -- 2-cyanoindolyl --; and
At line 29, (Claim 3), "2,5direthoxyphenyl" should read -- 2,5-dimethoxyphenyl --.

Column 113
At lines 35-40, (Claim 3), the formula:

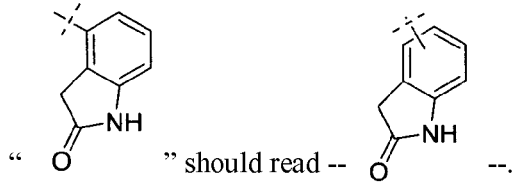 should read -- --.

Signed and Sealed this

Tenth Day of October, 2006

JON W. DUDAS
*Director of the United States Patent and Trademark Office*